US012642857B2

(12) United States Patent
Gray et al.

(10) Patent No.: US 12,642,857 B2
(45) Date of Patent: Jun. 2, 2026

(54) DEGRADATION OF AKT BY CONJUGATION OF ATP-COMPETITIVE AKT INHIBITOR GDC-0068 WITH E3 LIGASE LIGANDS AND METHODS OF USE

(71) Applicants: DANA-FARBER CANCER INSTITUTE, INC., Boston, MA (US); BETH ISRAEL DEACONESS MEDICAL CENTER, INC., Boston, MA (US)

(72) Inventors: Nathanael Gray, Boston, MA (US); Inchul You, Boston, MA (US); Tinghu Zhang, Brookline, MA (US); Eric Fischer, Chestnut Hill, MA (US); Katherine Donovan, Boston, MA (US); Emily Erickson, Brookline, MA (US); Alex Toker, Dedham, MA (US)

(73) Assignees: DANA-FARBER CANCER INSTITUTE, INC., Boston, MA (US); BETH ISRAEL DEACONESS MEDICAL CENTER, INC., Boston, MA (US)

( * ) Notice: Subject to any disclaimer, the term of this patent is extended or adjusted under 35 U.S.C. 154(b) by 1276 days.

(21) Appl. No.: 17/601,640

(22) PCT Filed: Apr. 8, 2020

(86) PCT No.: PCT/US2020/027236

§ 371 (c)(1),
(2) Date: Oct. 5, 2021

(87) PCT Pub. No.: WO2020/210337

PCT Pub. Date: Oct. 15, 2020

(65) Prior Publication Data

US 2022/0226481 A1 Jul. 21, 2022

Related U.S. Application Data

(60) Provisional application No. 62/831,267, filed on Apr. 9, 2019.

(51) Int. Cl.

| | |
|---|---|
| ***A61K 47/55*** | (2017.01) |
| ***A61K 31/337*** | (2006.01) |
| ***A61K 47/54*** | (2017.01) |
| ***A61P 35/00*** | (2006.01) |
| ***C07D 401/14*** | (2006.01) |
| ***C07D 417/14*** | (2006.01) |

(52) U.S. Cl.

CPC ............ *A61K 47/55* (2017.08); *A61K 31/337* (2013.01); *A61K 47/545* (2017.08); *A61P 35/00* (2018.01); *C07D 401/14* (2013.01); *C07D 417/14* (2013.01)

(58) Field of Classification Search

CPC ..... A61K 47/55; C07D 401/14; C07D 417/14

See application file for complete search history.

(56) References Cited

U.S. PATENT DOCUMENTS

| | | | |
|---|---|---|---|
| 2015/0291562 | A1 | 10/2015 | Crew et al. |
| 2017/0119901 | A1 | 5/2017 | Bachovchin et al. |

FOREIGN PATENT DOCUMENTS

| | | | |
|---|---|---|---|
| WO | 2008/006040 | A1 | 1/2008 |
| WO | 2017/185031 | A1 | 10/2017 |
| WO | 2017197055 | A1 | 11/2017 |
| WO | 2019/173516 | A1 | 9/2019 |

OTHER PUBLICATIONS

Bricelj et al., "E3 Ligase Ligands in Successful PROTACs: An Overview of Syntheses and Linker Attachment Points", 2021, Frontiers in Chemistry, 9, pp. 1-46 (Year: 2021).*

Kim et al., "Ipatasertib plus paclitaxel versus placebo plus paclitaxel as first-line therapy for metastatic triple-negative breast cancer (LOTUS): a multicentre, randomised, double-blind, placebo-controlled, phase 2 trial", 2017, Lancet Oncology, 18, pp. 1360-1372 (Year: 2017).*

Song et al., "AKT as a Therapeutic Target for Cancer", 2019, Cancer Research, 79, pp. 1019-1031 (Year: 2019).*

Ottis et al., "Proteolysis-Targeting Chimeras: Induced Protein Degradation as Therapeutic Strategy", ACS Chem. Biol., 2017, vol. 12, pp. 892-898.

You, I., et al., "Discovery of an AKT Degrader with Prolonged Inhibition of Downstream Signaling", BioRxiv preprint, 2019, pp. 1-14.

Blake et al., "Discovery and Preclinical Pharmacology of a Selective ATP-Competitive Akt Inhibitor (GDC-0068) for the Treatment of Human Tumors", J. Med. Chem., 2012, vol. 55, pp. 8110-8127.

Davis, B. R., et al. "Preclinical Pharmacology of AZD5363, an Inhibitor of AKT: Pharmacodynamics, Antitumor Activity, and Correlation of Monotherapy Activity with Genetic Background", Mol. Cancer Ther., 2012, vol. 11, No. 4, pp. 873-887.

(Continued)

*Primary Examiner* — Brenda L Coleman
*Assistant Examiner* — Madeline E Braun
(74) *Attorney, Agent, or Firm* — ArentFox Schiff LLP; Daniel W. Clarke; Shawn P. Foley

(57) ABSTRACT

Bifunctional compounds comprising a GDC-0068 analog that binds AKT isoforms AKT1, 2 and 3 and a degron which represents a moiety that binds an E3 ubiquitin ligase, covalently attached to each other by a linker, pharmaceutical compositions, and methods for treating diseases or conditions mediated by dysfunctional AKT activity.

30 Claims, 13 Drawing Sheets

(56) References Cited

OTHER PUBLICATIONS

Li, X. et al., "Proteolysis-targeting chimera (PROTAC) for targeted protein degradation and cancer therapy", J. Hematol. Oncol., 2020, vol. 13, No. 50, 14 pages.
Mundi, P. S., et al., "AKT in cancer: new molecular insights and advances in drug development", Br. J. Clin. Pharmacol., 2016, vol. 82, pp. 943-956.
Simpson, D. L. et al., "Killing of Human Myelomonocytic Leukemia and Lymphocytic Cell Lines by Actinobacillus actinomycetemcomitans Leukotoxin", Infection and Immunity, 1988, vol. 56, No. 5, pp. 1162-1166.

* cited by examiner 24h in Full Serum
20ug Protein 24h in Full Serum
20ug Protein 24h in Full Serum
20ug Protein 24h in Full Serum
20ug Protein

DEGRADATION OF AKT BY CONJUGATION OF ATP-COMPETITIVE AKT INHIBITOR GDC-0068 WITH E3 LIGASE LIGANDS AND METHODS OF USE

RELATED APPLICATIONS

This application is a national stage application, filed under 35 U.S.C. § 371, of International Application No. PCT/US2020/027236, filed on Apr. 8, 2020, which claims the benefit of priority under 35 U.S.C. § 119 (e) to U.S. Provisional Application No. 62/831,267, filed on Apr. 9, 2019, each of which is incorporated herein by reference in its entirety.

GOVERNMENT LICENSE RIGHTS

This invention was made with government support under grant numbers R01 CA200671 and R01 CA218278 awarded by the National Institutes of Health. The government has certain rights in the invention.

BACKGROUND OF THE INVENTION

Hyperactivation of AKT, also known as Protein Kinase B (PKB), is frequently observed in a variety of solid tumors and hematological malignancies (Manning and Toker, Cell 169:381-405 (2017)). Hyperactivated AKT not only protects cancer cells from apoptosis, but also promotes uncontrolled cell-cycle progression, making AKT an attractive therapeutic target for cancer (Kandel et al., Mol. Cell. Biol. 22:7831-7841 (2008)).

While several ATP-competitive and allosteric AKT inhibitors are currently under clinical trials, the inhibitors have faced several limitations, especially as single agents. ATP-competitive inhibitors, such as GSK690693, fail to inhibit the kinase-independent functions of AKT, leading to cancer cell survival (Vivanco et al., eLife 3:e03751 (2014)). On the other hand, allosteric AKT inhibitors exhibit reduced efficacy in cancer cells with E17K mutated AKT1 (Parikh et al., Proc. Natl. Acad. Sci. 109:19368-19373 (2012)).

Thus, there remains a need for more effective targeting and inhibition of all three isoforms of AKT (AKT1, AKT2 and AKT3) for purposes of cancer treatment.

SUMMARY OF THE INVENTION

A first aspect of the present invention is directed to a bifunctional compound, comprising a targeting ligand that binds AKT1, 2 and 3 and a degron which represents a moiety that binds an E3 ubiquitin ligase, covalently attached to each other by a linker, wherein the compound has a structure represented by formula I:

(I)

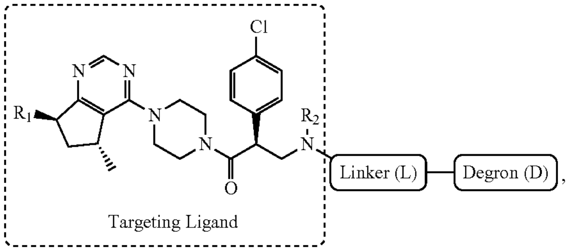

wherein $R_1$ is H or OH;

$R_2$ is H or methyl;

or a pharmaceutically acceptable salt or stereoisomer thereof.

A second aspect of the present invention is directed to a pharmaceutical composition containing a therapeutically effective amount of a compound of formula I, or a pharmaceutically acceptable salt or stereoisomer thereof, and pharmaceutically acceptable carrier.

A further aspect of the invention is directed to a method of treating a disease or disorder mediated by dysregulated or dysfunctional AKT (also known as Protein Kinase B (PKB)) activity, that includes administrating a therapeutically effective amount of an inventive bifunctional compound or a pharmaceutically acceptable salt or stereoisomer thereof, to a subject in need thereof.

Further aspects of the present invention are directed to methods of making the bifunctional compounds.

As demonstrated in working examples herein, Applicant has surprisingly discovered that unlike the pan-AKT inhibitor GDC-0068, per se, inventive bifunctional compounds that contain GDC-0068 or its analogs as the AKT targeting ligand exhibit degradation activity against all three AKT isoforms and display enhanced anti-proliferative effects relative to GDC-0068. Notably, bifunctional compound 10 promoted sustained AKT degradation and inhibition of downstream signaling effects for up to 96 hours, even after compound washout. These results suggest that AKT degradation may confer prolonged pharmacological effects compared with inhibition, and highlight the potential advantages of AKT-targeted degradation.

Without intending to be bound by any particular theory of operation, the bifunctional compounds of formula I of the present invention are believed to degrade of all three isoforms of AKT (AKT1, AKT2 and AKT3) via the cell's ubiquitin/proteasome system, whose function is to routinely identify and remove damaged proteins. The degron functional moiety recruits the E3 ubiquitin ligase to tag AKT (which is bound by the targeting ligand functionality) for ubiquitination and degradation through the proteasome, which is a large endogenous complex that degrades the ubiquitinated protein into small peptide fragments. After destruction of an AKT molecule, the degrader is released and continues to be active. Thus, by engaging and exploiting the body's own natural protein disposal system, the bifunctional compounds of the present invention may represent a potential improvement over current small molecule inhibitors of AKT in the treatment of cancers that have proven or may prove to be difficult to treat. Further, chemical degradation of AKT may have significant advantages over kinase inhibition by AKT inhibitors and thus more likely clinical applicability due to abrogation of AKT, scaffolding, and nuclear activities in many cancers.

The inventive AKT degraders may offer several additional advantages over existing AKT inhibitors. For example, in view of data suggesting that degraders act in a catalytic fashion (i.e., a single degrader molecule can induce degradation of multiple target proteins), effective intracellular concentrations of degraders may be significantly lower than for conventional AKT inhibitors. Also, because degraders cause complete elimination of the protein by the proteasome, pharmacodynamic effects of the degraders are dictated by protein resynthesis rates similar to what is observed for covalent inhibitors. Even further, de novo resistance mutations to selective degraders of AKT are less likely to emerge, given that efficient degradation can be achieved even with lower affinity warheads.

DETAILED DESCRIPTION

Figure 1:
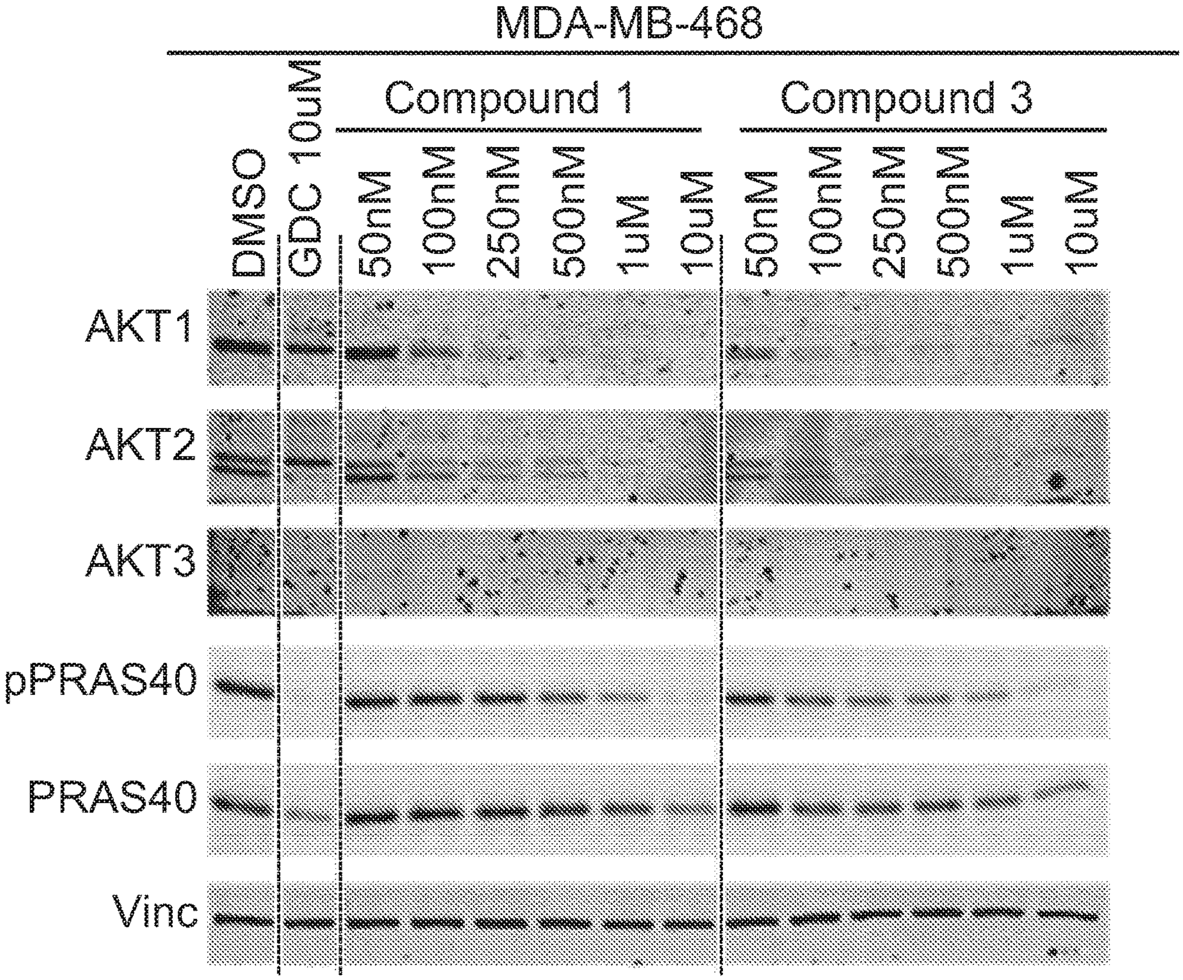
FIG. 1 is an immunoblot that shows the degradation of all three AKT (Protein Kinase B (PKB)) isoforms in MDA-MB-468 cell lines with different concentrations of inventive bifunctional compounds 1 and 3. DMSO and AKT inhibitor GDC-0068 were used as negative and positive controls, respectively.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used in the description and the appended claims, the singular forms “a”, “an”, and “the” include plural referents unless the context clearly dictates otherwise. Thus, for example, reference to “a composition” includes mixtures of two or more such compositions, reference to “an inhibitor” includes mixtures of two or more such inhibitors, and the like.

Unless stated otherwise, the term “about” means within 10% (e.g., within 5%, 2% or 1%) of the particular value modified by the term “about.”

The transitional term “comprising,” which is synonymous with “including,” “containing,” or “characterized by,” is inclusive or open-ended and does not exclude additional, unrecited elements or method steps. By contrast, the transitional phrase “consisting of” excludes any element, step, or ingredient not specified in the claim. The transitional phrase “consisting essentially of” limits the scope of a claim to the specified materials or steps “and those that do not materially affect the basic and novel characteristic(s)” of the claimed invention.

With respect to compounds of the present invention, and to the extent the following terms are used herein to further describe them, the following definitions apply.

As used herein, the term “alkyl” refers to a saturated linear or branched-chain monovalent hydrocarbon radical. In one embodiment, the alkyl radical is a C1-C18 group. In other embodiments, the alkyl radical is a C0-C6, C0-C05, C0-C3, C1-C12, C1-C8, C1-C6, C1-C5, C1-C4 or C1-C3 group (wherein C0 alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a C1-C3 alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms (C1-C8 alkylene). In other embodiments, an alkylene group contains one to 5 carbon atoms (C1-05 alkylene). In other embodiments, an alkylene group contains one to 4 carbon atoms (C1-C4 alkylene). In other embodiments, an alkylene contains one to three carbon atoms (C1-C3 alkylene). In other embodiments, an alkylene group contains one to two carbon atoms (C1-C2 alkylene). In other embodiments, an alkylene group contains one carbon atom (C1 alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a C2-C18 group. In other embodiments, the alkenyl radical is a C2-C12, C2-C10, C2-C8, C2-C6 or C2-C3 group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto, which is the point of attachment to the greater molecule. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "alkoxylene" refers to a saturated monovalent aliphatic radicals of the general formula (—O-CnH2n-) where n represents an integer (e.g., 1, 2, 3, 4, 5, 6, or 7) and is inclusive of both straight-chain and branched-chain radicals. The alkoxylene chain may be attached to the rest of the molecule through a single bond and to the radical group through a single bond. In some embodiments, the alkoxylene group contains one to 3 carbon atoms (—O—C1-C3 alkoxylene). In other embodiments, an alkoxylene group contains one to 5 carbon atoms (—O—C1-C5 alkoxylene).

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring (e.g., phenyl) system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1] heptane, bicyclo[2.2.2]octane, naphthalene, and bicyclo [3.2.2] nonane. Representative examples of spiro carbocyclyls include spiro[2.2]pentane, spiro[2.3]hexane, spiro[2.4] heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula -Rc-aryl where Rc is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O-Rc-aryl where Rc is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

The term heteroaryl also embraces N-heteroaryl groups which as used herein refers to a heteroaryl group, as defined above, and which contains at least one nitrogen atom and where the point of attachment of the N-heteroaryl group to the rest of the molecule is the nitrogen atom in the heteroaryl group. The term heteroaryl further embraces C-heteroaryl groups which as used herein refer to a heteroaryl group as defined above and where the point of attachment of the heteroaryl group to the rest of the molecule is through a carbon atom in the heteroaryl group. The term heteroaryl further embraces heteroarylalkyl groups which as disclosed above refer to a group of the formula -Rc-heteroaryl, wherein Rc is an alkylene chain as defined above. The term heteroaryl further embraces heteroaralkoxy (or heteroarylalkoxy) groups which as used herein refer to a group bonded through an oxygen atom of the formula —O-Rc-heteroaryl, where Rc is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-$C_6$, C1-5, C1-4, C1-3, C1-2, C1), haloalkyl (e.g., $CF_3$), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The term "binding" as it relates to interaction between the targeting ligand of the compound of formula I and the targeted protein or proteins, which in this invention are all three all three isoforms of AKT, i.e., AKT1, 2 and 3, typically refers to an inter-molecular interaction that may be preferential or substantially specific in that binding of the targeting ligand with other proteinaceous entities present in the cell is functionally insignificant. The present bifunctional compounds may preferentially bind and recruit all three isoforms of AKT for targeted degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the present invention is directed to a bifunctional compound, comprising a targeting ligand that binds AKT1, 2 and 3 and a degron which represents a moiety that binds an E3 ubiquitin ligase, covalently attached to each other by a linker, wherein the compound has a structure represented by formula I:

(I)

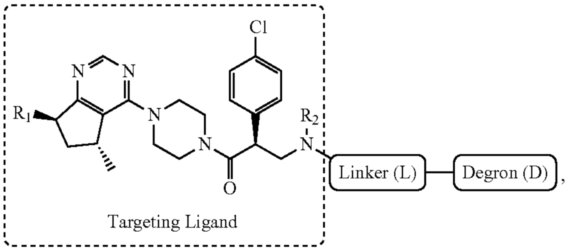

, wherein $R_1$ is H or OH;

$R_2$ is H, methyl, ethyl, or isopropyl;

or a pharmaceutically acceptable salt or stereoisomer thereof.

Targeting Ligands

In some embodiments, wherein $R_1$ and $R_2$ are H, the targeting ligand has a structure represented by structure TL1:

(TL-1)

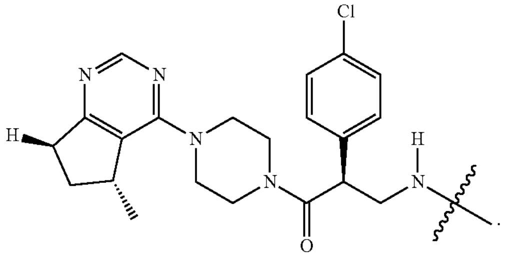

Thus, in some embodiments, the compounds of the present invention have a structure represented by formula I-1:

(I-1)

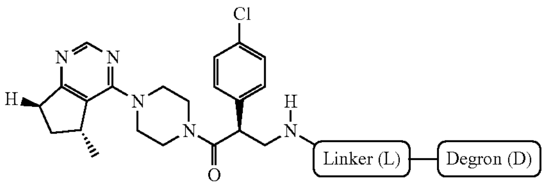

or a pharmaceutically acceptable salt or stereoisomer thereof.

In some embodiments, wherein $R_1$ is H and $R_2$ is methyl, the targeting ligand has a structure represented by structure TL1:

(TL-2)

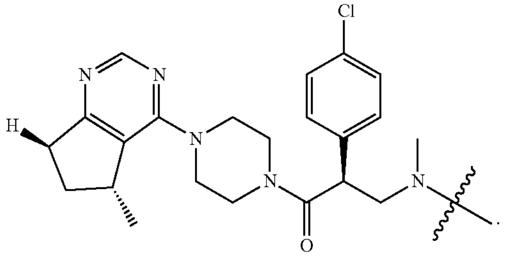

Thus, in some embodiments, the compounds of the present invention have a structure represented by formula I-2:

(I-2)

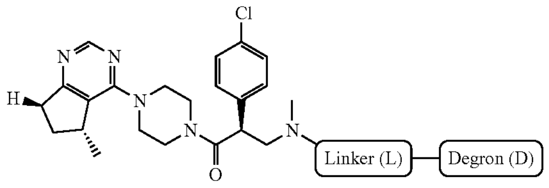

or a pharmaceutically acceptable salt or stereoisomer thereof.

In some embodiments, wherein $R_1$ is OH and $R_2$ is H, the targeting ligand has a structure represented by structure TL3:

(TL-3)

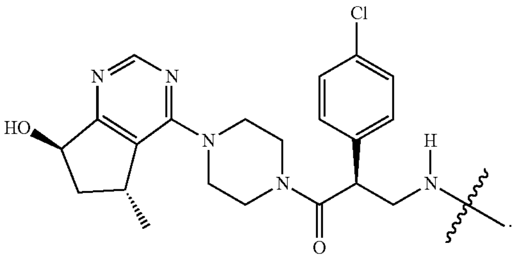

Thus, in some embodiments, the compounds of the present invention have a structure represented by formula I-3:

(I-3)

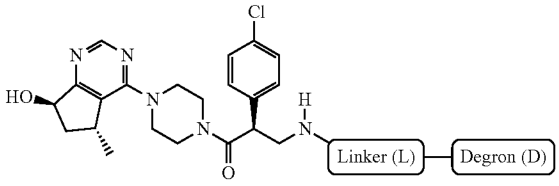

or a pharmaceutically acceptable salt or stereoisomer thereof.

In some embodiments, wherein $R_1$ is OH and $R_2$ is methyl, the targeting ligand has a structure represented by structure TL4:

(TL-4)

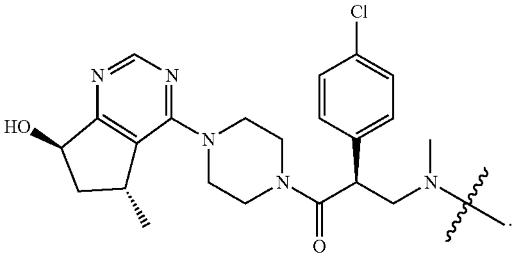

Thus, in some embodiments, the compounds of the present invention have a structure represented by formula I-4:

(I-4)

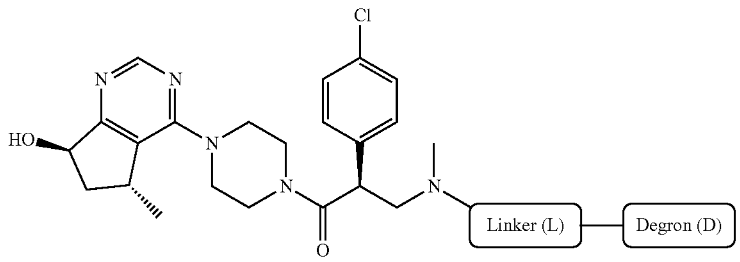

or a pharmaceutically acceptable salt or stereoisomer thereof.

Linkers

The Linker ("L") provides a covalent attachment of the targeting ligand to the Degron. The structure of Linker may not be critical, provided it does not substantially interfere with the activity of the targeting ligand or the Degron. In some embodiments, the Linker includes an alkylene linker (e.g., having 0-11, inclusive, alkylene units). In other embodiments, the Linker may include a bivalent alkylene linker interrupted by, or terminating in (at either or both termini at least one of —O—, —S—, —N(R')—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments the linker may include C1-C10 alkylene terminating in NH— group wherein the nitrogen is also bound to the degron.

In some embodiments, the linker includes an alkylene chain having 1-10 alkylene units and interrupted by or terminating in

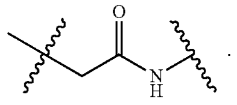 [SMILES: *CC(=O)N*]

.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of alkylene linkers that may be suitable for use in the present invention include the following (L1)

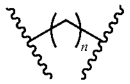

, wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

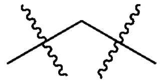

;

(L1-b)

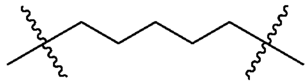

;

(L1-c)

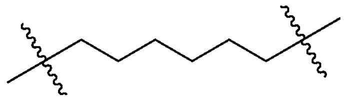

;

(L1-d)

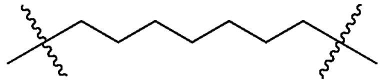

; and (L1-e)

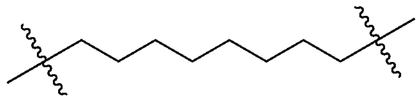

;

alkylene chains terminating in various functional groups (as described above), examples of which are as follows:

(L2-a)

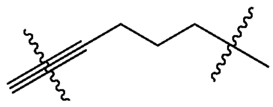

;

(L2-b)

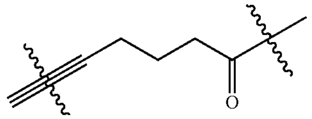

;

(L2-c)

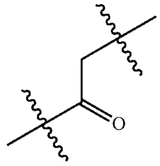

;

-continued (L2-d)

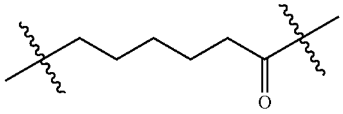
;

(L2-e)

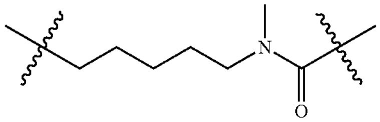
;

(L2-f)

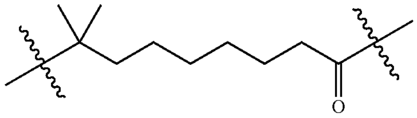
; and (L2-g)

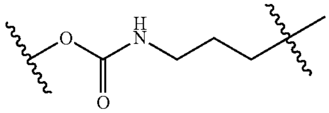
;

alkylene chains interrupted with various functional groups (as described above), examples of which are as follows:

(L3-a)

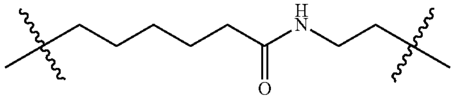
;

(L3-b)

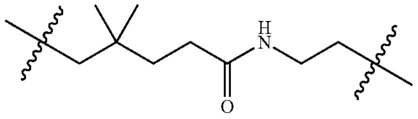
;

(L3-c)

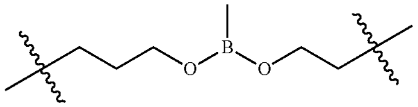
; and (L3-d)

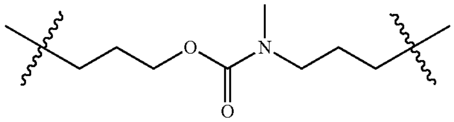
;

alkylene chains interrupted or terminating with heterocyclene groups, e.g., (L4)

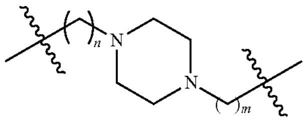
, wherein m and n are independently integers of 0-10, examples of which include:

(L4-a)

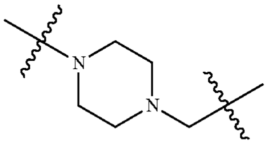
;

(L4-b)

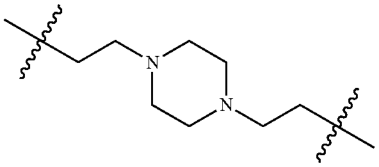
;

(L4-c)

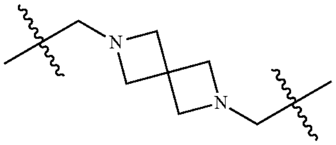
;

(L4-d)

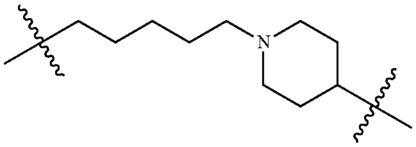
; and (L4-e)

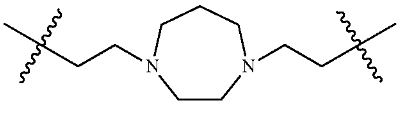
;

alkylene chains interrupted by amide, heterocyclene and/or aryl groups, examples of which include:

(L5-a)

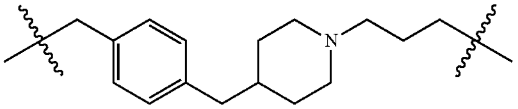
; and (L5-b)

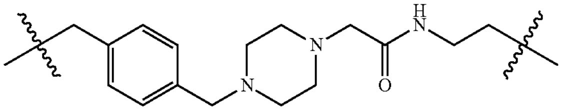
;

alkylene chains interrupted by heterocyclene and aryl groups, and a heteroatom, examples of which include:

(L6-a)

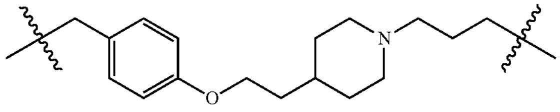
;

-continued (L6-b)

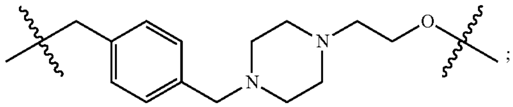

; and (L6-c)

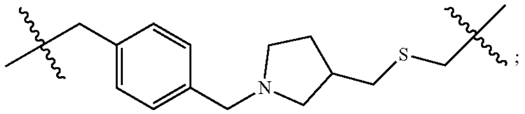

;

and alkylene chains interrupted by a heteroatom such as N, O or B, e.g., (L7)

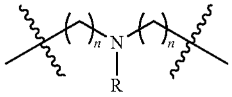

, wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

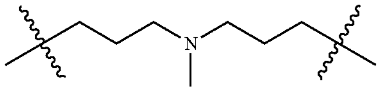

.

In some embodiments, the linker may include a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —N(R')$S(O)_2$—, —$S(O)_2N(R')$—, —N(R')S(O)—, —S(O)N(R')—, —N(R')$S(O)_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 2-8 PEG units and terminating in

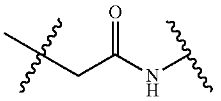

.

Examples of linkers that include a polyethylene glycol chain include:

(L8)

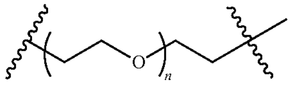

, wherein n is an integer of 2-10, examples of which include:

(L8-a)

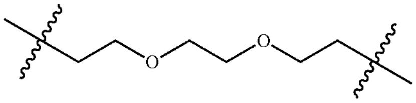

;

(L8-b)

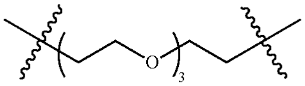

;

(L8-c)

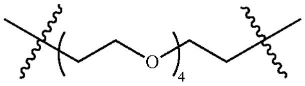

; and (L8-d)

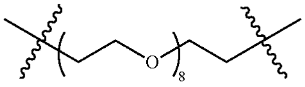

.

In some embodiments, the polyethylene glycol linker may terminate in a functional group, examples of which are as follows:

(L9-a)

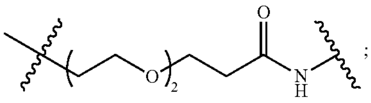

;

(L9-b)

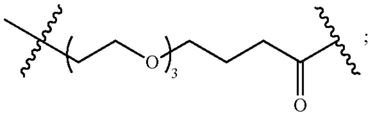

;

(L9-c)

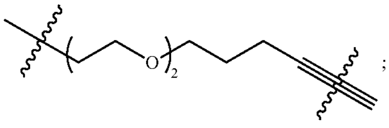

;

(L9-d)

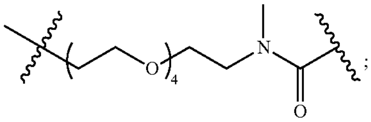

; and (L9-e)

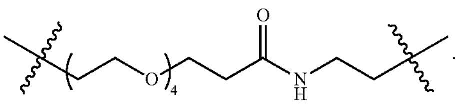

.

In some embodiments, the linker is represented by formula L10:

(L10)

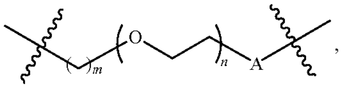, wherein

A is absent, CO, or $NR_3COCH_2$, wherein $R_3$ is H or methyl;

m is independently 1 to 10;

and n independently is 0, 1, 2, or 3.

Thus, in some embodiments, the compounds of the present invention are represented by structure I-5:

(I-5)

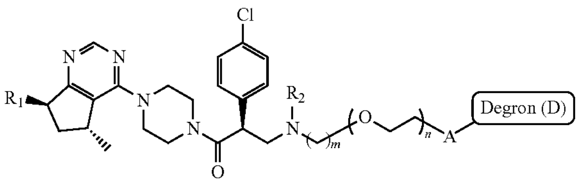

or a pharmaceutically acceptable salt or stereoisomer thereof, wherein

A is absent, CO, or $NR_3COCH_2$, wherein $R_3$ is H or methyl;

$R_1$ is H or OH;

$R_2$ is H, methyl, ethyl, or isopropyl;

m is independently 1 to 10;

and n independently is 0, 1, 2, or 3.

In some embodiments, the linker is represented by any one of structures:

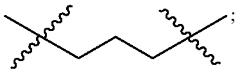; 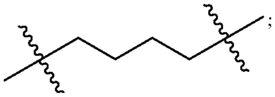;

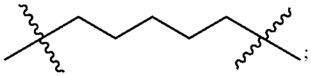;

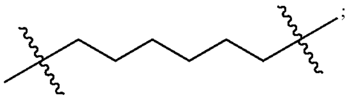;

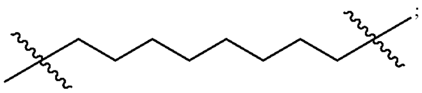;

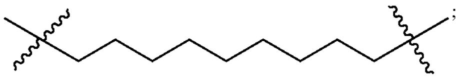;

-continued

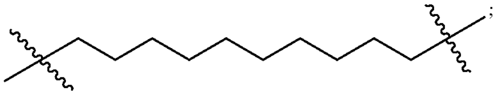;

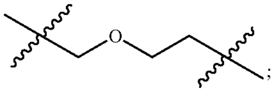;

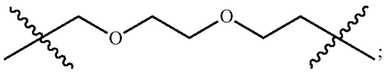;

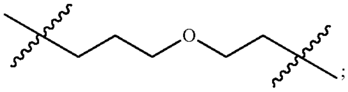;

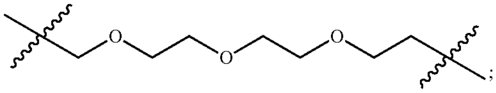;

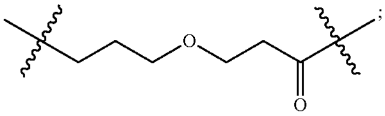;

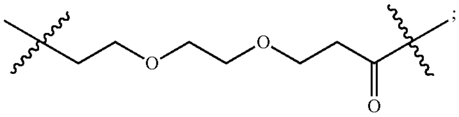;

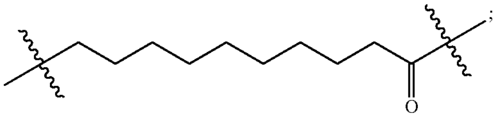;

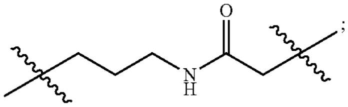;

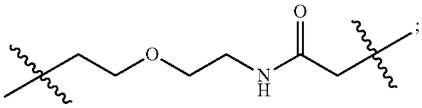;

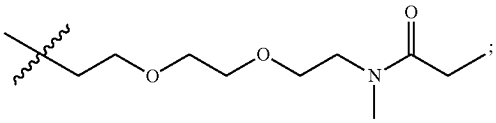; and

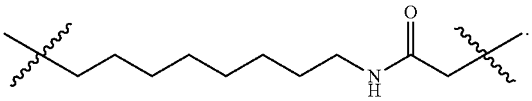.

Thus, in some embodiments, the compounds of the present invention are represented by any one of formulae I-6 to I-21:
(I-6)
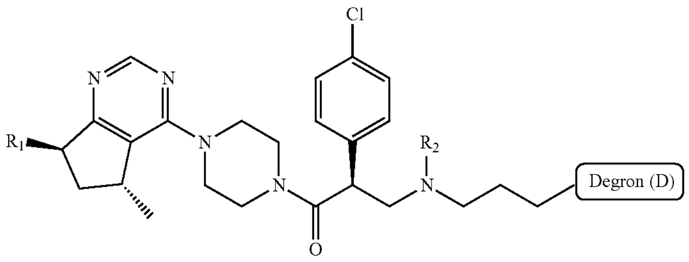
;
(I-7)
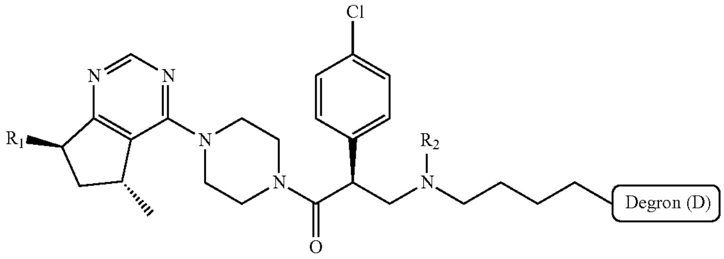
;
(I-8)
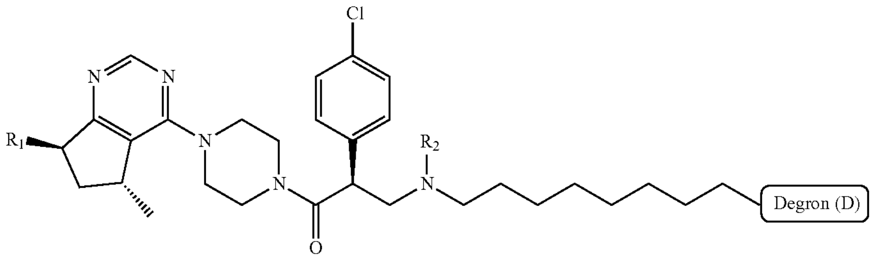
;
(I-9)
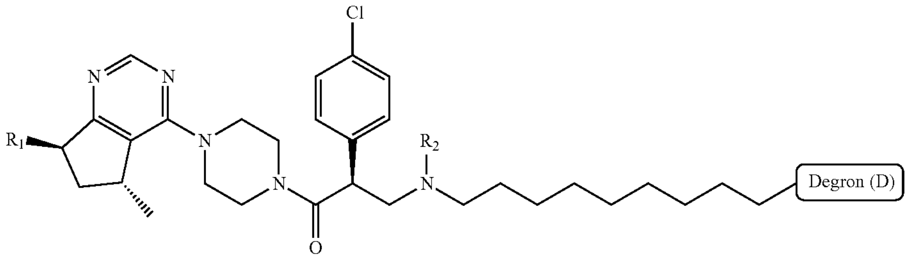
;
(I-10)
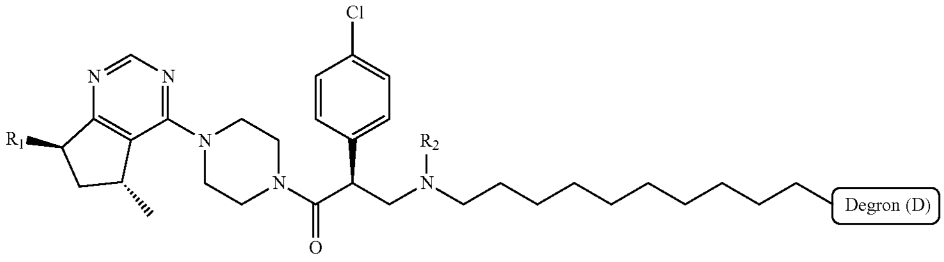
;

-continued
(I-11)
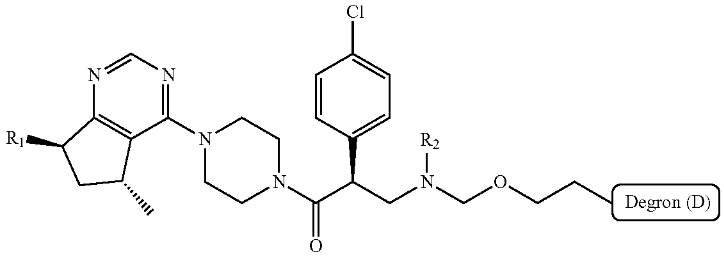
;
(I-12)
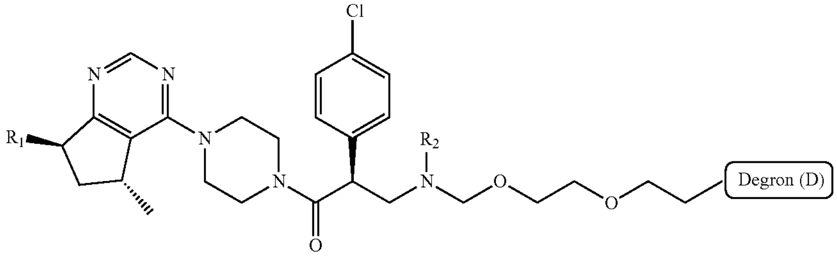
;
(I-13)
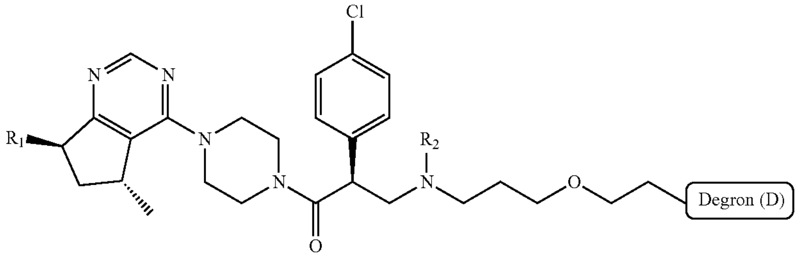
;
(I-14)
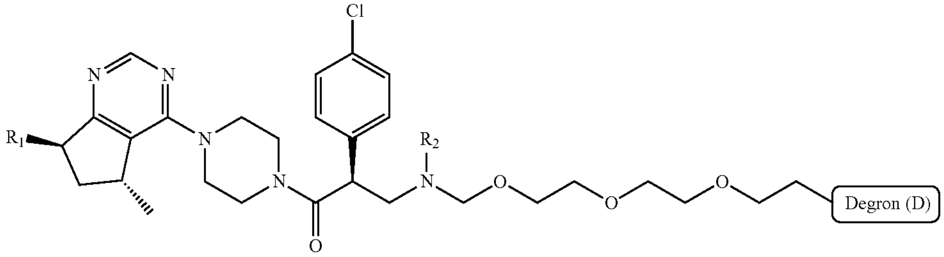
;
(I-15)
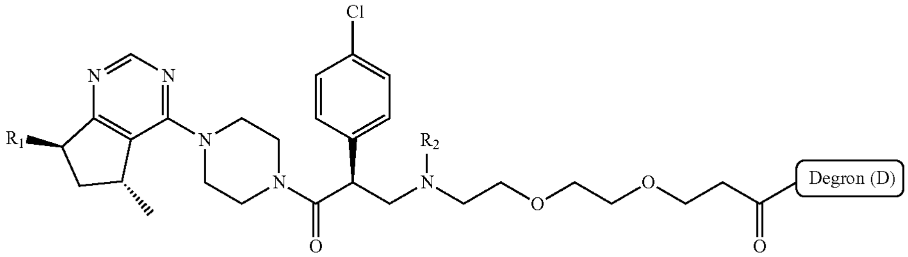
;
(I-16)
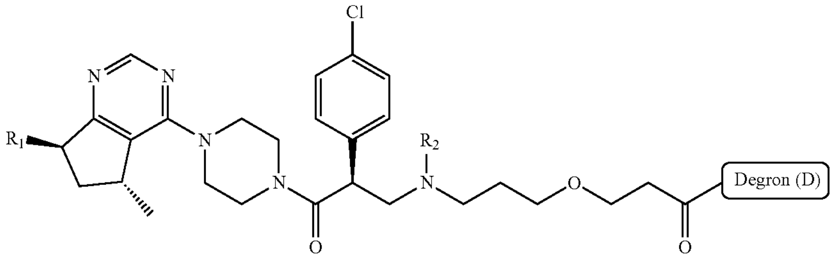
;

-continued (I-17)

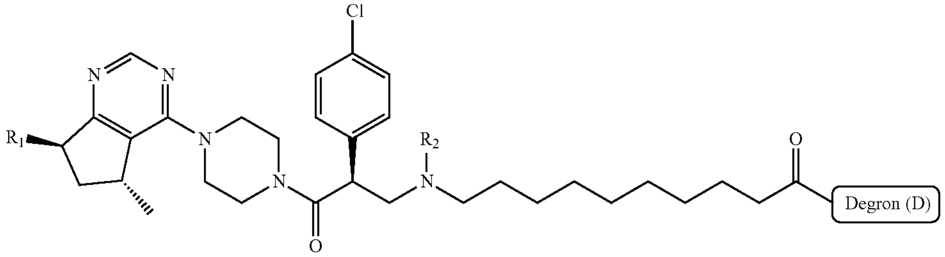

;

(I-18)

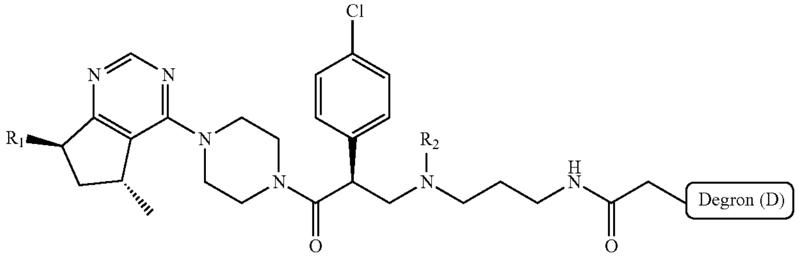

;

(I-19)

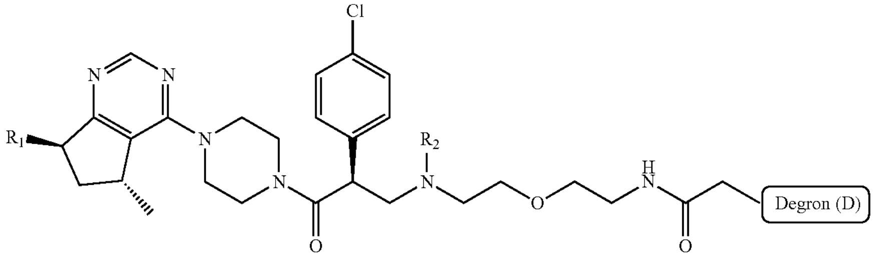

;

(I-20)

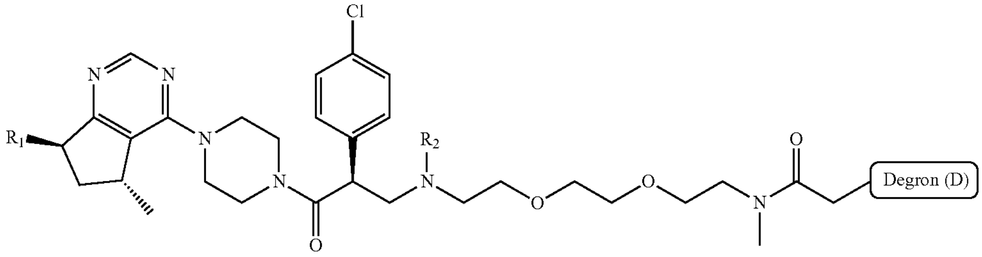

;

(I-21)

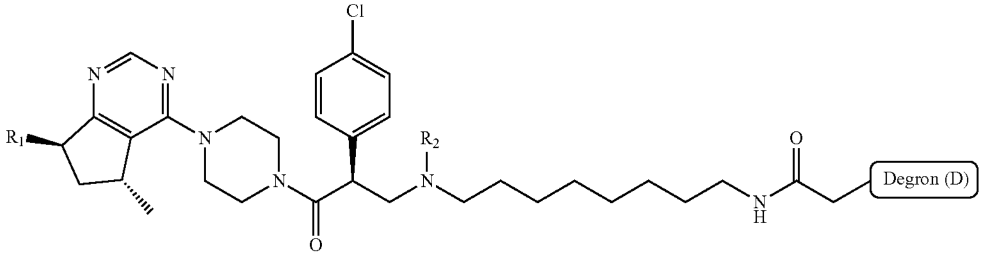

;

or a pharmaceutically acceptable salt or stereoisomer thereof, wherein $R_1$ is H or OH; and $R_2$ is H, methyl, ethyl, or isopropyl.

Degron

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon and is represented by any one of structures D1a to D1h.

(D1a)

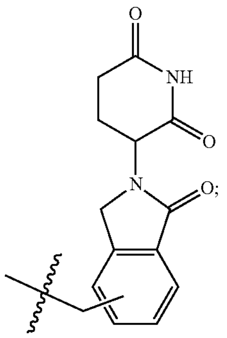

(D1b)

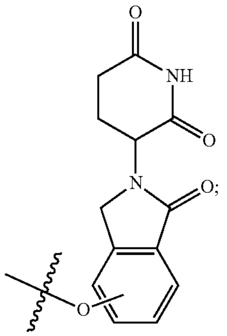

(D1c)

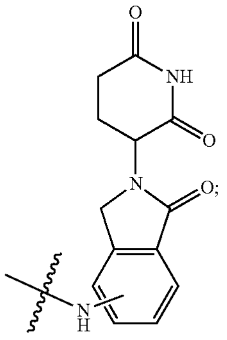

(D1d)

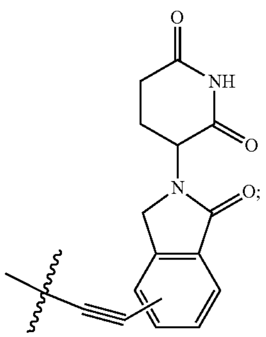

-continued (D1e)

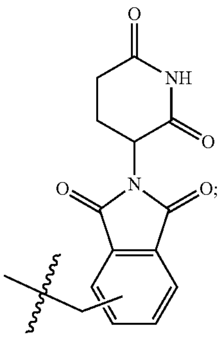

(D1f)

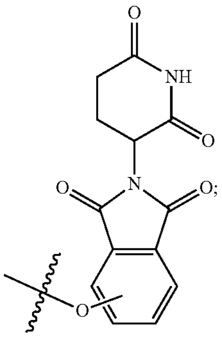

(D1g)

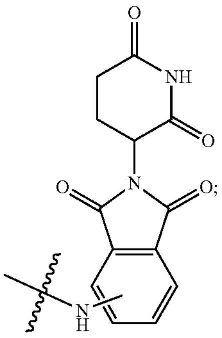

and (D1h)

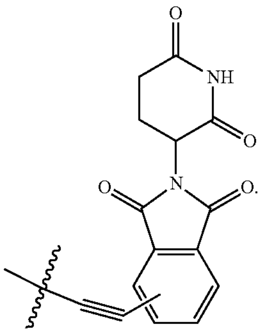

Yet other degrons that bind cereblon and which may be suitable for use in the present invention are disclosed in U.S. Pat. No. 9,770,512, and U.S. Patent Application Publication Nos. 2018/0015087, 2018/0009779, 2016/0243247, 2016/0235731, 2016/0235730, and 2016/0176916, and International Patent Publications WO 2017/197055, WO 2017/197051, WO 2017/197036, WO 2017/197056 and WO 2017/197046.

Thus in some embodiments, the compounds of the present invention are represented by any one of formulae I-21 to I-29:

(I-22)
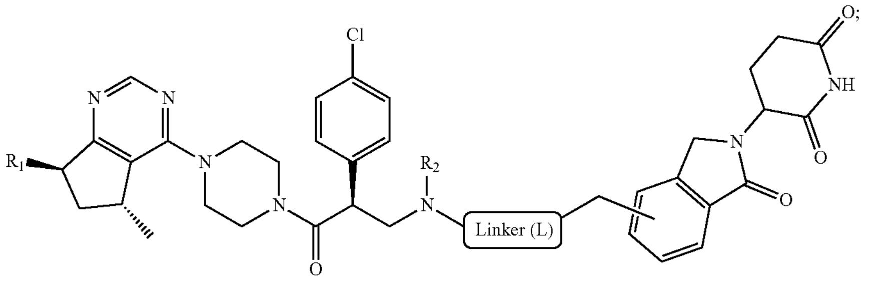
(I-23)
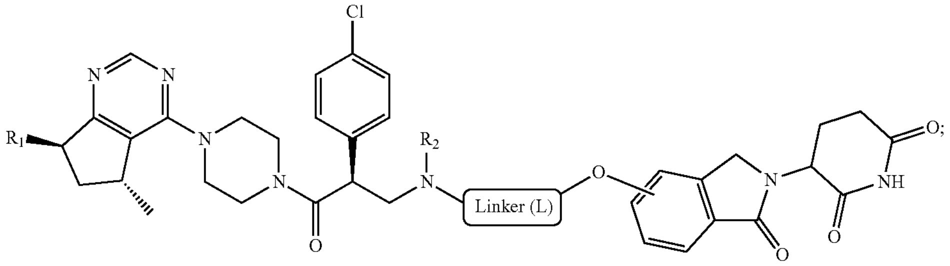
(I-24)
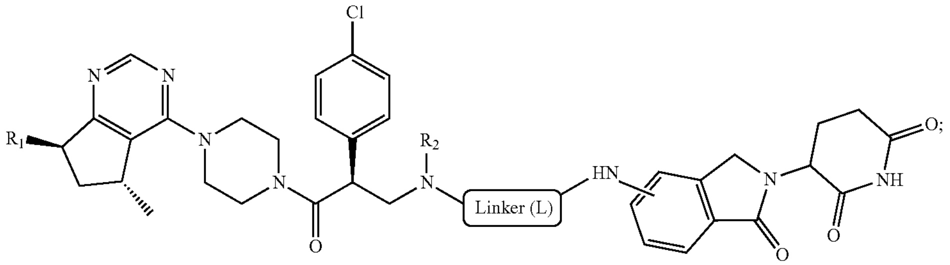
(I-25)
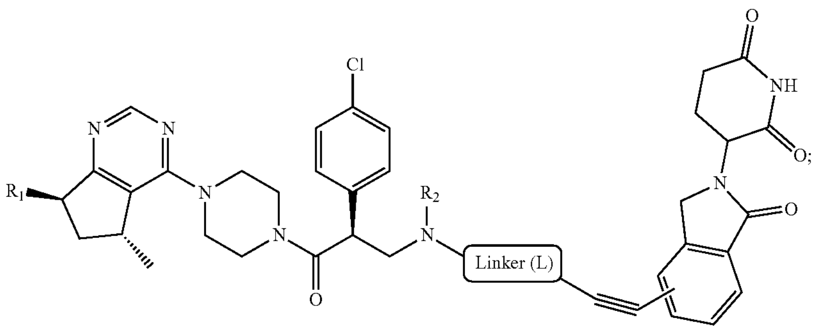

-continued
(I-26)
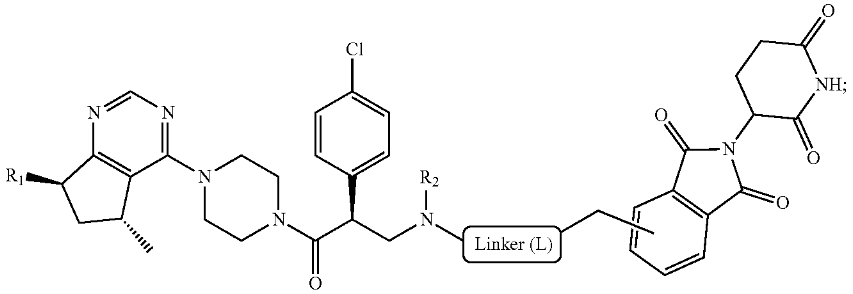
(I-27)
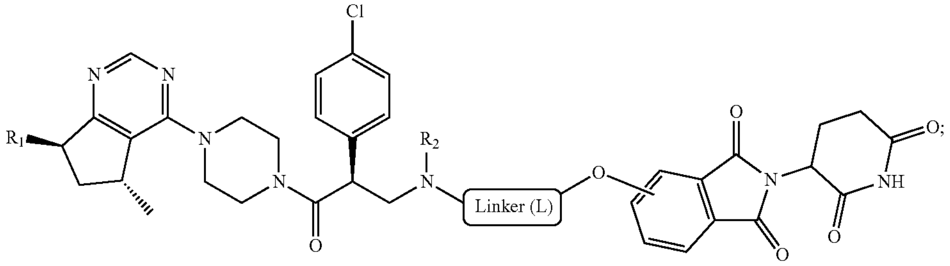
(I-28)
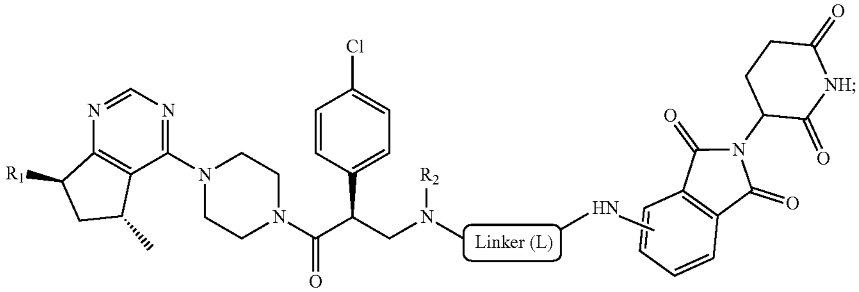
and
(I-29)
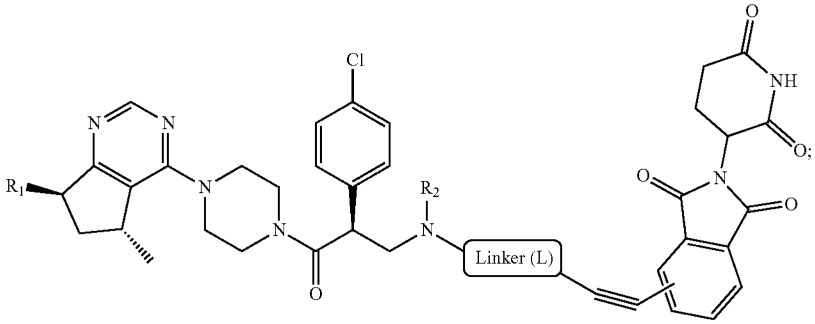

or a pharmaceutically acceptable salt or stereoisomer thereof, wherein $R_1$ is H or OH; and $R_2$ is H, methyl, ethyl, or isopropyl.

In some embodiments, the E3 ubiquitin ligase that is bound by the degron is the von Hippel-Lindau (VHL) tumor suppressor. See, Iwai et al., Proc. Nat'l. Acad. Sci. USA 96:12436-41 (1999).

Additional examples of the degrons that bind VHL are represented by the following formulae:

(D2a)

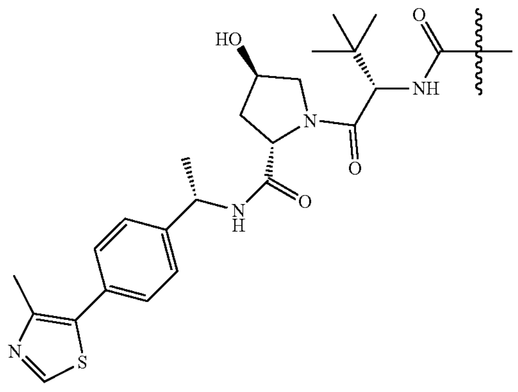

;

(D2b)

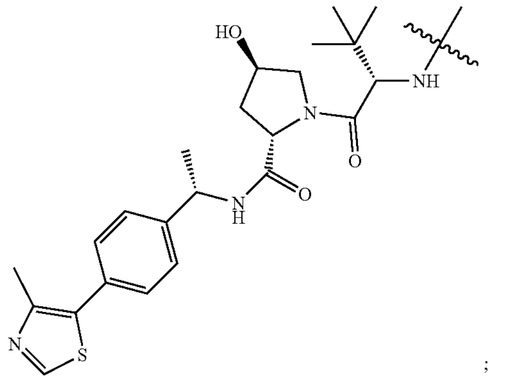

;

-continued (D2c)

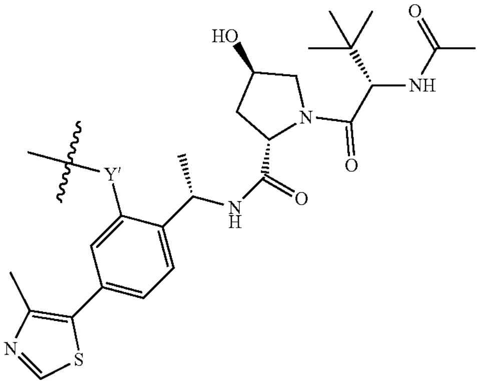

, wherein Y' is a bond, N, O or C;

(D2d)

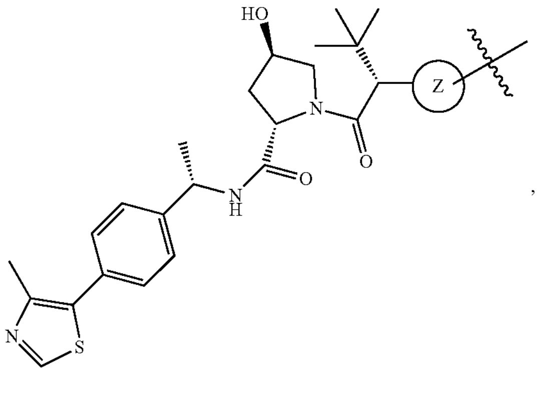

, wherein Z is a cyclic group, which in some embodiments is a $C_5$-$C_6$ carbocyclic or heterocyclic group;

and (D2e)

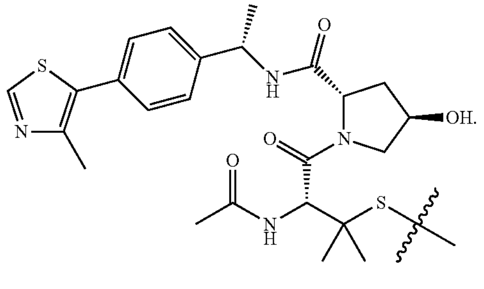

In some embodiments, the present invention provides a compound represented by any one of formulae I-30 to I-34:
(I-30)
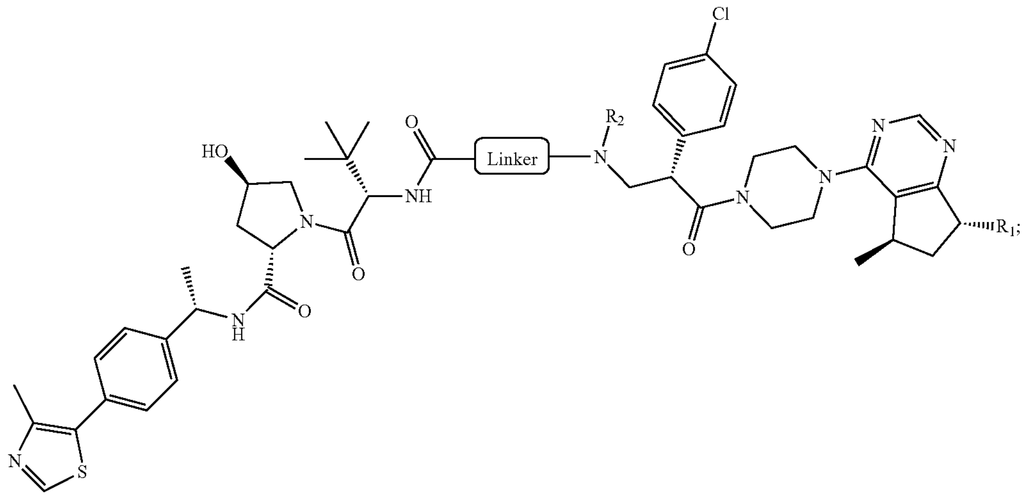
(I-31)
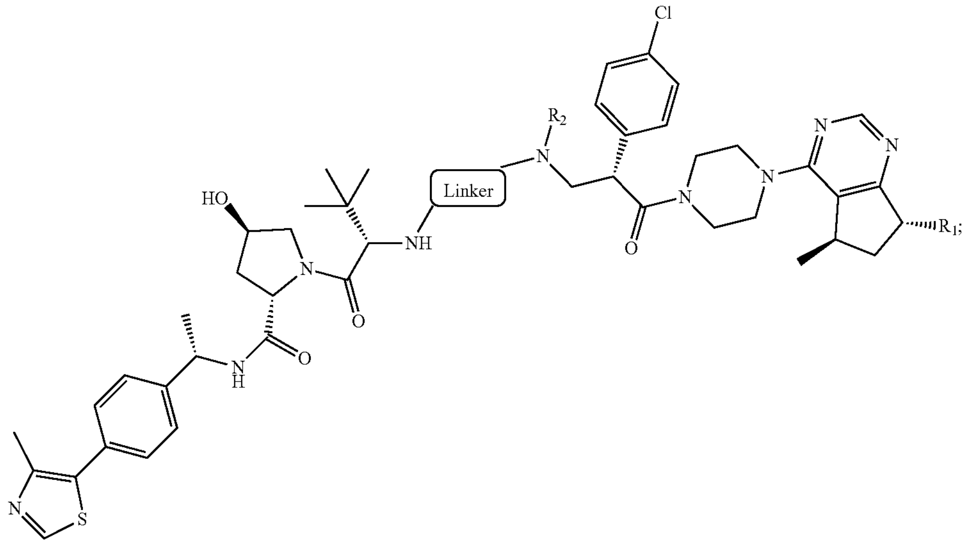
(I-32)
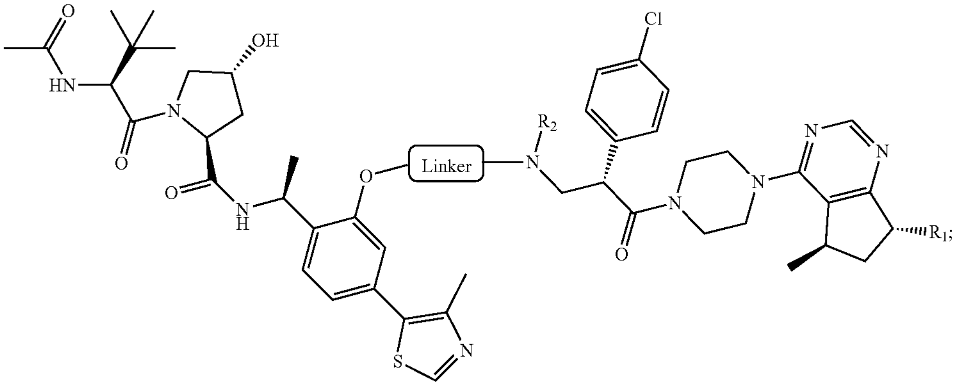

-continued (I-33)

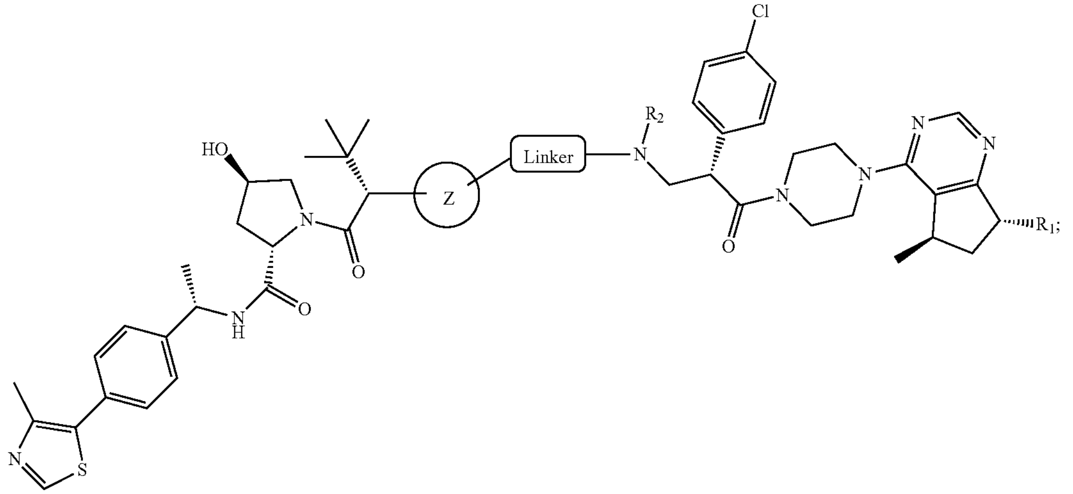

and (I-34)

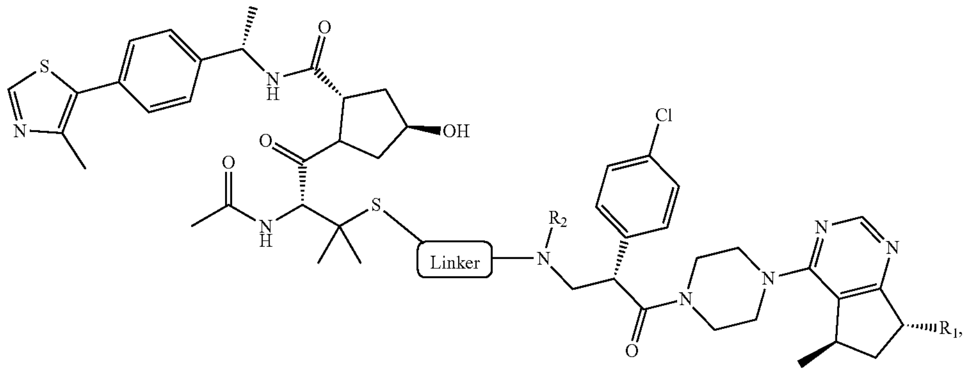

or a pharmaceutically acceptable salt, or stereoisomer thereof, wherein Z is a $C_5$-$C_6$ carbocyclic or heterocyclic group;

$R_1$ is H or OH; and $R_2$ is H, methyl, ethyl, or isopropyl.

Yet other degrons that bind VHL and which may be suitable for use in the present invention are disclosed in U.S. Patent Application Publication 2017/0121321 A1.

Thus, in some embodiments, the compounds of the present invention are represented by any structures generated by the combination of structures TL-1 to TL-4, L1 to L7 and the structures of the degrons described herein, including D1a to D2d, or a pharmaceutically acceptable salts or stereoisomers thereof.

In some embodiments, the present invention provides a compound represented by any of the following structures:

(1)

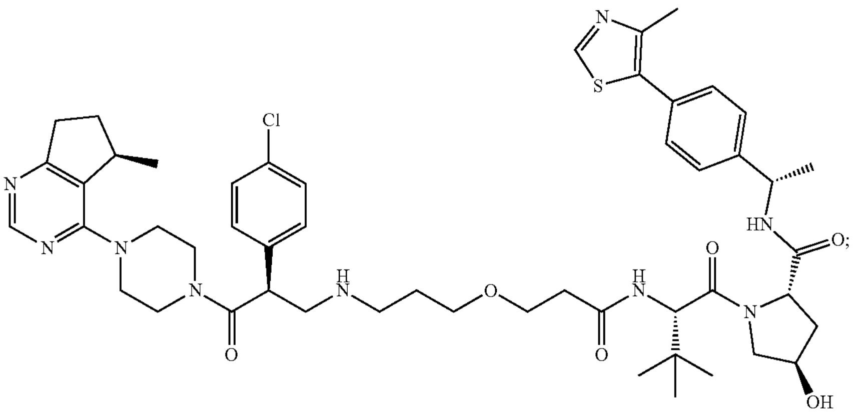

-continued
(2)
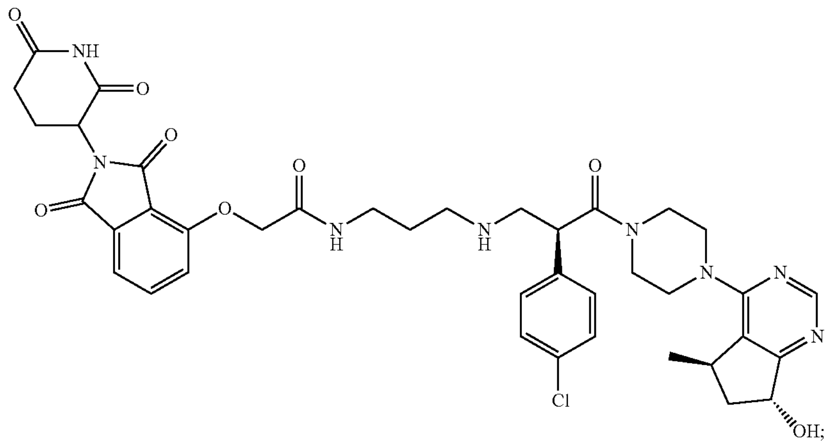
(3)
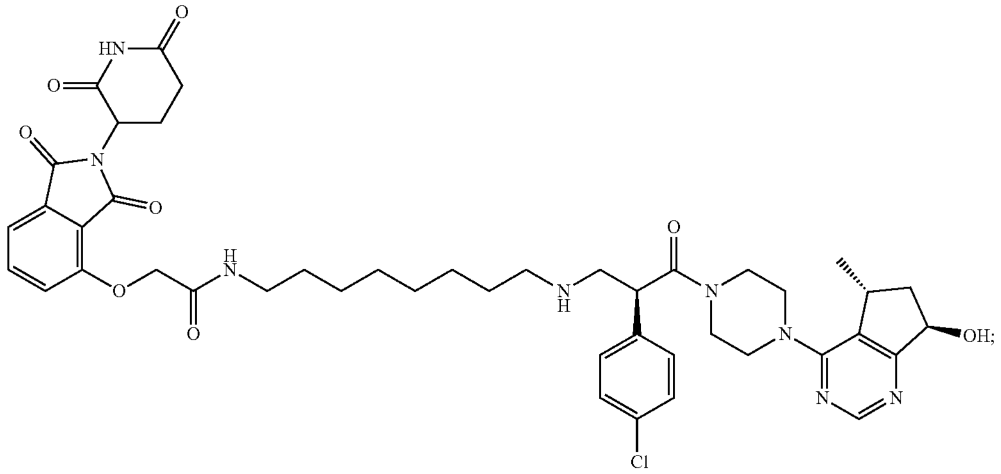
(4)
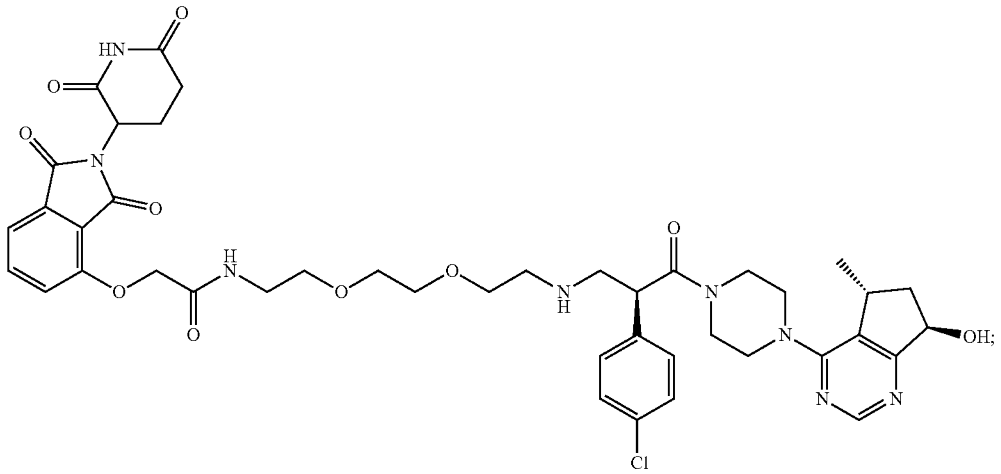

-continued
(5)
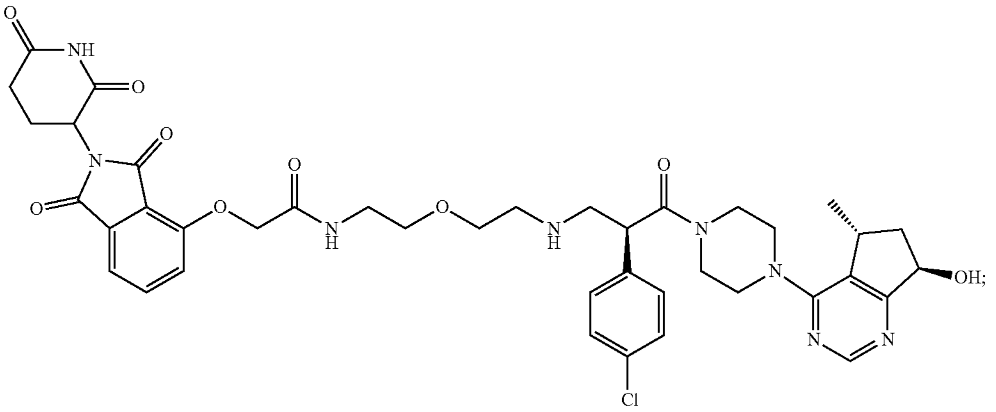
(6)
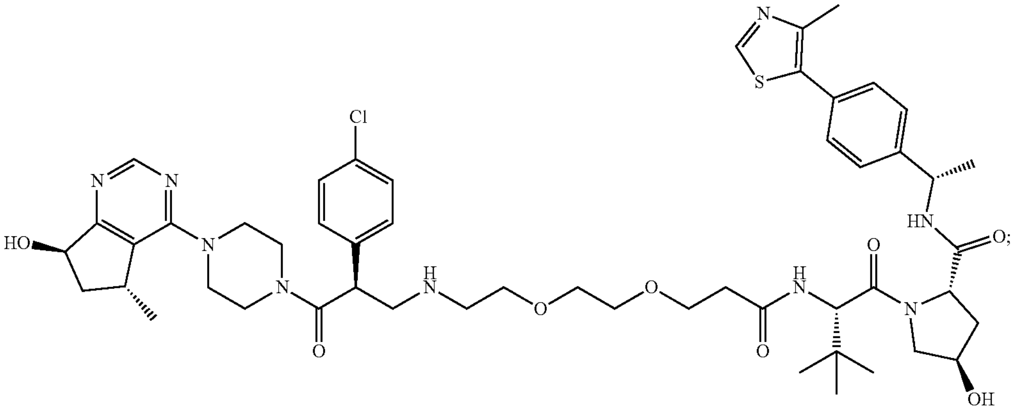
(7)
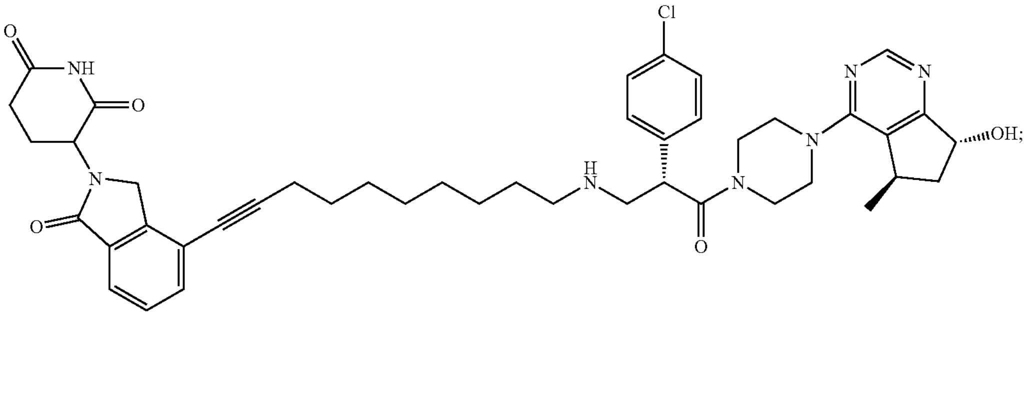
(8)
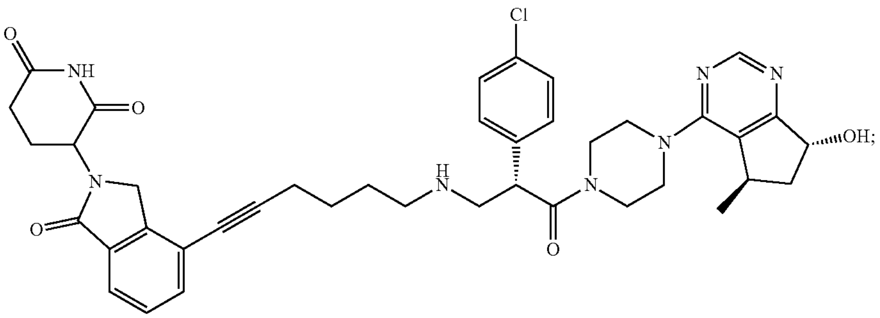

-continued
(9)
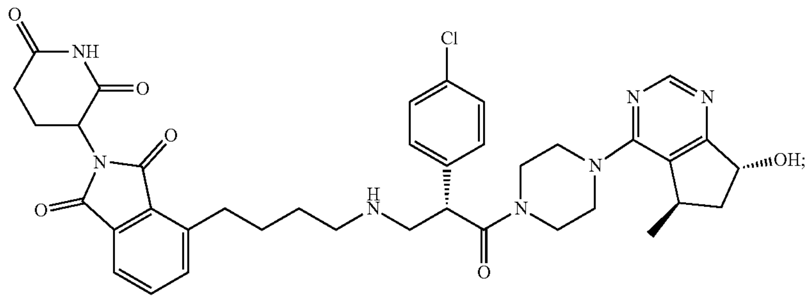
(10)
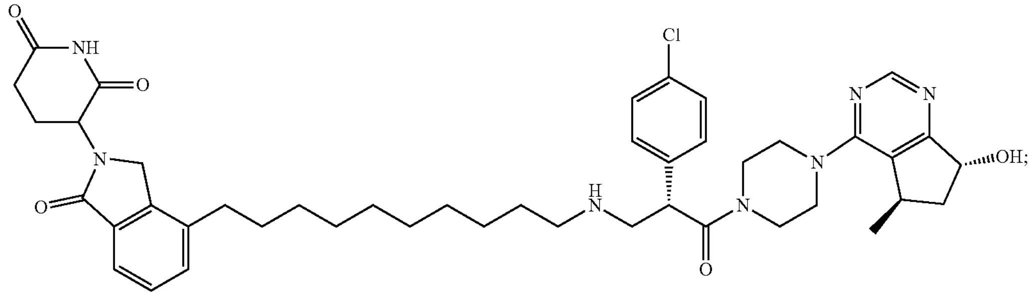
(11)
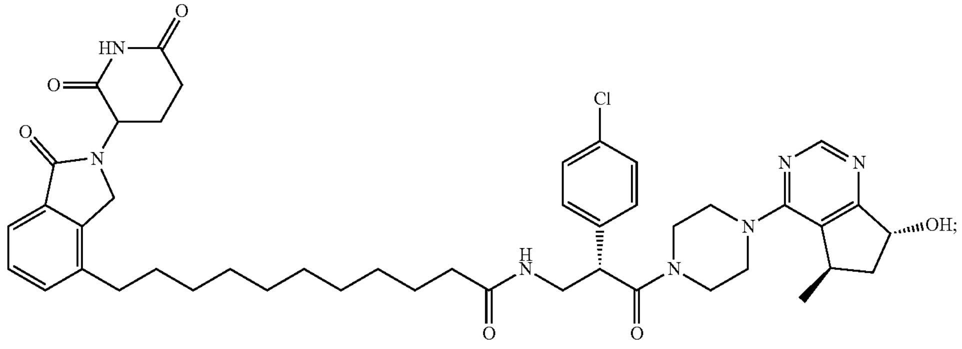
(12)
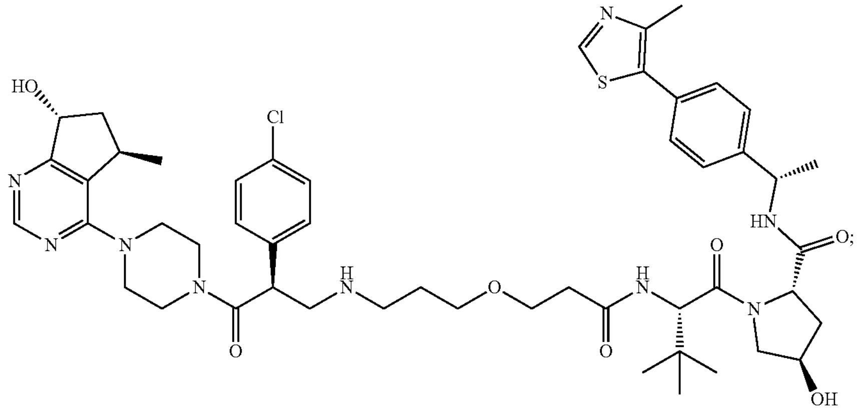

-continued
(13)
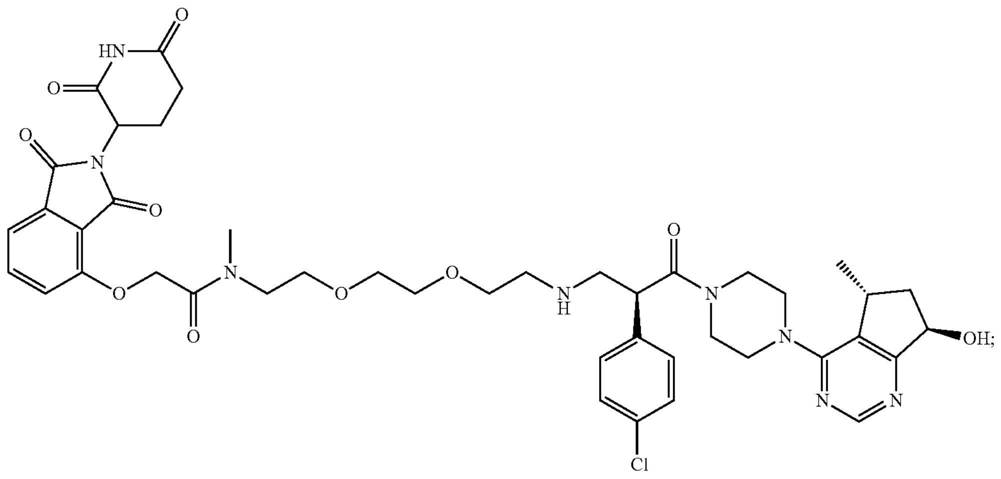
(14)
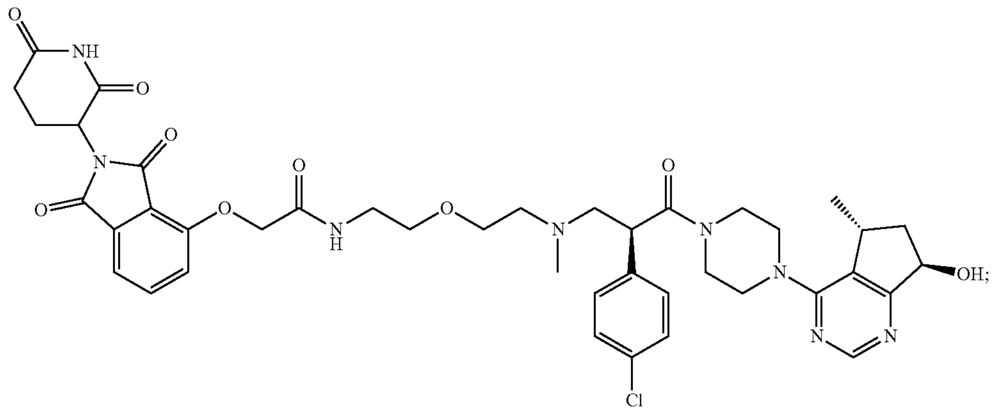
(15)
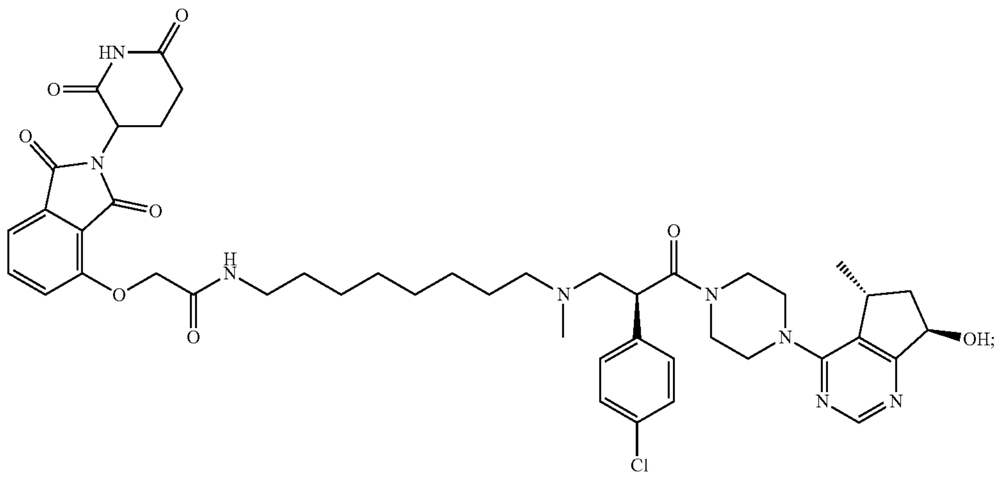

-continued
(16)
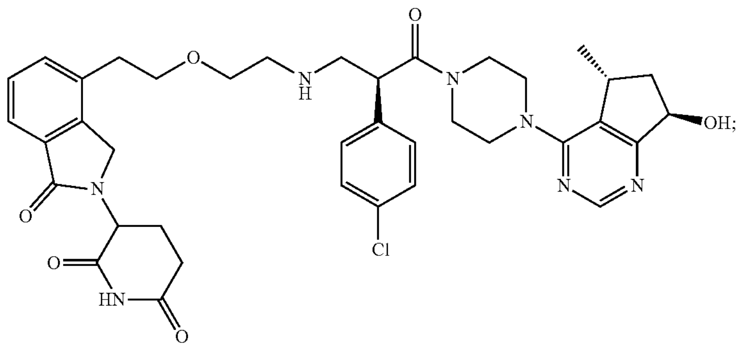
(17)
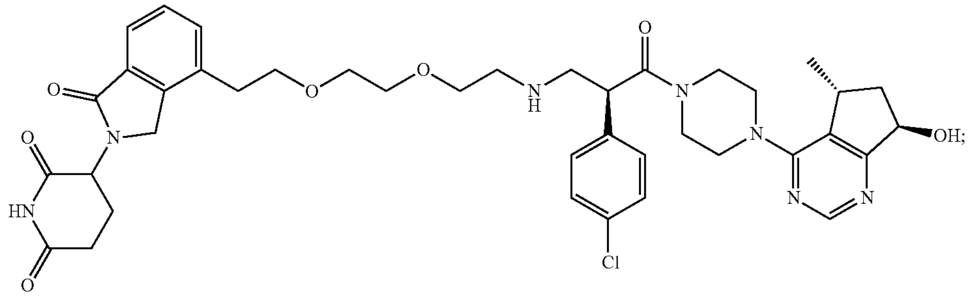
(18)
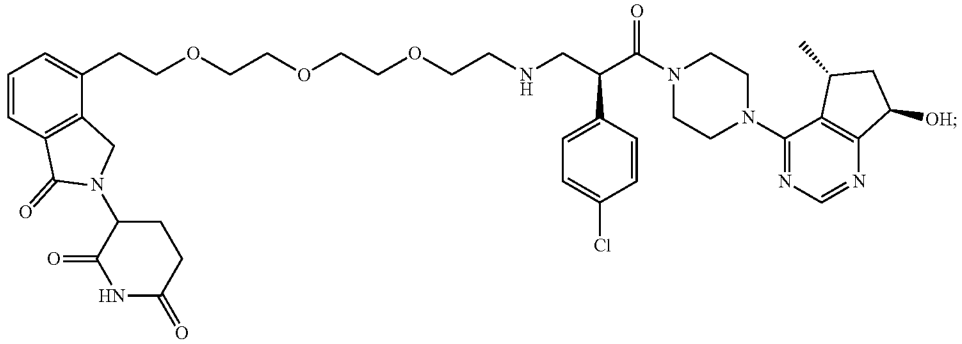
(19)
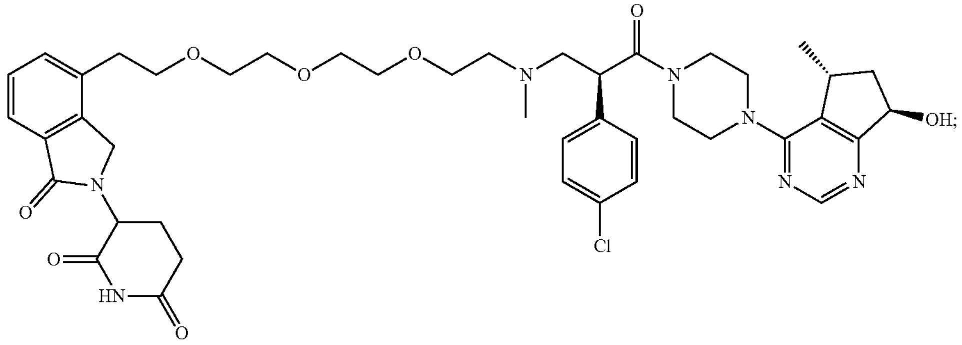

-continued
(20)
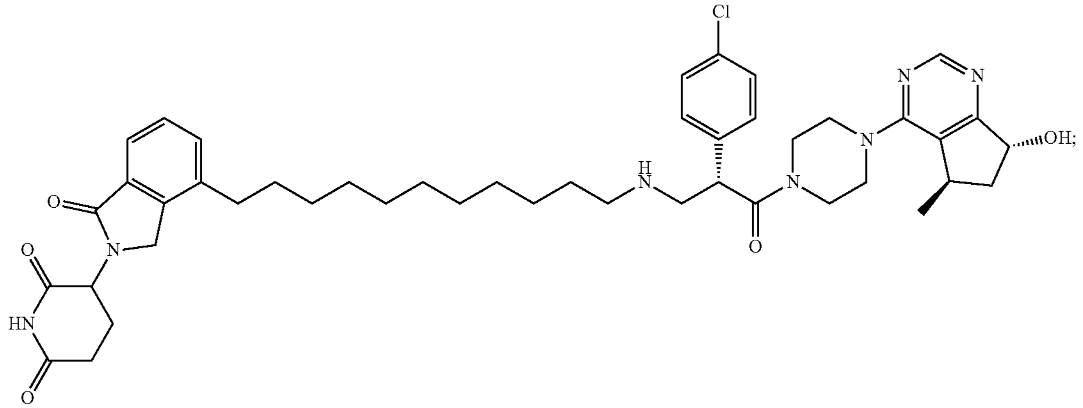
(21)
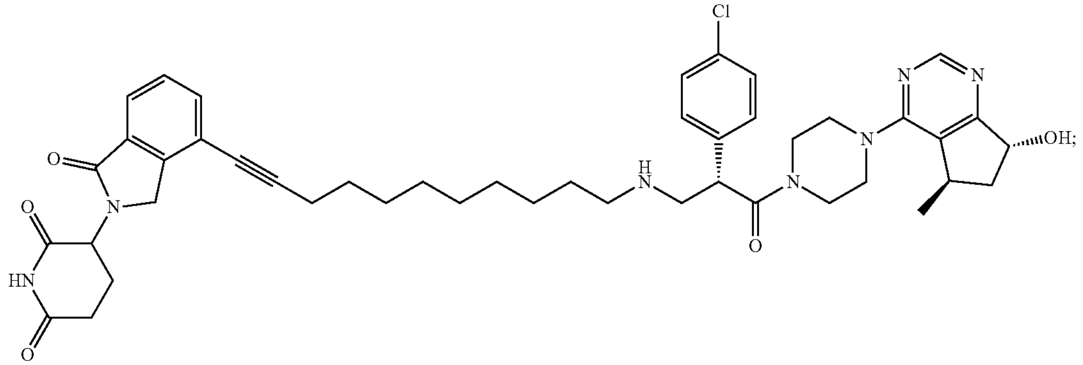
(22)
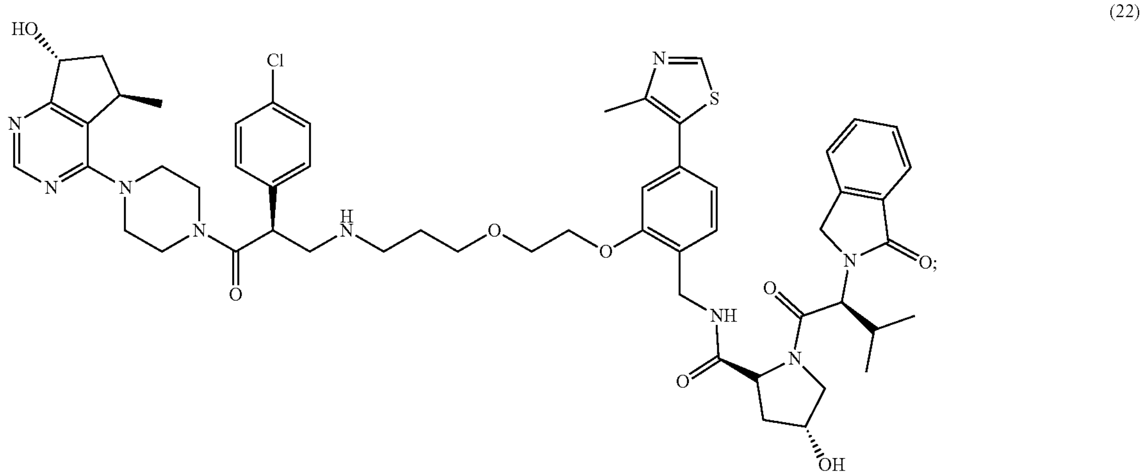
(23)
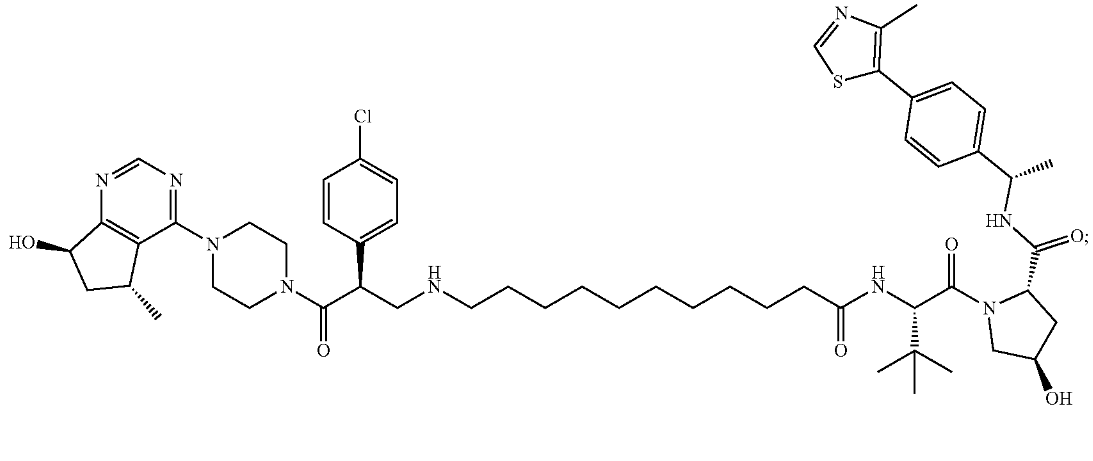

-continued
(24)
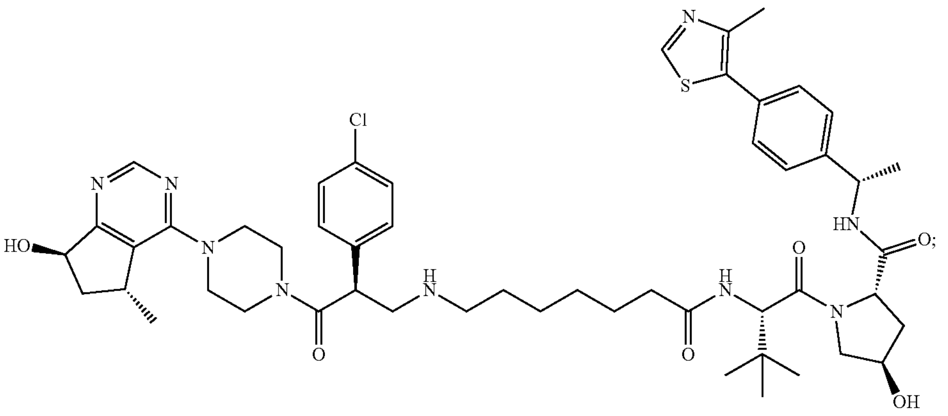
(25)
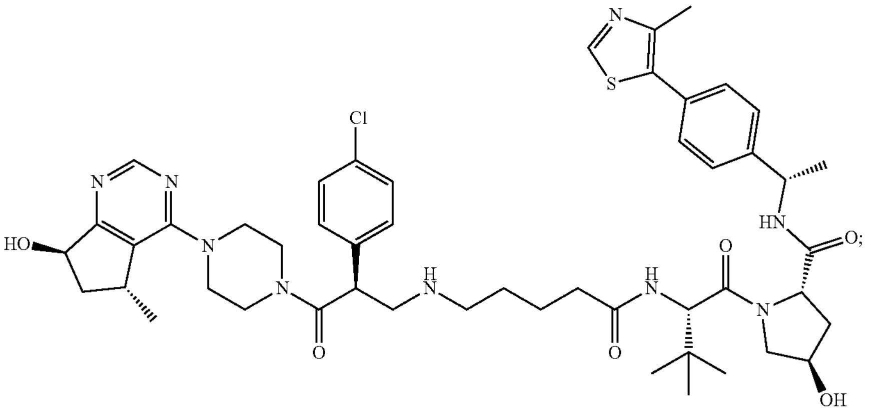
(26)
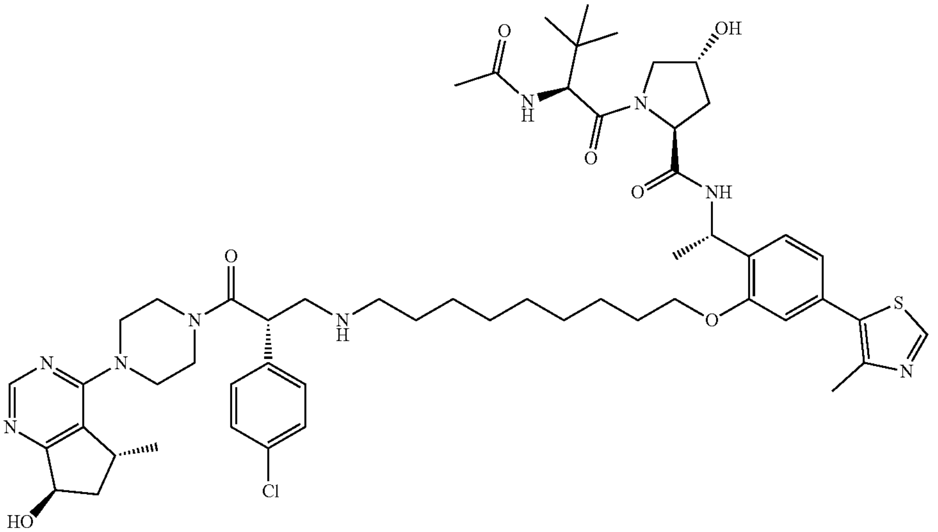
;

-continued (27)

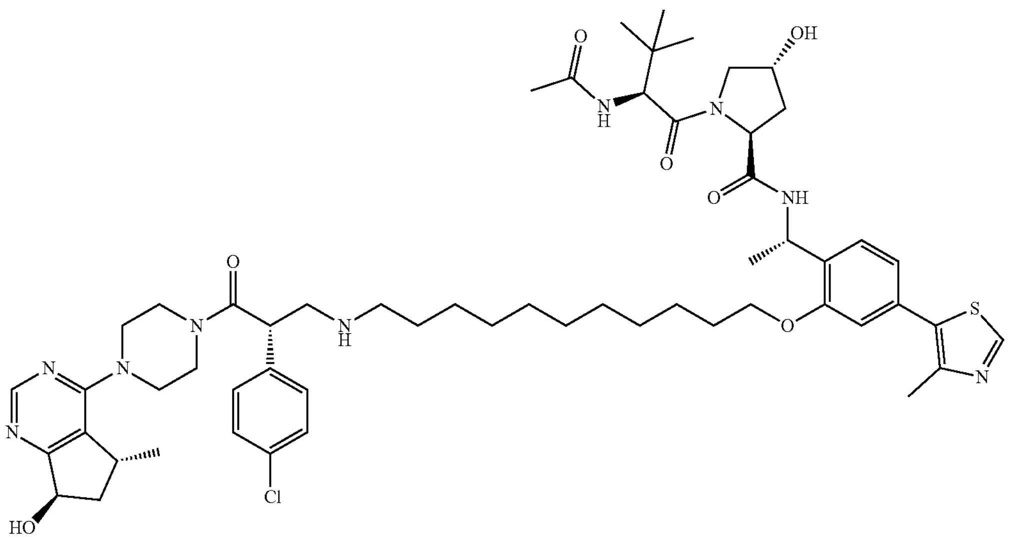

;

(28)

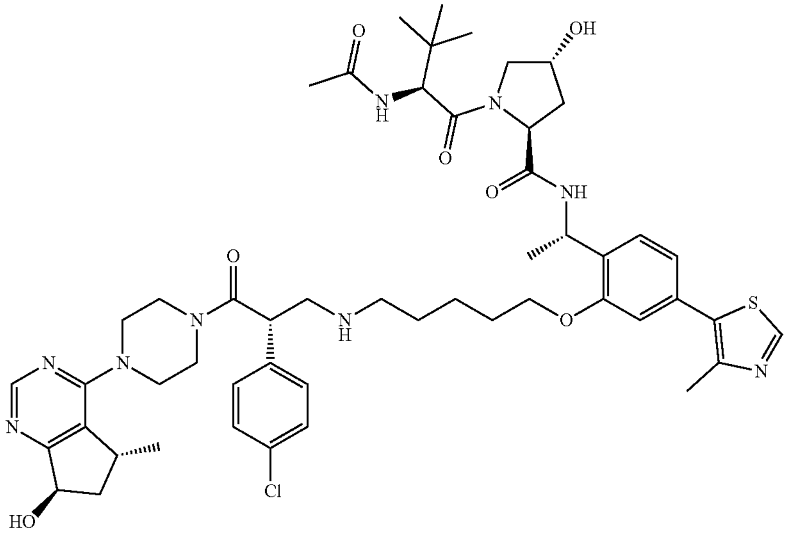

; and (29)

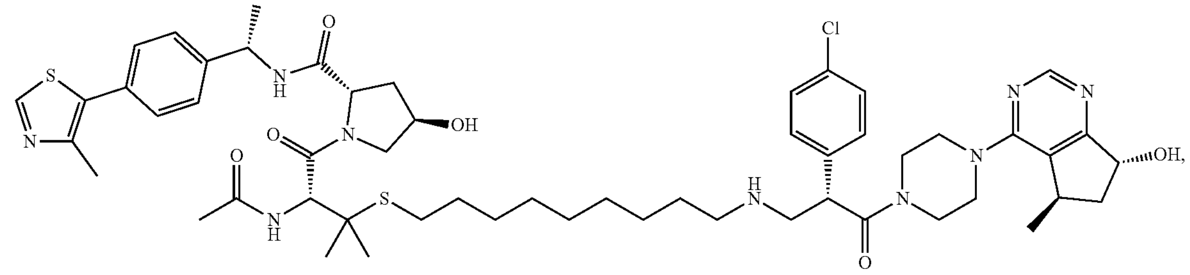

or pharmaceutically acceptable salt and stereoisomer thereof.

Bifunctional compounds of formula I may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the compound of the present invention is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

Bifunctional compounds of formula I may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the bifunctional compounds of formula I may be made and used in the form of individual isomers and substantially free of other isomers, or in the form of a mixture of various isomers, e.g., racemic mixtures of stereoisomers.

In some embodiments, the bifunctional compound of formula I is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

Methods of Synthesis

In some embodiments, the present invention is directed to a method for making a bifunctional compound of formula I or a pharmaceutically acceptable salt or stereoisomer thereof. Broadly, the bifunctional compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a bifunctional compound of formula I or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bifunctional compounds of formula I and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of formula I may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of formula I may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula I may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Bifunctional compounds of formula I may be formulated for buccal or sublingual administration, examples of which include tablets, lozenges and gels.

The bifunctional compounds of formula I may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula I may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term "therapeutically effective amount" refers to an amount of a bifunctional compound of formula I or a pharmaceutically acceptable salt or a stereoisomer thereof, or a composition including a bifunctional compound of formula (I) or a pharmaceutically acceptable salt or a stereoisomer thereof, that is effective in producing the desired therapeutic response in a particular patient suffering from a disease or disorder. The term "therapeutically effective amount" thus includes the amount of the compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amount of AKT1, 2 and 3 in diseased cells.

The total daily dosage of the compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bifunctional compounds of formula I may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. In some embodiments, the total daily dosage may range from 400 mg to 600 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving dysfunctional or dysregulated AKT activity, that entails administration of a therapeutically effective amount of a bifunctional compound of formula I or a pharmaceutically acceptable salt or stereoisomer thereof, to a subject in need thereof.

The diseases or disorders may be said to be characterized or mediated by dysfunctional AKT activity (e.g., elevated levels of AKT or otherwise functionally abnormal AKT relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, compounds of formula I may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g., hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the bifunctional compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, skin, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematological cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the compounds or pharmaceutically acceptable salts or stereoisomers of the present invention are used in the treatment of high-risk neuroblastoma (NB).

In some embodiments, the disease or disorder is acute myeloid leukemia (AML), multiple myeloma (MM), melanoma, rhabdomyosarcoma, or diffuse large B cell lymphoma. In other embodiments, the disease or disorder is small solid tumor. In other embodiments, the disease or disorder is colon cancer, rectal cancer, stomach cancer, breast cancer or pancreatic cancer.

The bifunctional compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

In some embodiments, the compounds or pharmaceutically acceptable salts or stereoisomers of the present invention are used in the treatment of triple-negative breast cancer, alone as mono-therapy or together with a chemotherapeutic agent such as paclitaxel.

The methods of the present invention may entail administration of a bifunctional compound of formula I or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

The bifunctional compounds of formula I may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula I in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bifunctional compound of formula I and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the bifunctional compound of formula I and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the bifunctional compound of formula I may be used in combination with other anti-cancer agents, examples of which include Trametinib (e.g., to treat recurrent and untreated adult acute myeloid leukemia, breast cancer, plasma cell myeloma, endometrial adenocarcinoma, uterine corpus carcinoma, melanoma, cervical cancer), Dabrafenib and Trametinib (e.g., to treat adult solid neoplasm, recurrent colon carcinoma, recurrent melanoma, recurrent ovarian cancer, colon cancer, and skin melanoma), Lapatinib Ditosylate (e.g., to treat estrogen receptor (ER)+/− breast cancer, HER/Neu+breast cancer, Progestrone receptor (PR)+/−breast cancer), GSK1120212 (e.g., to treat proteasome-refractory multiple myeloma, and endometrial and triple negative breast cancer), Selumetinib (e.g., to treat melanoma, gallbladder adenocarcinoma, primary cholangiocellular carcinoma, liver cancer, cholangiocarcinoma of the extrahepatic bile duct, metastatic extrahepatic bile duct cancer, gallbladder cancer, pancreatic acinar cell carcinoma, pancreatic ductal adenocarcinoma, and pancreatic carcinoma), Bendamustine Hydrochloride and Rituximab (e.g., to treat lymphocytic leukemia), Dinaciclib (e.g. to treat pancreatic adenocarcinoma), Hydroxychloroquine (e.g., to treat advanced solid tumors, melanoma, prostate or kidney cancer), Olaparib (e.g., to treat breast cancer and malignant neoplasm), Erlotinib Hydrochloride (e.g., to treat adenosquamous lung carcinoma, bronchioloalveolar carcinoma, large cell lung carcinoma, lung adenocarcinoma, non-small cell lung carcinoma, and squamous cell lung carcinoma), Trastuzumab and Lapatinib Ditosylate (e.g., to treat adenocarcinoma of the gastroesophageal junction, HER2-positive breast cancer, esophageal cancer, gastric cancer), Everolimus (e.g., to treat renal cell cancer), Bicalutamide (e.g., to treat prostate carcinoma), Anastrozole and Goserelin Acetate (e.g., to treat breast cancer), Anastrozole and Fulvestrant (e.g., to treat breast carcinoma), Anastrozole (e.g., to treat ovarian cancer and endometrial cancer), Paclitaxel (e.g., to treat solid neoplasm, ovarian cancer, endometrial cancer, and breast carcinoma), Trametinib and Uprosertib (e.g., to treat uveal melanoma), Bortezomib and Dexamethasone (e.g., to treat multiple myeloma), MK-2206 (e.g., to treat colorectal neoplasms), Paclitaxel and Trastuzumab (e.g., to treat human epidermal growth factor receptor 2 (HER2)-overexpressing solid tumor malignancies), Exemestane and Goserelin (e.g., to treat breast cancer), Gemcitabine (e.g., to treat solid tumors and Non-Hodgkin's Lymphoma), Docetaxel and Prednisolone (e.g., to treat prostate cancer), Carboplatin and Paclitaxel (e.g., to treat platinum-resistant ovarian cancer, endometrial cancer), Gefitinib (e.g., to treat non-small cell lung cancer), Carboplatin (e.g., to treat ovarian cancer), Cobimetinib (e.g., to treat neoplasms), Fulvestrant (e.g., to treat breast cancer), and Oxaliplatin, 5-Fluorouracil, and Leucovorin (modified FOLFOX6 [mFOLFOX6] e.g., to treat advanced or metastatic gastric or gastroesophageal junction (GEJ) cancer).

Pharmaceutical Kits

The present bifunctional compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of formula I or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of (2S,4R)-1-((S)-2-(3-(3-(((S)-2-(4-chlorophenyl)-3-(4-((R)-5-methyl-6,7-dihydro-5H-cyclopenta[d]pyrimidin-4-yl)piperazin-1-yl)-3-oxopropyl)amino) propoxy)propanamido)-3,3-dimethylbutanoyl)-4-hydroxy-N—((S)-1-(4-(4-methylthiazol-5-yl) phenyl)ethyl)pyrrolidine-2-carboxamide (1)

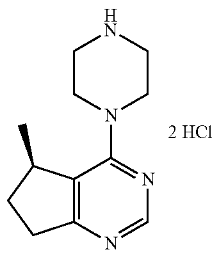 [SMILES: C[C@@H]1CCc2ncnc(N3CCNCC3)c21]

(R)-5-Methyl-4-(piperazin-1-yl)-6,7-dihydro-5H-cyclopenta[d]pyrimidine Dihydrochloride Salt To a solution of 1,4-dioxane (2.7 mL) and DCM (300 μL) was added tert-butyl (R)-4-(5-methyl-6,7-dihydro-5H-cyclopenta[d]pyrimidin-4-yl)piperazine-1-carboxylate (250 mg, 0.79 mmol) and 4 M HCl in 1,4-dioxane (1 mL). The reaction was stirred for 5 hours. The reaction mixture was concentrated in vacuo to obtain crude (R)-5-methyl-4-(piperazin-1-yl)-6,7-dihydro-5H-cyclopenta[d]pyrimidine dihydrochloride as a pale tan solid (230 mg, quantitative yield), which was used without further purification.

MS m/z 219.16 $[M+H]^+$

Scheme 1. Synthesis of compound 1.

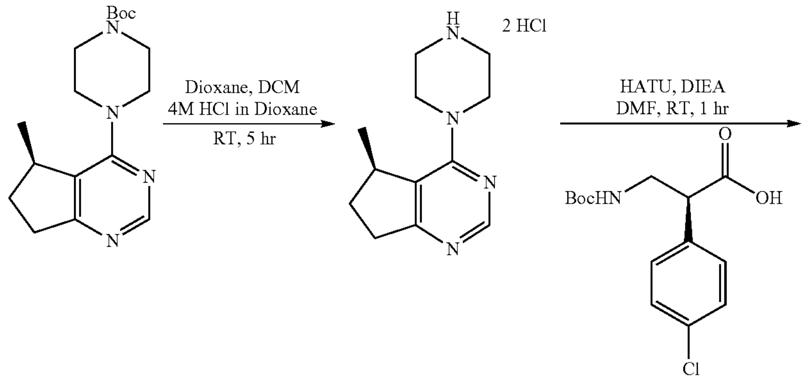

-continued
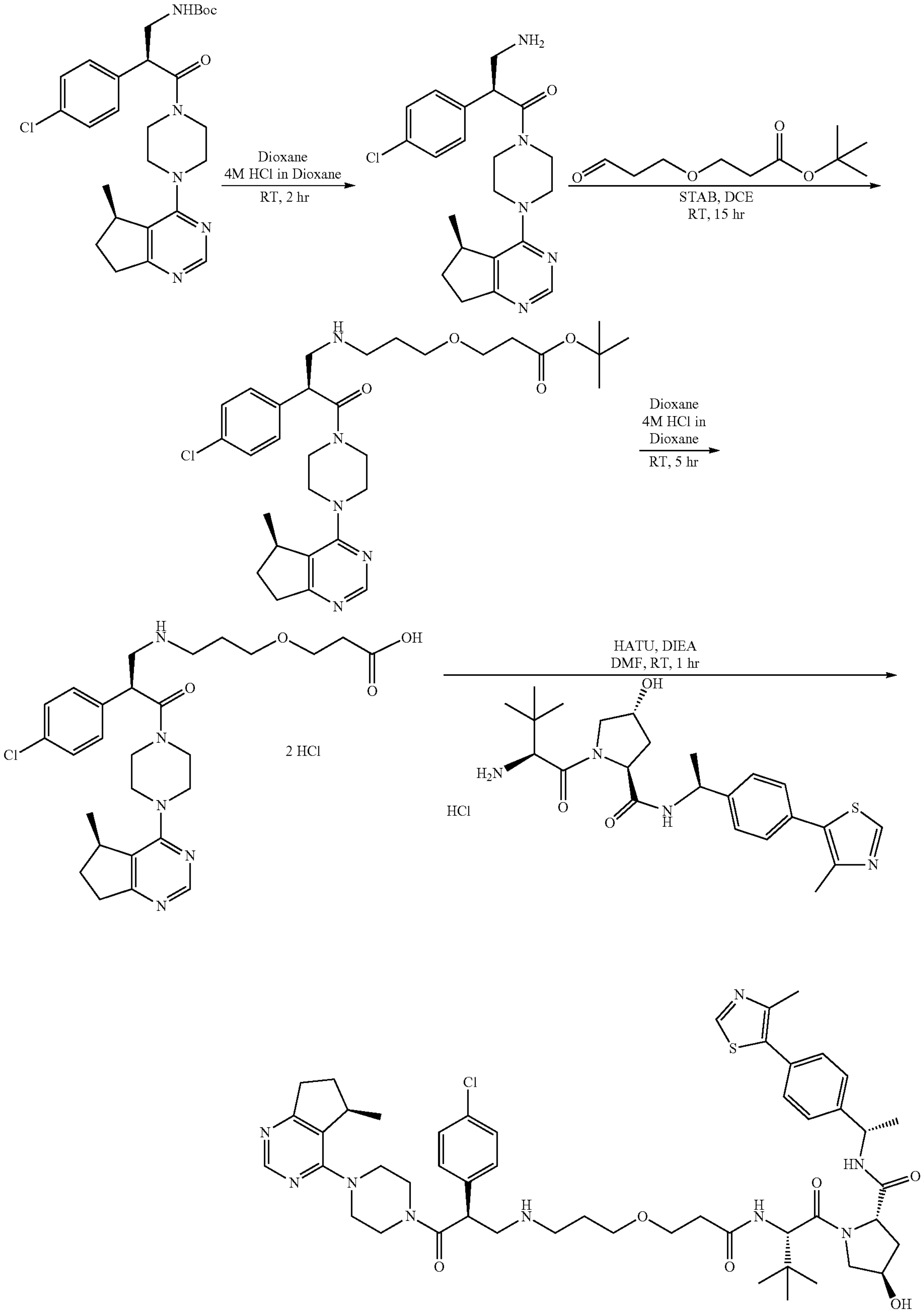
1

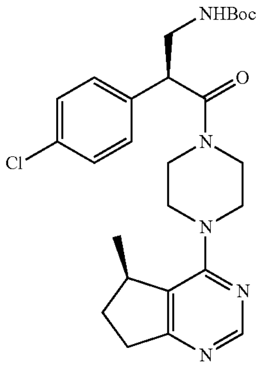 [SMILES: C[C@@H]1CCc2ncnc(N3CCN(C(=O)[C@H](CNC(=O)OC(C)(C)C)c4ccc(Cl)cc4)CC3)c21]

tert-Butyl ((S)-2-(4-chlorophenyl)-3-(4-((R)-5-methyl-6,7-dihydro-5H-cyclopenta[d]-pyrimidin-4-yl)piperazin-1-yl)-3-oxopropyl)carbamate To a solution of (R)-5-methyl-4-(piperazin-1-yl)-6,7-dihydro-5H-cyclopenta-[d]pyrimidine dihydrochloride (230 mg, 0.79 mmol), (S)-3-((tert-butoxycarbonyl)amino)-2-(4-chlorophenyl)propanoic acid (260 mg, 0.87 mmol), and 1-[bis(dimethylamino)methylene]-1H-1,2,3-triazolo[4,5-b] pyridinium3-oxid hexafluoro-phosphate (HATU) (299 mg, 0.79 mmol) in DMF (5.5 mL) was added N,N-diisopropylethylamine (DIEA) (686 μL, 3.93 mmol). The reaction was stirred for 1 hour. The reaction was diluted with ethyl acetate and washed with brine (10 mL×4). The pooled organic layers were dried with anhydrous sodium sulfate, and concentrated in vacuo. The crude residue was purified by column chromatography on silica gel (0-10% MeOH in DCM) to give tert-butyl ((S)-2-(4-chlorophenyl)-3-(4-((R)-5-methyl-6,7-dihydro-5H-cyclopenta[d]pyrimi-din-4-yl) piperazin-1-yl)-3-oxopropyl)carbamate (375 mg, 95% yield) as a yellow oil.

MS m/z 500.26 $[M+H]^+$.

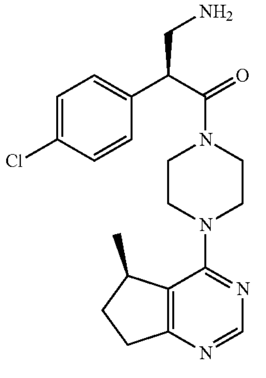 [SMILES: C[C@@H]1CCc2ncnc(N3CCN(C(=O)[C@H](CN)c4ccc(Cl)cc4)CC3)c21]

(S)-3-Amino-2-(4-chlorophenyl)-1-(4-((R)-5-methyl-6,7-dihydro-5H-cyclopenta[d]-pyrimidin-4-yl)piperazin-1-yl)propan-1-one To a solution of tert-butyl ((S)-2-(4-chlorophenyl)-3-(4-((R)-5-methyl-6,7-dihydro-5H-cyclopenta[d]pyrimidin-4-yl)piperazin-1-yl)-3-oxopropyl)carbamate (375 mg, 0.75 mmol) in 1,4-dioxane (4 mL) was added 4 M HCl in 1,4-dioxane (1.5 mL). The reaction was stirred for 2 hours. The reaction mixture was concentrated in vacuo. The crude residue was dissolved in 4:1 chloroform:isopropanol and washed with aqueous (aq.) saturated (sat.) $NaHCO_3$. The organic layer was extracted with 4:1 chloroform:isopropanol (20 mL×3), dried over anhydrous sodium sulfate, and concentrated in vacuo. Crude (S)-3-amino-2-(4-chlorophenyl)-1-(4-((R)-5-methyl-6,7-dihydro-5H-cyclopenta[d]pyrimi-din-4-yl)piperazin-1-yl)propan-1-one (299 mg, quantitative yield) was obtained as a yellow foam.

MS m/z 400.20 $[M+H]^+$.

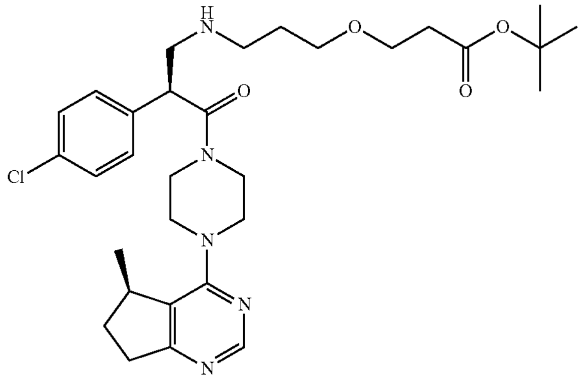 [SMILES: C[C@@H]1CCc2ncnc(N3CCN(C(=O)[C@H](CNCCCOCCC(=O)OC(C)(C)C)c4ccc(Cl)cc4)CC3)c21]

tert-Butyl 3-(3-(((S)-2-(4-chlorophenyl)-3-(4-((R)-5-methyl-6,7-dihydro-5H-cyclopenta[d]-pyrimidin-4-yl)piperazin-1-yl)-3-oxopropyl)amino)propoxy)propanoate To (S)-3-amino-2-(4-chlorophenyl)-1-(4-((R)-5-methyl-6,7-dihydro-5H-cyclopenta[d]pyrimidin-4-yl)piperazin-1-yl)propan-1-one (74 mg, 0.19 mmol) and tert-butyl 3-(3-oxopropoxy)propanoate (29 mg, 0.14 mmol) was added dichloroethane (DCE) (3.8 mL) and the reaction was stirred at room temperature for 20 minutes. Sodium triacetoxyborohydride (STAB) (60 mg, 0.28 mmol) was added in one portion and the reaction was stirred for 15 hours. The reaction was quenched with sat. $NaHCO_3$ (aq) and extracted with 4:1 chloroform:isopropanol (10 mL×3). The crude was purified by column chromatography on silica gel (0-20% MeOH in DCM) to obtain tert-butyl 3-(3-(((S)-2-(4-chlorophenyl)-3-(4-((R)-5-methyl-6,7-dihydro-5H-cyclopenta[d] pyrimidin-4-yl)piperazin-1-yl)-3-oxopropyl)amino)-propoxy)propanoate (27 mg, 32% yield) as a yellow oil.

MS m/z 586.35 $[M+H]^+$.

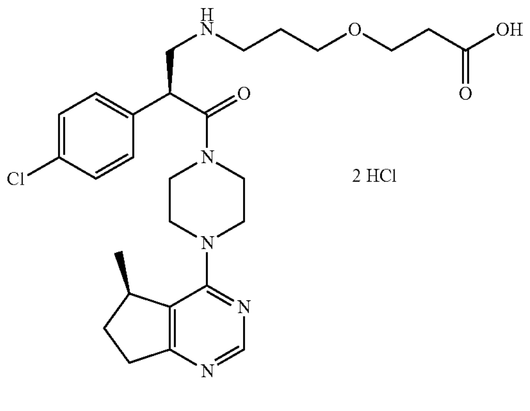 [SMILES: C[C@@H]1CCc2ncnc(N3CCN(C(=O)[C@H](CNCCCOCCC(=O)O)c4ccc(Cl)cc4)CC3)c21]

3-(3-(((S)-2-(4-Chlorophenyl)-3-(4-((R)-5-methyl-6,7-dihydro-5H-cyclopenta[d]pyrimidin-4-yl)piperazin-1-yl)-3-oxopropyl)amino)propoxy)propanoic Acid Dihydrochloride Salt To tert-butyl 3-(3-(((S)-2-(4-chlorophenyl)-3-(4-((R)-5-methyl-6,7-dihydro-5H-cyclopenta[d]pyrimidin-4-yl)piperazin-1-yl)-3-oxopropyl)amino)propoxy)propanoate (27 mg, 0.05 mmol) was added 1,4-dioxane (750 μL) and 4 M HCl in 1,4-dioxane (250 μL). The reaction was stirred for 5 hours. The reaction mixture was concentrated in vacuo to obtain crude 3-(3-(((S)-2-(4-chlorophenyl)-3-(4-((R)-5-methyl-6,7-dihydro-5H-cyclopenta[d]pyrimidin-4-yl)piperazin-1-yl)-3-oxopropyl)amino)propoxy)propanoic acid (22 mg, 79% yield) as the dihydrochloride salt.

MS m/z 530.30 $[M+H]^+$.

(1)

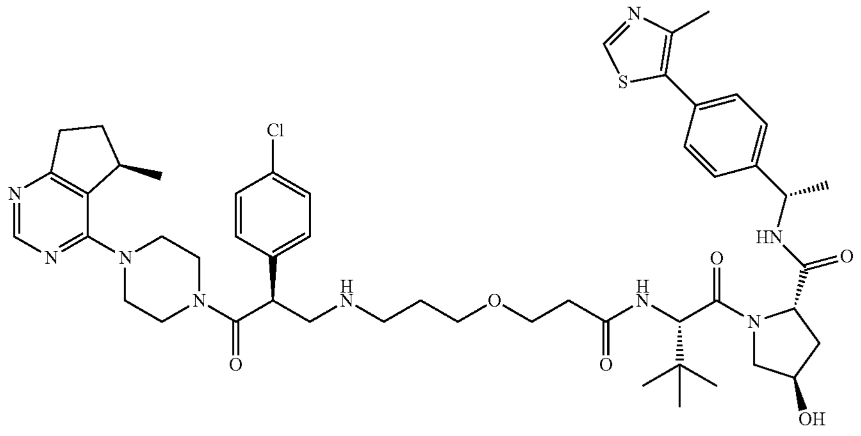

To 3-(3-(((S)-2-(4-chlorophenyl)-3-(4-((R)-5-methyl-6,7-dihydro-5H-cyclopenta[d]-pyrimidin-4-yl)piperazin-1-yl)-3-oxopropyl)amino)propoxy)propanoic acid dihydrochloride (22 mg, 0.03 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (16 mg, 0.03 mmol), and HATU (13 mg, 0.03 mmol) was added DMF (1 mL) and DIEA (35 μL, 0.2 mmol). The reaction was stirred for 1 hour and purified by reverse phase HPLC (25-85% MeOH in $H_2O$) to obtain compound 1 as an off-white solid (3.5 mg, 11% yield).

1H NMR (500 MHz, DMSO-$d_6$) δ 8.91 (d, J=1.7 Hz, 1H), 8.32-8.26 (m, 2H), 7.83 (d, J=9.3 Hz, 1H), 7.43-7.39 (m, 2H), 7.38-7.35 (m, 2H), 7.32-7.28 (m, 4H), 5.06 (s, 1H), 4.85 (q, J=7.1 Hz, 1H), 4.47 (d, J=2.1 Hz, 1H), 4.36 (t, J=12.7 Hz, 2H), 4.21 (s, 1H), 3.67-3.58 (m, 2H), 3.51 (ddt, J=15.7, 9.0, 4.9 Hz, 6H), 3.39 (dtd, J=18.9, 9.4, 4.0 Hz, 6H), 2.97 (d, J=11.2 Hz, 2H), 2.86 (s, 2H), 2.75 (dt, J=17.1, 8.4 Hz, 1H), 2.66-2.60 (m, 1H), 2.51-2.45 (m, 1H), 2.38 (d, J=1.5 Hz, 3H), 2.29 (dt, J=14.7, 6.0 Hz, 2H), 2.11 (dq, J=12.7, 8.6 Hz, 2H), 1.95 (t, J=10.5 Hz, 1H), 1.73 (tt, J=8.3, 4.7 Hz, 3H), 1.51 (ddt, J=12.9, 8.6, 4.1 Hz, 1H), 1.30 (d, J=7.0 Hz, 3H), 0.97 (d, J=6.7 Hz, 3H), 0.86 (s, 9H).

MS m/z 956.51 $[M+H]^+$.

Example 2: Synthesis of Synthesis of N-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)-amino)propyl)-2-((2-(2,6-dioxopiperidin-3-yl)-1,3-dioxoisoindolin-4-yl)oxy) acetamide (2)

Scheme 2. Synthesis of intermediate 1 (Int-1).

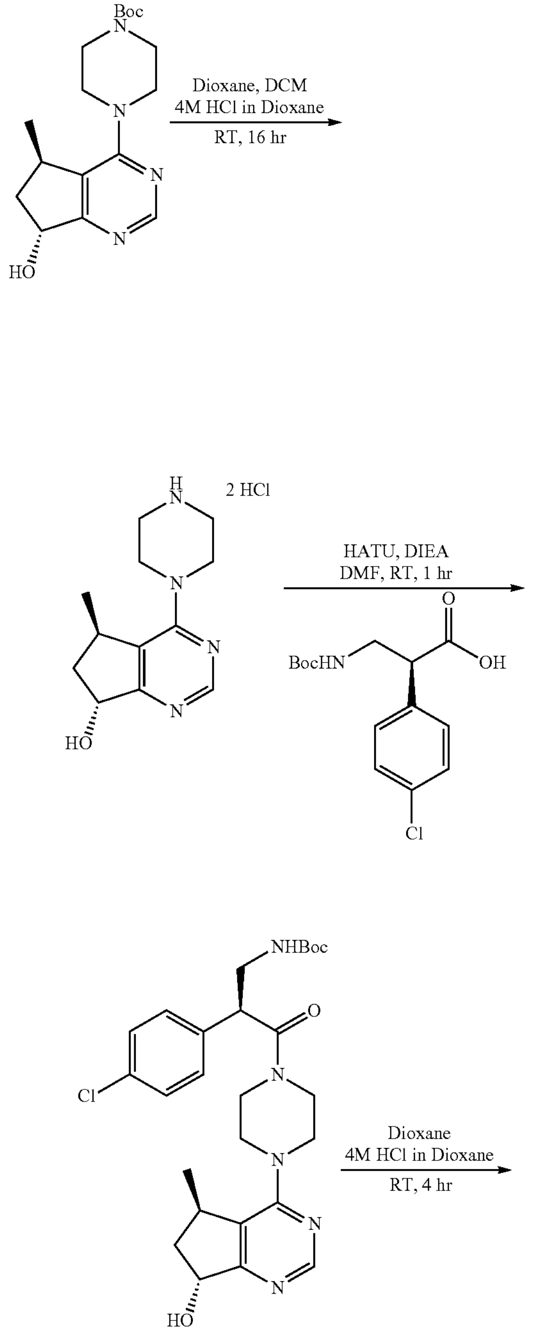

-continued

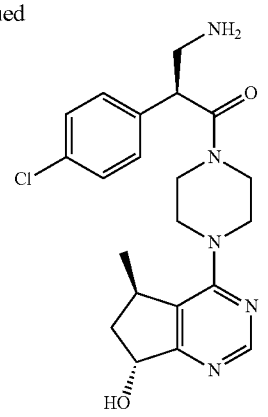

Int-1

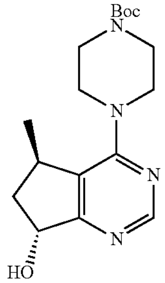 [SMILES: C[C@@H]1C[C@@H](O)c2ncnc(N3CCN(C(=O)OC(C)(C)C)CC3)c21]

tert-Butyl 4-((5R,7R)-7-hydroxy-5-methyl-6,7-dihydro-5H-cyclopenta[d]pyrimidin-4-yl)-piperazine-1-carboxylate The starting material tert-butyl 4-((5R,7R)-7-hydroxy-5-methyl-6,7-dihydro-5H-cyclopenta[d]pyrimidin-4-yl)piperazine-1-carboxylate was prepared following the procedures reported in WO2008006032A1.

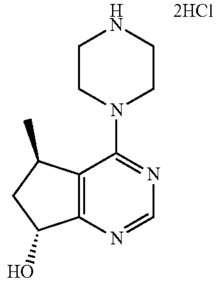 [SMILES: C[C@@H]1C[C@@H](O)c2ncnc(N3CCNCC3)c21]

(5R,7R)-5-Methyl-4-(piperazin-1-yl)-6,7-dihydro-5H-cyclopenta[d]pyrimidin-7-ol Dihydrochloride Salt To a solution of tert-butyl 4-((5R,7R)-7-hydroxy-5-methyl-6,7-dihydro-5H-cyclopenta[d]pyrimidin-4-yl)piperazine-1-carboxylate (426 mg, 1.27 mmol) in 1,4-dioxane (7.5 mL) and DCM (1 mL) was added 4 M HCl in 1,4-dioxane (2.5 mL). The reaction was stirred for 16 hours. The reaction mixture was concentrated in vacuo to obtain crude (5R,7R)-5-methyl-4-(piperazin-1-yl)-6,7-dihydro-5H-cyclopenta[d]pyrimidin-7-ol (373 mg, quantitative yield) as a dihydrochloride salt.

MS m/z 235.21 [M+H]$^+$.

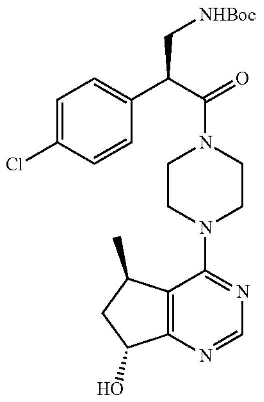 [SMILES: C[C@@H]1C[C@@H](O)c2ncnc(N3CCN(C(=O)[C@H](CNC(=O)OC(C)(C)C)c4ccc(Cl)cc4)CC3)c21]

tert-Butyl ((S)-2-(4-chlorophenyl)-3-(4-((5R,7R)-7-hydroxy-5-methyl-6,7-dihydro-5H-cyclo-penta[d]pyrimidin-4-yl)piperazin-1-yl)-3-oxopropyl)carbamate To a solution of (5R,7R)-5-methyl-4-(piperazin-1-yl)-6,7-dihydro-5H-cyclopenta[d]pyrimidin-7-ol dihydrochloride (277 mg, 0.9 mmol), (S)-3-((tert-butoxycarbonyl)-amino)-2-(4-chlorophenyl)propanoic acid (270 mg, 0.9 mmol), and HATU (343 mg, 0.9 mmol) in DMF (9 mL) was added DIEA (784 µL, 4.5 mmol). The reaction was stirred for 1 hour. The reaction mixture was diluted with ethyl acetate, and washed with brine (15 mL×4). The pooled organic layers were dried over anhydrous sodium sulfate, and concentrated in vacuo. The crude residue was purified by column chromatography on silica gel (0-15% MeOH in DCM) to obtain tert-butyl ((S)-2-(4-chlorophenyl)-3-(4-((5R,7R)-7-hydroxy-5-methyl-6,7-dihydro-5H-cyclopen-ta[d]pyrimidin-4-yl)piperazin-1-yl)-3-oxopropyl)carbamate (430 mg, 93% yield) as a white foam.

MS m/z 516.25 [M+H]$^+$.

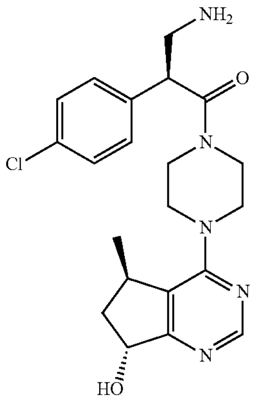 [SMILES: C[C@@H]1C[C@@H](O)c2ncnc(N3CCN(C(=O)[C@H](CN)c4ccc(Cl)cc4)CC3)c21]

(S)-3-Amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one (Int-1)

To a solution of tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)carbamate (430 mg, 0.83 mmol) in 1,4-dioxane (3 mL) was added 4 M HCl in 1,4-dioxane (1 mL). The reaction was stirred for 4 hours. The reaction mixture was concentrated in vacuo. The crude residue was dissolved in 4:1 chloroform:isopropanol and washed with sat. $NaHCO_3$ (aq). The organic layer was extracted with 4:1 chloroform:isopropanol (20 mL×3), dried over anhydrous sodium sulfate, and concentrated in vacuo. Crude (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one (332 mg, quantitative yield) was obtained as a tan foam.

MS m/z 416.20 [M+H]$^+$.

Scheme 3. Synthesis of compound 2 from Int-1.

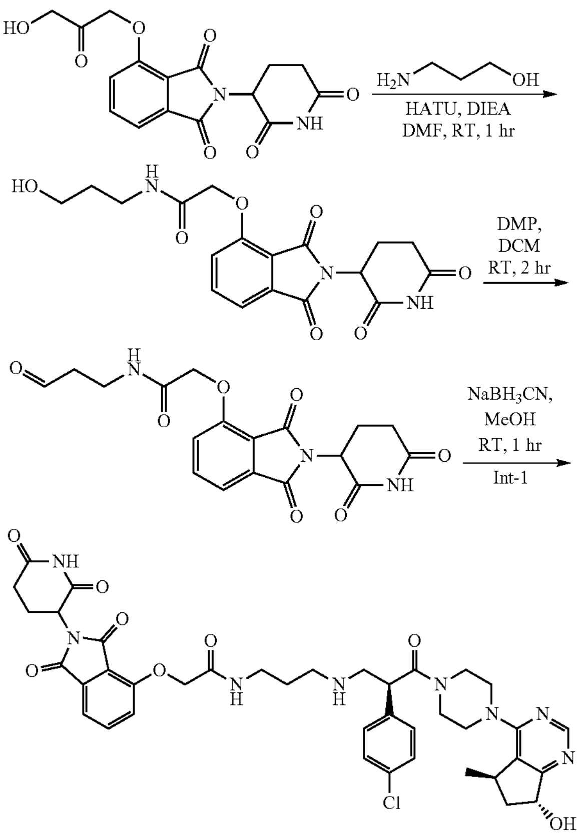

2

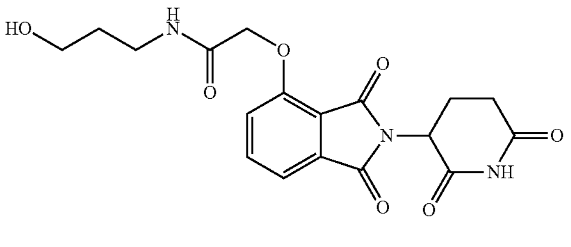 [SMILES: O=C(COc1cccc2c1C(=O)N(C1CCC(=O)NC1=O)C2=O)NCCCO]

2-((2-(2,6-Dioxopiperidin-3-yl)-1,3-dioxoisoindolin-4-yl)oxy)-N-(3-hydroxypropyl)acetamide To a solution of 2-((2-(2,6-dioxopiperidin-3-yl)-1,3-dioxoisoindolin-4-yl)oxy)acetic acid (100 mg, 0.3 mmol), 3-aminopropan-1-ol (23 mg, 0.3 mmol), and HATU (114 mg, 0.3 mmol) in DMF (3 mL) was added DIEA (160 μL, 0.9 mmol). The reaction was stirred for 1 hour and purified by reverse phase HPLC (10-75% MeOH in $H_2O$) to obtain 2-((2-(2,6-dioxopiperidin-3-yl)-1,3-dioxoisoindolin-4-yl)oxy)-N-(3-hydroxypropyl)acetamide as a white solid (78 mg, 66% yield).

MS m/z 390.16 $[M+H]^+$.

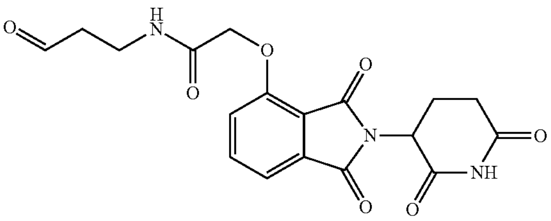 [SMILES: O=CCCNC(=O)COc1cccc2c1C(=O)N(C1CCC(=O)NC1=O)C2=O]

2-((2-(2,6-Dioxopiperidin-3-yl)-1,3-dioxoisoindolin-4-yl)oxy)-N-(3-oxopropyl)acetamide To a solution of 2-((2-(2,6-dioxopiperidin-3-yl)-1,3-dioxoisoindolin-4-yl)oxy)-N-(3-hydroxypropyl)acetamide (60 mg, 0.15 mmol) in DCM (6 mL) was added Dess-Martin periodinane (DMP) (131 mg, 0.31 mmol). The reaction was stirred for 2 hours. The reaction mixture was filtered and concentrated in vacuo to obtain crude 2-((2-(2,6-dioxopiperidin-3-yl)-1,3-dioxoisoindolin-4-yl)oxy)-N-(3-oxopropyl)acetamide (60 mg, quantitative yield) as a yellow solid.

MS m/z 388.12 $[M+H]^+$.

(2)

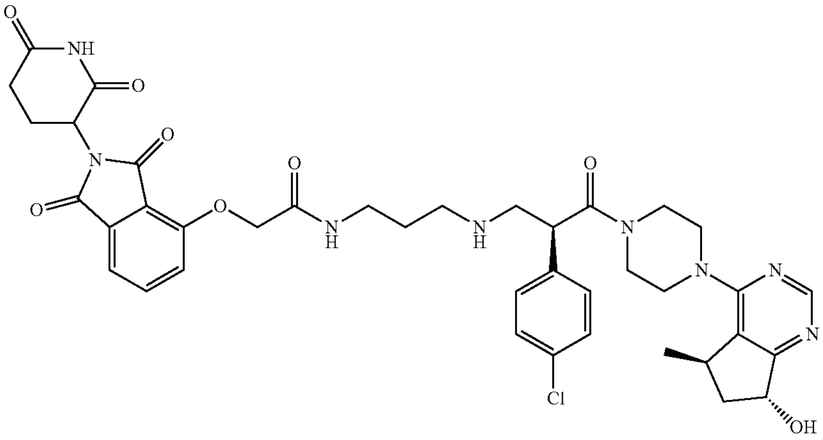

To 2-((2-(2,6-dioxopiperidin-3-yl)-1,3-dioxoisoindolin-4-yl)oxy)-N-(3-oxopropyl)aceta-mide (60 mg, 0.154 mmol) and (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one (Int-1, 90 mg, 0.18 mmol) was added MeOH (1.5 mL). The reaction was stirred for 30 minutes. To the reaction mixture was added $NaBH_3CN$ (20 mg, 0.31 mmol) and the reaction was stirred for 1 hour. The reaction was quenched with sat. $NaHCO_3$ and extracted with ethyl acetate. The pooled organic layers were dried over anhydrous sodium sulfate, and concentrated in vacuo. The crude was purified by reverse phase HPLC (15-85% MeOH in $H_2O$) to obtain compound 2 as a white solid (12.6 mg, 9% yield).

MS m/z 787.34 $[M+H]^+$.

Example 3: Synthesis of N-(8-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)octyl)-2-((2-(2,6-dioxopiperidin-3-yl)-1,3-dioxoisoindolin-4-yl)oxy)acetamide (3)

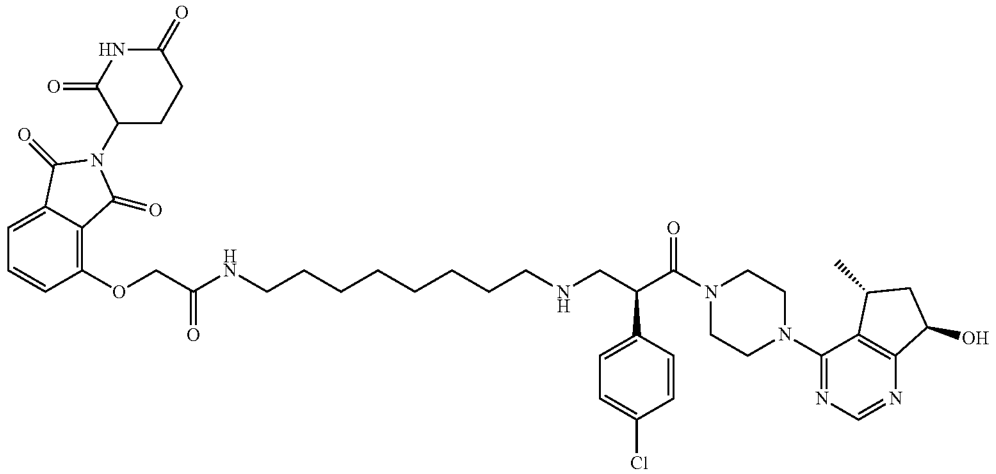

(3

Compound 3 was obtained in an analogous manner to compound 2 in Example 2 using 8-aminooctanol as a white solid (11.1 mg, 13% yield).

$^1H$ NMR (500 MHz, DMSO-$d_6$) δ 8.36 (s, 1H), 7.84 (t, J=5.8 Hz, 1H), 7.77-7.71 (m, 1H), 7.43 (d, J=7.3 Hz, 1H), 7.32 (dd, J=8.4, 1.7 Hz, 3H), 7.29-7.25 (m, 2H), 5.31 (s, 1H), 5.05 (dd, J=12.8, 5.5 Hz, 1H), 4.76 (t, J=6.7 Hz, 1H), 4.69 (s, 2H), 4.14 (dd, J=8.2, 5.7 Hz, 1H), 3.63-3.44 (m, 5H), 3.39 (tt, J=9.5, 4.7 Hz, 3H), 3.16-3.12 (m, 1H), 3.05 (td, J=12.1, 11.1, 7.5 Hz, 3H), 2.83 (ddd, J=16.8, 13.7, 5.4 Hz, 1H), 2.59-2.46 (m, 3H), 2.00-1.80 (m, 4H), 1.37-1.11 (m, 14H), 0.96 (d, J=6.9 Hz, 3H).

MS m/z 857.40 $[M+H]^+$.

Example 4: Synthesis of N-(2-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino) ethoxy)ethoxy)ethyl)-2-((2-(2,6-dioxopiperidin-3-yl)-1,3-dioxoisoindolin-4-yl)oxy)acetamide (4)

(3)

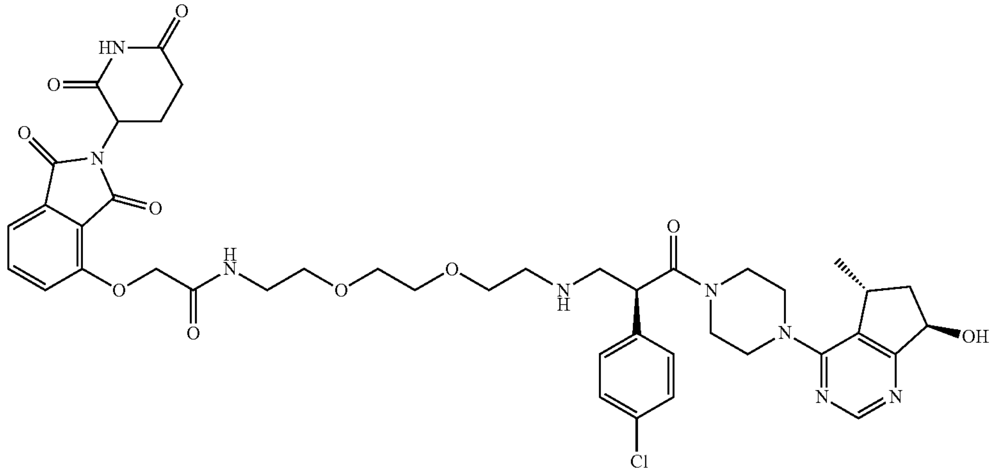

Compound 4 was obtained in an analogous manner to compound 2 in Example 2 using 2-(2-aminoethoxy)ethan-1-ol as a white solid (2.5 mg, 8% yield).

MS m/z 817.34 $[M+H]^+$.

Example 5: Synthesis of N-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy) ethyl)-2-((2-(2,6-dioxopiperidin-3-yl)-1,3-dioxoisoindolin-4-yl)oxy) acetamide (5)

(5)

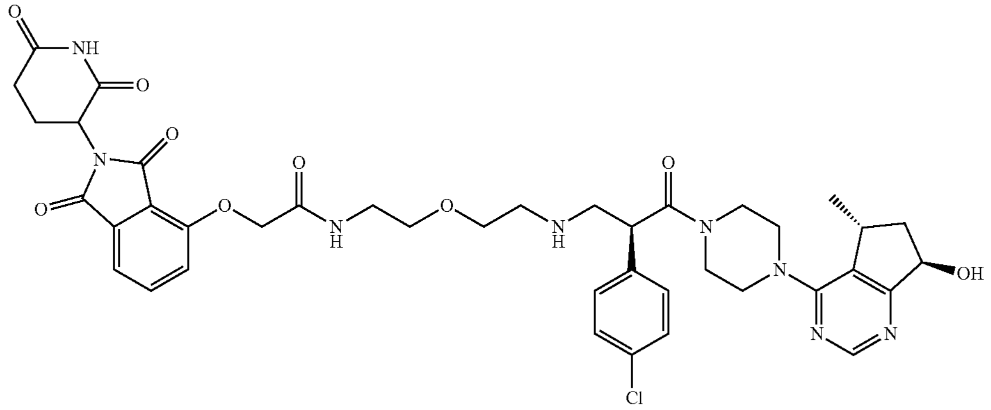

Compound 5 was obtained in an analogous manner to compound 2 in Example 2 using 2-(2-(2-aminoethoxy)ethoxy)ethan-1-ol as a white solid (3.0 mg, 5% yield).

$^1$H NMR (500 MHz, DMSO-$d_6$) δ 8.35 (s, 1H), 7.92 (t, J=5.7 Hz, 1H), 7.74 (t, J=7.9 Hz, 1H), 7.43 (d, J=7.2 Hz, 1H), 7.34 (t, J=8.8 Hz, 3H), 7.26 (d, J=8.1 Hz, 2H), 5.31 (d, J=5.6 Hz, 1H), 5.05 (dd, J=12.8, 5.4 Hz, 1H), 4.76 (q, J=6.2 Hz, 1H), 4.72 (s, 1H), 4.24 (d, J=8.1 Hz, 1H), 3.61 (dd, J=12.9, 5.5 Hz, 1H), 3.52 (d, J=5.6 Hz, 3H), 3.46-3.35 (m, 12H), 3.06 (t, J=9.9 Hz, 1H), 2.87-2.71 (m, 4H), 2.57-2.46 (m, 2H), 2.01-1.80 (m, 4H), 0.95 (d, J=6.8 Hz, 3H).

MS m/z 861.36 [M+H]$^+$.

Example 6: Synthesis of (2S,4R)-1-((2S,15S)-2-(tert-butyl)-15-(4-chlorophenyl)-16-(4-((5R,7R)-7-hydroxy-5-methyl-6,7-dihydro-5H-cyclopenta[d]pyrimidin-4-yl)piperazin-1-yl)-4,16-dioxo-7,10-dioxa-3,13-diazahexadecanoyl)-4-hydroxy-N—((S)-1-(4-(4-methylthiazol-5-yl)phenyl)ethyl)pyrrolidine-2-carboxamide (6)

Scheme 4. Synthesis of compound 6.

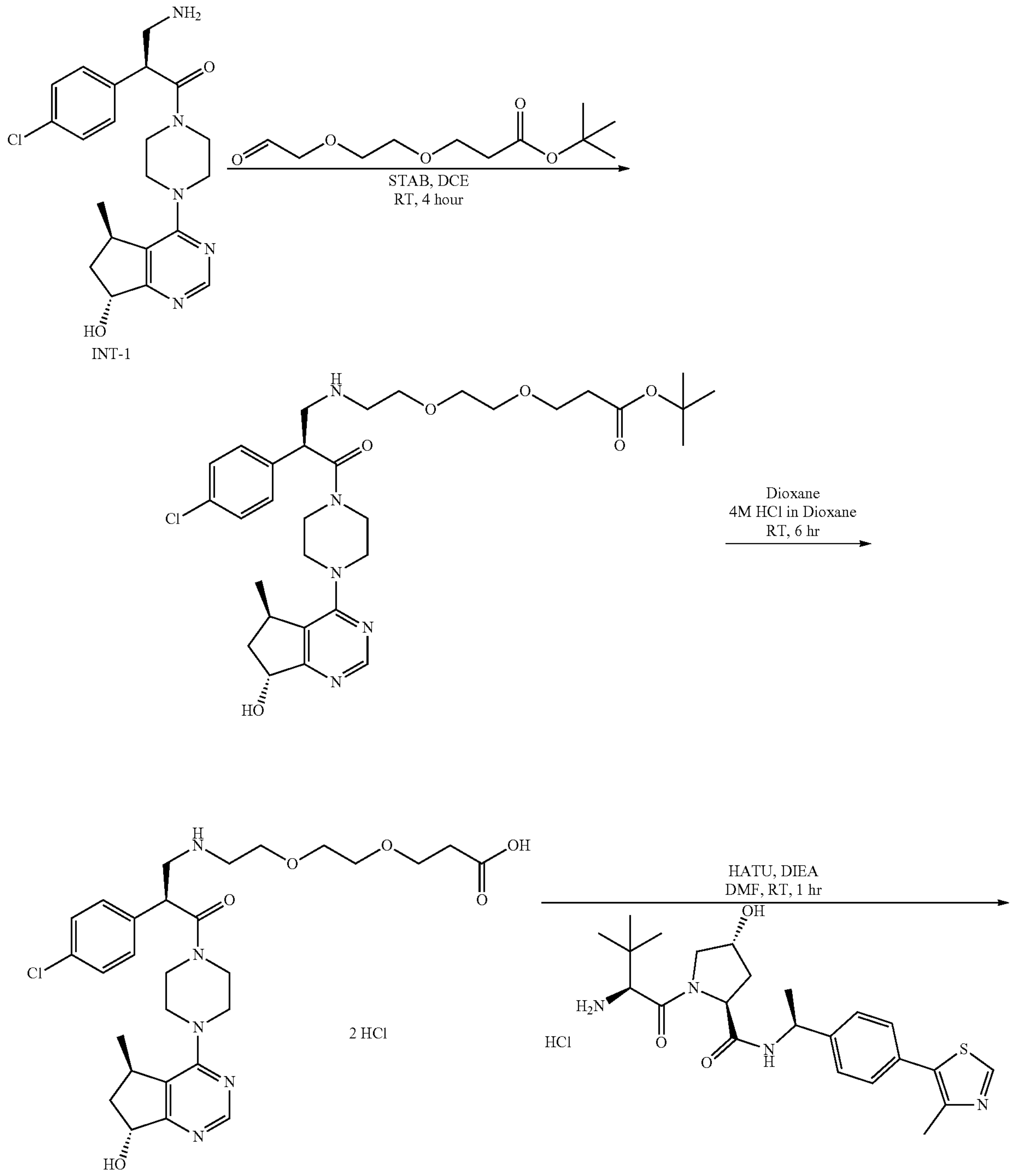

-continued

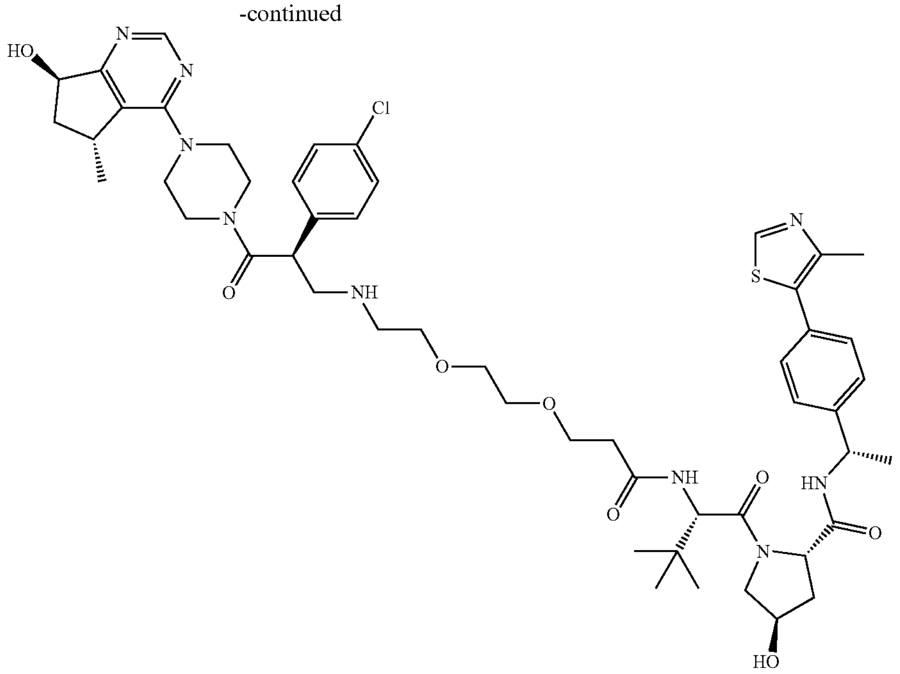

6

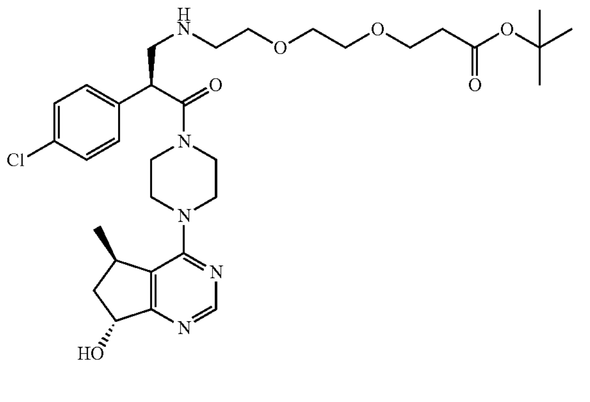 [SMILES: C[C@@H]1C[C@@H](O)c2ncnc(N3CCN(C(=O)[C@H](CNCCOCCOCCC(=O)OC(C)(C)C)c4ccc(Cl)cc4)CC3)c21]

tert-Butyl 3-(2-(2-(((S)-2-(4-Chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy)ethoxy) Propanoate To (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one (57 mg, 0.12 mmol) and tert-butyl 3-(2-(2-oxoethoxy)ethoxy)propanoate (27 mg, 0.12 mmol) was added DCE (3 mL). The reaction was stirred for 20 minutes. STAB (49 mg, 0.23 mmol) was added in 1 portion and the reaction was stirred for 4 hours. The reaction was quenched by sat. $NaHCO_3$, and extracted with DCM (10 mL×3). The pooled organic layers were dried over anhydrous sodium sulfate, and concentrated in vacuo. The crude residue was purified by reverse phase HPLC (0-80% MeOH in $H_2O$) to obtain tert-butyl 3-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy)ethoxy)propanoate as a yellow oil (49 mg, 47% yield).

MS m/z 632.33 $[M+H]^+$.

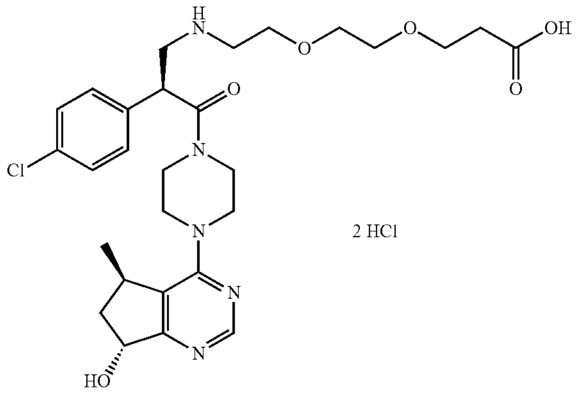 [SMILES: C[C@@H]1C[C@@H](O)c2ncnc(N3CCN(C(=O)[C@H](CNCCOCCOCCC(=O)O)c4ccc(Cl)cc4)CC3)c21]

2 HCl

3-(2-(2-(((S)-2-(4-Chlorophenyl)-3-(4-((5R,7R)-7-hydroxy-5-methyl-6,7-dihydro-5H-cyclo-penta[d]pyrimidin-4-yl)piperazin-1-yl)-3-oxopropyl)amino)ethoxy)ethoxy)propanoic Acid Dihydrochloride Salt To tert-butyl 3-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy)ethoxy)pro-panoate (49 mg, 0.006 mmol) was added 1,4-dioxane (700 μL) and 4 M HCl in 1,4-dioxane (300 μL). The reaction was stirred for 6 hours and concentrated in vacuo. Crude 3-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy)ethoxy)pro-panoic acid (42 mg, quantitative yield) was obtained as the dihydrochloride salt.

MS m/z 576.30 $[M+H]^+$.

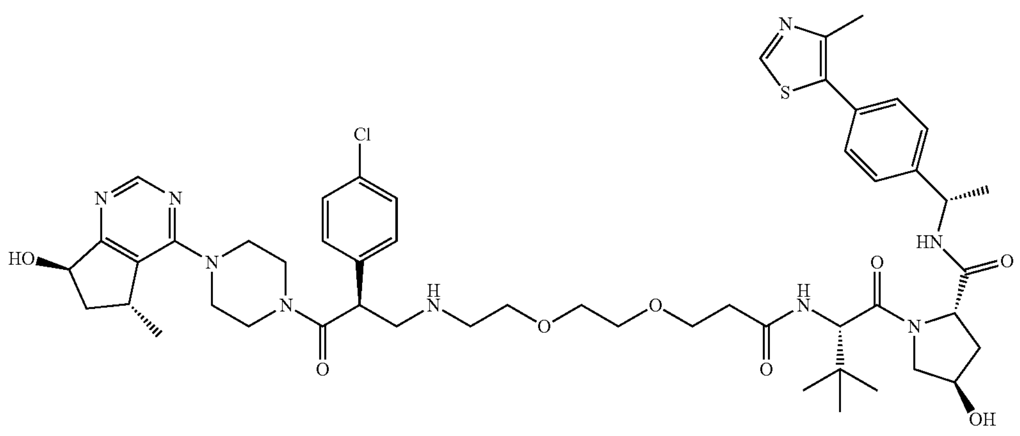

(6)

To 3-(2-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethoxy)ethoxy)propanoic acid dihydrochloride salt (21 mg, 0.026 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochlo-ride (26 mg, 0.052 mmol), and HATU (10 mg, 0.026 mmol) was added DMF (1 mL) and DIEA (32 μL, 0.182 mmol). The reaction was stirred for 1 hour. The reaction was purified by reverse phase HPLC (20-80% MeOH in $H_2O$) to obtain compound 6 as a white solid (10.8 mg, 34% yield).

MS m/z 1002.52 $[M+H]^+$.

Example 7: Synthesis of 3-(4-(10-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)dec-1-yn-1-yl)-1-oxoisoindolin-2-yl)piperidine-2,6-dione (7)

Scheme 5. Synthesis of compound 7.

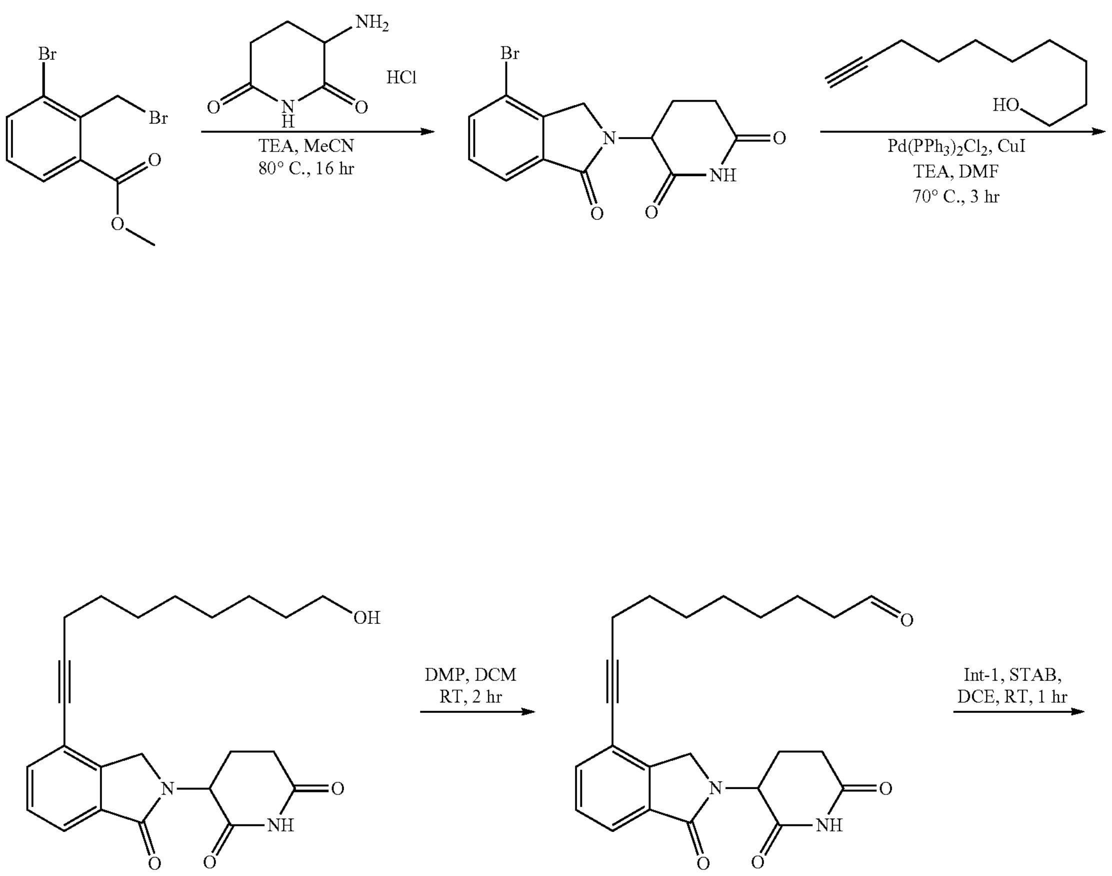

-continued

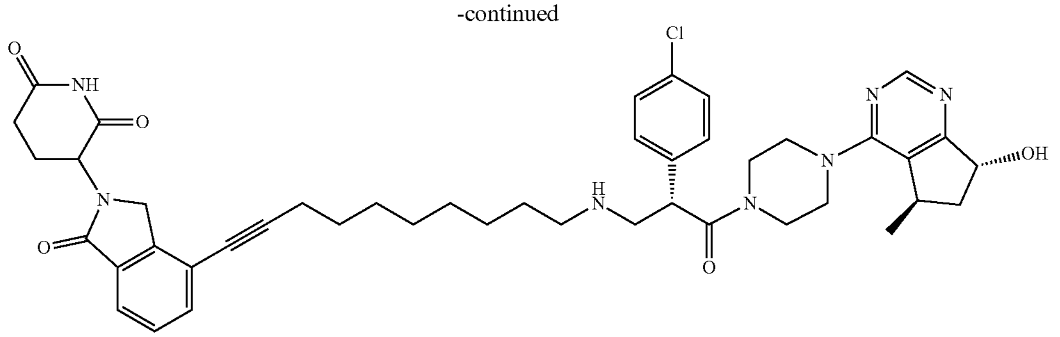

7

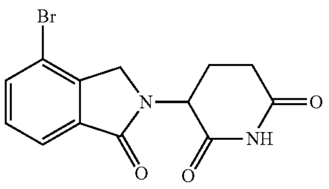 [SMILES: O=C1CCC(N2Cc3c(Br)cccc3C2=O)C(=O)N1]

3-(4-Bromo-1-oxoisoindolin-2-yl)piperidine-2,6-dione

To methyl 3-bromo-2-(bromomethyl)benzoate (1 g, 3.25 mmol) and 3-aminopiperidine-2,6-dione hydrochloride (642 mg, 3.9 mmol) was added MeCN (6.5 mL) and triethylamine (TEA) (1.04 mL, 7.5 mmol). The reaction was stirred at 80° C. for 16 hours. The reaction mixture was cooled to room temperature and concentrated in vacuo. The crude was suspended in ethyl acetate and filtered. The solids were washed with ethyl acetate (50 mL×2) and $H_2O$ (50 mL×3). The solid was collected to obtain 3-(4-bromo-1-oxoisoindolin-2-yl)piperidine-2,6-dione as a purple solid (803 mg, 76% yield).

MS m/z 322.09 $[M+H]^+$.

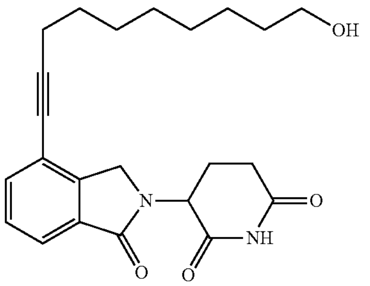 [SMILES: O=C1CCC(N2Cc3c(C#CCCCCCCCCO)cccc3C2=O)C(=O)N1]

3-(4-(10-Hydroxydec-1-yn-1-yl)-1-oxoisoindolin-2-yl)piperidine-2,6-dione

To 3-(4-bromo-1-oxoisoindolin-2-yl)piperidine-2,6-dione (500 mg, 1.55 mmol), dec-9-yn-1-ol (478 mg, 3.10 mmol), $Pd(PPh_3)_2Cl_2$ (113 mg, 0.16 mmol), and CuI (61 mg, 0.32 mmol) was added DMF (8 mL) and TEA (4 mL). The reaction was heated to 70° C. and heated for 3 hours. The reaction mixture was cooled to room temperature and diluted with ethyl acetate. The organic layer was washed with brine (5 mL×4). The pooled organic layers were dried over anhydrous sodium sulfate, and concentrated in vacuo. The crude was purified by column chromatography on silica gel (0-15% MeOH in DCM) to obtain 3-(4-(10-hydroxydec-1-yn-1-yl)-1-oxoisoindolin-2-yl)piperidine-2,6-dione as a yellow solid (503 mg, 82% yield).

MS m/z 397.25 $[M+H]^+$.

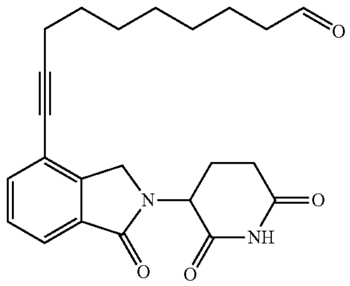 [SMILES: O=CCCCCCCCC#Cc1cccc2c1CN(C1CCC(=O)NC1=O)C2=O]

10-(2-(2,6-Dioxopiperidin-3-yl)-1-oxoisoindolin-4-yl)dec-9-ynal

To 3-(4-(10-hydroxydec-1-yn-1-yl)-1-oxoisoindolin-2-yl)piperidine-2,6-dione (119 mg, 0.3 mmol) was added DCM (6 mL) and DMP (191 mg, 0.45 mmol). The reaction was stirred for 2 hours. The reaction mixture was filtered and concentrated in vacuo to obtain 10-(2-(2,6-dioxopiperidin-3-yl)-1-oxoisoindolin-4-yl)dec-9-ynal as a white solid (40 mg, 34% yield).

MS m/z 395.23 $[M+H]^+$.

(7)

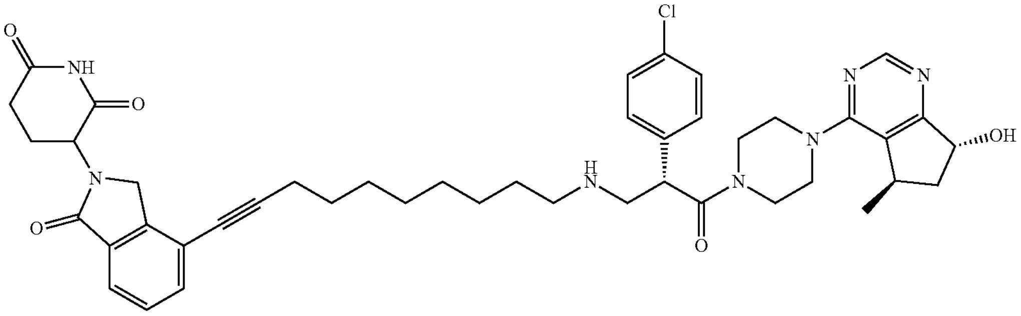

To Int-1 (22 mg, 0.05 mmol) and 10-(2-(2,6-dioxopiperidin-3-yl)-1-oxoisoindolin-4-yl)dec-9-ynal (21 mg, 0.05 mmol) was added DCE (2 mL). The reaction was stirred for 30 minutes. STAB (23 mg, 0.11 mmol) was added in one portion and the reaction was stirred for 1 hour. The reaction was quenched with the addition of sat. $NaHCO_3$ (aq), and extracted with DCM (10 mL×3). The pooled organic layers were dried over anhydrous sodium sulfate, and concentrated in vacuo. The crude was purified by reverse phase HPLC (30-99% MeOH in $H_2O$) to obtain compound 7 as a white solid (12.5 mg, 23% yield).

$^1$H NMR (500 MHz, DMSO-$d_6$) δ 10.92 (s, 1H), 8.56 (d, J=40.2 Hz, 1H), 8.36 (s, 1H), 7.64 (dd, J=7.6, 1.0 Hz, 1H), 7.55 (dd, J=7.7, 1.1 Hz, 1H), 7.49-7.38 (m, 2H), 7.34-7.24 (m, 2H), 5.16-5.01 (m, 2H), 4.48-4.32 (m, 3H), 4.23 (d, J=17.6 Hz, 1H), 3.87 (d, J=10.1 Hz, 1H), 3.69 (dd, J=10.1, 3.9 Hz, 1H), 3.55-3.26 (m, 5H), 3.03 (ddt, J=12.1, 8.1, 4.2 Hz, 1H), 2.93-2.76 (m, 3H), 2.56-2.46 (m, 1H), 2.42-2.31 (m, 3H), 2.09-1.86 (m, 3H), 1.58-1.42 (m, 4H), 1.35 (q, J=7.0 Hz, 2H), 1.22 (d, J=7.7 Hz, 6H), 1.00 (d, J=6.9 Hz, 3H).

MS m/z 794.40 $[M+H]^+$.

Example 8: Synthesis of 3-(4-(6-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)hex-1-yn-1-yl)-1-oxoisoindolin-2-yl)piperidine-2,6-dione (8)

(8)

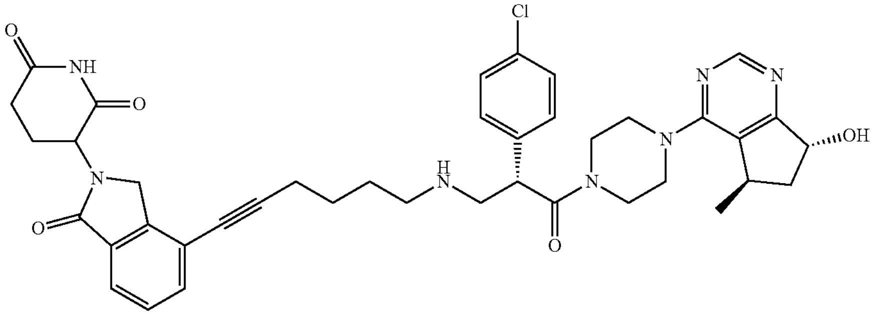

Compound 8 was obtained in an analogous manner to compound 7 in Example 7 using hex-5-yn-1-ol as a white solid (5.20 mg, 12% yield).

$^1$H NMR (500 MHz, DMSO-$d_6$) δ 11.01 (s, 1H), 8.62 (d, J=38.2 Hz, 1H), 8.45 (s, 1H), 7.73 (d, J=7.6 Hz, 1H), 7.63 (d, J=7.6 Hz, 1H), 7.56-7.44 (m, 2H), 7.36 (d, J=8.1 Hz, 2H), 5.15 (dt, J=15.1, 7.5 Hz, 2H), 4.55-4.41 (m, 2H), 4.32 (d, J=17.7 Hz, 2H), 3.99-3.86 (m, 2H), 3.81-3.49 (m, 7H), 3.37 (dt, J=14.9, 8.3 Hz, 2H), 3.13 (ddt, J=12.9, 9.2, 4.6 Hz, 1H), 3.07-2.87 (m, 3H), 2.65-2.52 (m, 3H), 2.44 (td, J=13.2, 4.6 Hz, 1H), 2.03 (td, J=15.8, 12.6, 6.6 Hz, 2H), 1.78 (ddt, J=13.6, 9.8, 5.7 Hz, 2H), 1.62 (p, J=7.3 Hz, 2H), 1.24 (s, 1H), 1.07 (d, J=6.9 Hz, 3H).

MS m/z 738.38 [M+H]$^+$.

Example 9: Synthesis of 4-(4-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)butyl)-2-(2,6-dioxopiperidin-3-yl)isoindoline-1,3-dione (9)

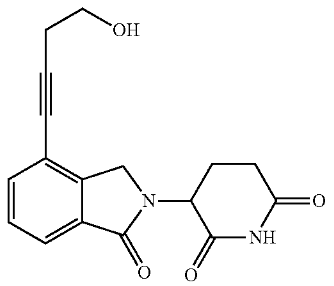 [SMILES: O=C1CCC(N2Cc3c(C#CCCO)cccc3C2=O)C(=O)N1]

2-(2,6-Dioxopiperidin-3-yl)-4-(4-hydroxybut-1-yn-1-yl)isoindoline-1,3-dione

To 4-bromo-2-(2,6-dioxopiperidin-3-yl)isoindoline-1,3-dione (337 mg, 1.0 mmol), but-3-yn-1-ol (140 mg, 2.0 mmol), $Pd(PPh_3)_2Cl_2$ (71 mg, 0.1 mmol), and CuI (38 mg, 0.2 mmol) was added DMF (5 mL) and TEA (2.5 mL). The reaction was heated to 70° C. and heated for 3 hours. The reaction mixture was cooled to room temperature and diluted with ethyl acetate. The organic layer was washed with brine (5 mL×4). The pooled organic layers were dried over anhydrous sodium sulfate, and concentrated in vacuo. The crude was purified by column chromatography on silica gel (0-15% MeOH in DCM) to obtain 2-(2,6-dioxopiperidin-3-yl)-4-(4-hydroxybut-1-yn-1-yl)isoindoline-1,3-dione as a dark yellow solid (228 mg, 70%).

MS m/z 327.15 [M+H]$^+$.

Scheme 6. Synthesis of compound 9.

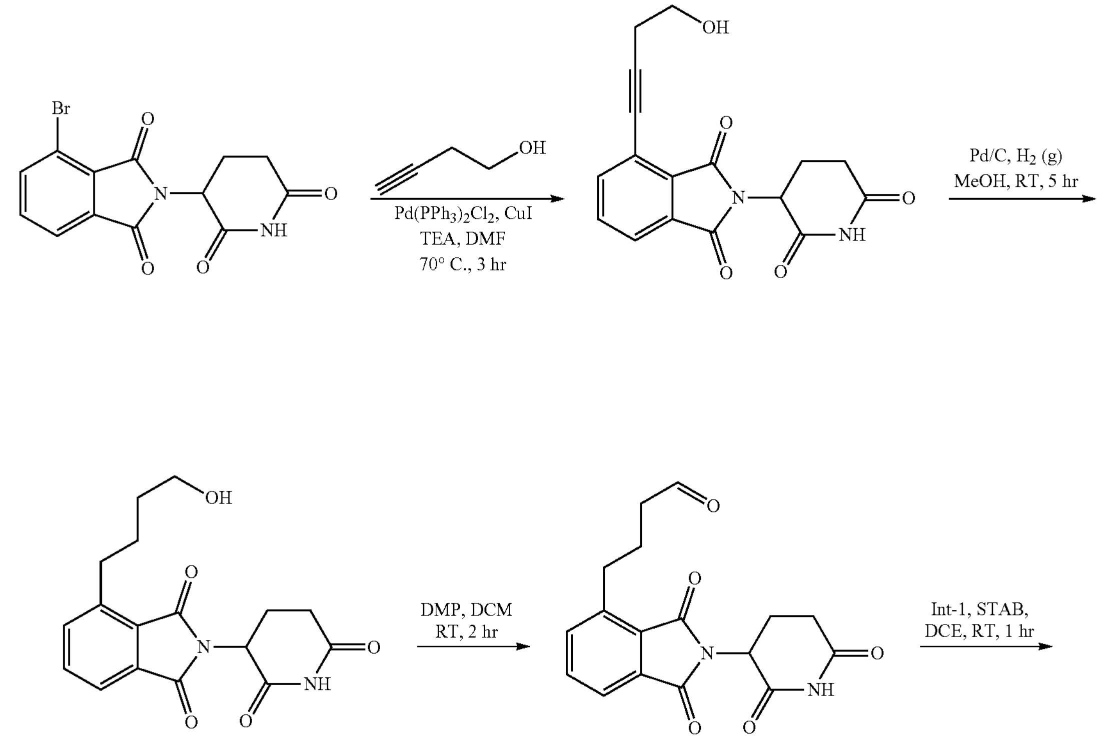

-continued

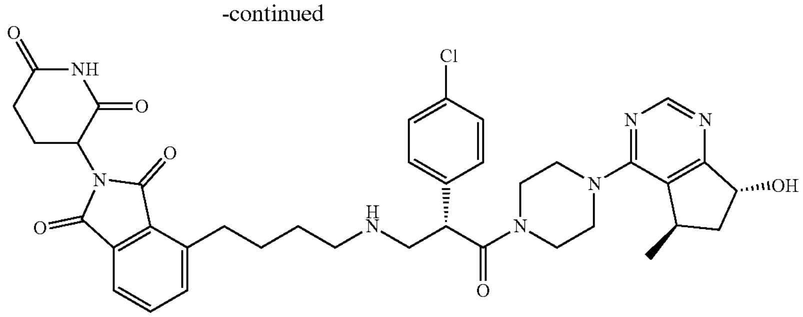

9

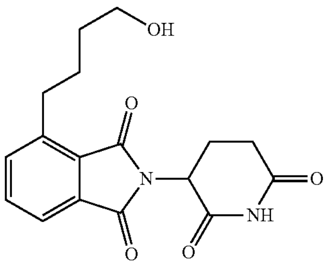 [SMILES: O=C1CCC(N2C(=O)c3cccc(CCCCO)c3C2=O)C(=O)N1]

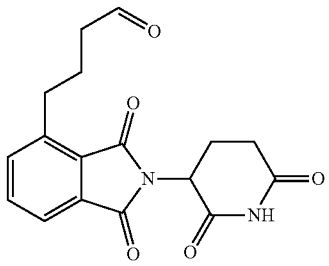 [SMILES: O=CCCCc1cccc2c1C(=O)N(C1CCC(=O)NC1=O)C2=O]

2-(2,6-Dioxopiperidin-3-yl)-4-(4-hydroxybutyl)isoindoline-1,3-dione

To 2-(2,6-dioxopiperidin-3-yl)-4-(4-hydroxybut-1-yn-1-yl)isoindoline-1,3-dione (228 mg, 0.7 mmol) was added MeOH (20 mL) and Pd/C (30 mg). To the reaction mixture was introduced $H_2$ (g) and the reaction was stirred for 5 hours. The reaction was filtered over Celite® and concentrated in vacuo to obtain crude of 2-(2,6-dioxopiperidin-3-yl)-4-(4-hydroxybutyl)isoindoline-1,3-dione (231 mg, quantitative yield).

MS m/z 331.17 $[M+H]^+$.

4-(2-(2,6-dioxopiperidin-3-yl)-1,3-dioxoisoindolin-4-yl)butanal

To 2-(2,6-dioxopiperidin-3-yl)-4-(4-hydroxybutyl)isoindoline-1,3-dione (231 mg, 0.7 mmol) was added DCM (5 mL) and DMP (445 mg, 1.1 mmol). The reaction was stirred for 2 hours, filtered, and concentrated in vacuo to obtain 4-(2-(2,6-dioxopiperidin-3-yl)-1,3-dioxoisoindolin-4-yl)butanal (131 mg, 57% yield).

MS m/z 329.12 $[M+H]^+$.

(9)

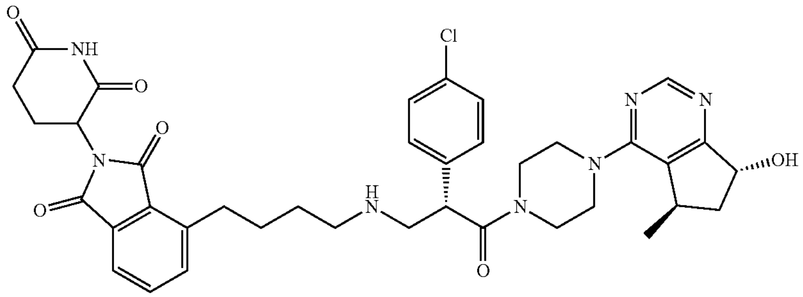

To Int-1 (20 mg, 0.05 mmol), 4-(2-(2,6-dioxopiperidin-3-yl)-1,3-dioxoisoindolin-4-yl)butanal (16 mg, 0.05 mmol) was added DCE (1 mL). The reaction was stirred for 30 minutes. STAB (20 mg, 0.1 mmol) was added in one portion and the reaction was stirred for 1 hour. The reaction was quenched by sat. $NaHCO_3$ (aq) and extracted with DCM (10 mL×3). The pooled organic layers were dried over anhydrous sodium sulfate, and concentrated in vacuo. The crude residue was purified by reverse phase HPLC (20-80% MeOH in $H_2O$) to obtain compound 9 as a white solid (6.3 mg, 14% yield).

$^1H$ NMR (500 MHz, DMSO-$d_6$) δ 11.12 (d, J=3.4 Hz, 1H), 8.67 (s, 1H), 8.44 (d, J=55.2 Hz, 1H), 7.89-7.80 (m, 1H), 7.76-7.67 (m, 1H), 7.50 (d, J=8.2 Hz, 2H), 7.35 (dd,

J=8.8, 3.2 Hz, 2H), 5.22-5.08 (m, 2H), 4.46 (dt, J=8.7, 4.2 Hz, 1H), 3.81-3.44 (m, 7H), 3.39 (dtd, J=21.0, 10.7, 10.0, 4.7 Hz, 2H), 3.11 (ddt, J=12.6, 8.7, 4.3 Hz, 1H), 2.96 (tt, J=13.8, 7.0 Hz, 2H), 2.91-2.85 (m, 1H), 2.85-2.73 (m, 2H), 2.66-2.52 (m, 2H), 2.19-1.93 (m, 3H), 1.68 (p, J=7.5 Hz, 2H), 1.64-1.52 (m, 2H), 1.24 (d, J=3.3 Hz, 1H), 1.07 (dd, J=7.3, 3.2 Hz, 3H).

MS m/z 728.34 $[M+H]^+$.

Example 10: Synthesis of 3-(4-(10-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)decyl)-1-oxoisoindolin-2-yl)piperidine-2,6-dione (10)

Scheme 7. Synthesis of compound 10.

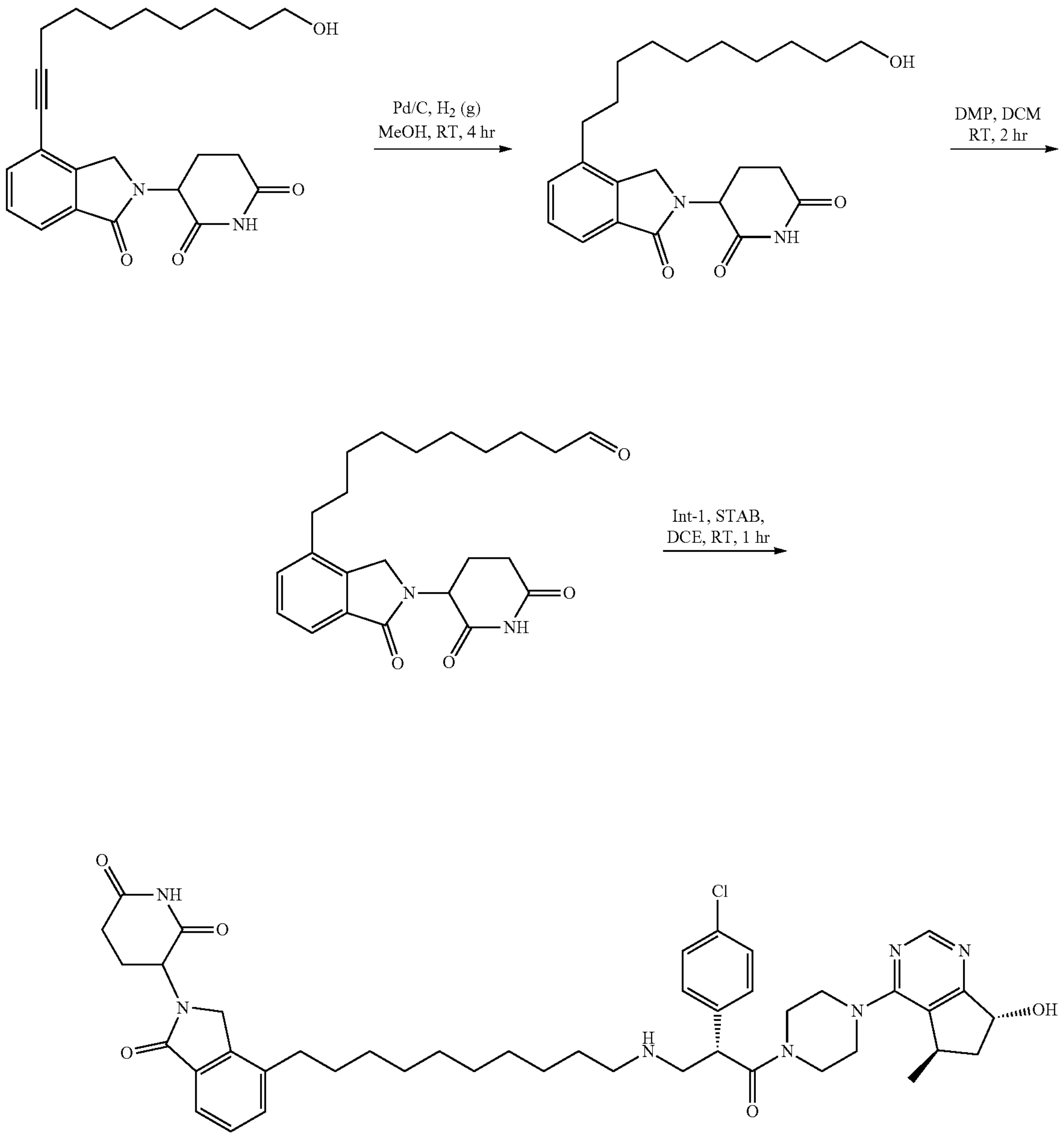

10

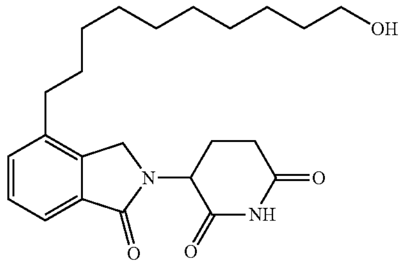 [SMILES: O=C1CCC(N2Cc3c(CCCCCCCCCCO)cccc3C2=O)C(=O)N1]

3-(4-(10-Hydroxydecyl)-1-oxoisoindolin-2-yl)piperidine-2,6-dione

To 3-(4-(10-hydroxydec-1-yn-1-yl)-1-oxoisoindolin-2-yl)piperidine-2,6-dione (100 mg, 0.25 mmol) and Pd/C (10 mg) was added MeOH (10 mL). $H_2$ (g) was introduced to the reaction mixture and stirred for 4 hours. The reaction mixture was filtered over Celite® and concentrated in vacuo to obtain crude of 3-(4-(10-hydroxydecyl)-1-oxoisoindolin-2-yl)piperidine-2,6-dione (105 mg, quantitative yield) as a tan solid.

MS m/z 401.30 $[M+H]^+$.

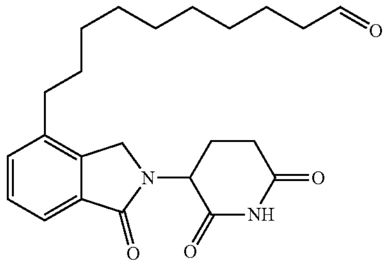 [SMILES: O=CCCCCCCCCCc1cccc2c1CN(C1CCC(=O)NC1=O)C2=O]

10-(2-(2,6-Dioxopiperidin-3-yl)-1-oxoisoindolin-4-yl)decanal

To 3-(4-(10-hydroxydecyl)-1-oxoisoindolin-2-yl)piperidine-2,6-dione (40 mg, 0.1 mmol) was added DCM (2 mL) and DMP (64 mg, 0.15 mmol). The reaction was stirred for 2 hours. The reaction mixture was filtered and concentrated in vacuo to obtain 10-(2-(2,6-dioxopiperidin-3-yl)-1-oxoisoindolin-4-yl)decanal (36 mg, 90% yield) as a white solid.

MS m/z 399.35 $[M+H]^+$.

(10)

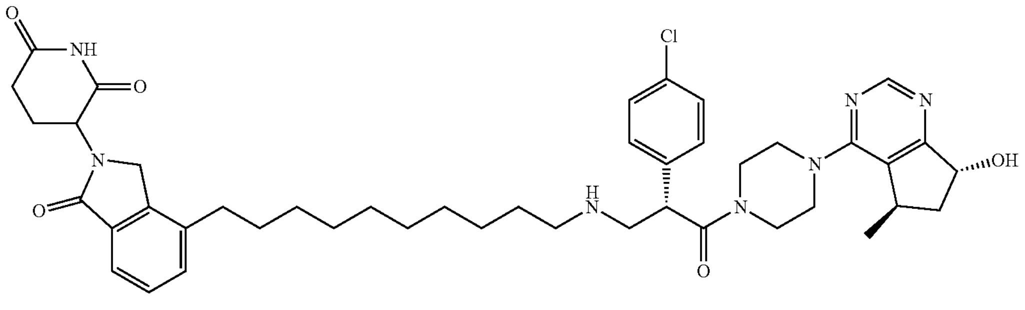

To Int-1 (35 mg, 0.085 mmol) and 10-(2-(2,6-dioxopiperidin-3-yl)-1-oxoisoindolin-4-yl)decanal (34 mg, 0.085 mmol) was added DCE (1 mL). The reaction mixture was stirred for 30 minutes. STAB (36 mg, 0.17 mmol) was added in one portion and the reaction was stirred for 1 hour. The reaction was quenched with the addition of sat. $NaHCO_3$ (aq) and extracted with DCM (20 mL×3). The pooled organic layers were dried over anhydrous sodium sulfate, and concentrated in vacuo. The crude residue was purified by reverse phase HPLC (15-85% MeOH in $H_2O$) to obtain compound 10 as a white solid (11 mg, 25% yield).

$^1$H NMR (500 MHz, DMSO-$d_6$) δ 10.99 (s, 1H), 8.65 (s, 1H), 8.52-8.37 (m, 1H), 7.57 (dd, J=5.9, 2.7 Hz, 1H), 7.51-7.48 (m, 1H), 7.46 (d, J=6.0 Hz, 2H), 7.40-7.32 (m, 2H), 5.19-5.10 (m, 2H), 4.51-4.41 (m, 2H), 4.30 (d, J=17.0 Hz, 1H), 3.98-3.89 (m, 1H), 3.75-3.50 (m, 7H), 3.42-3.33 (m, 2H), 3.11 (dp, J=12.6, 4.2 Hz, 1H), 2.98-2.88 (m, 3H), 2.66-2.58 (m, 3H), 2.43 (qd, J=13.2, 4.4 Hz, 2H), 2.08 (ddt, J=10.8, 5.3, 2.7 Hz, 1H), 2.02 (dd, J=10.4, 4.9 Hz, 2H), 1.63-1.53 (m, 4H), 1.30 (d, J=4.7 Hz, 4H), 1.25 (s, 8H), 1.07 (d, J=6.9 Hz, 3H).

MS m/z 798.45 $[M+H]^+$.

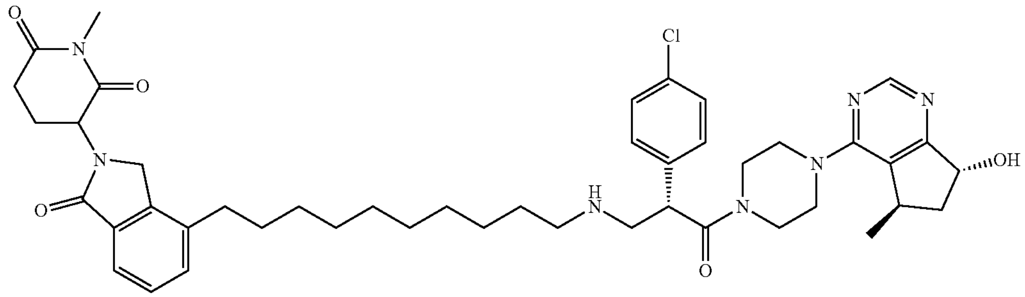 [SMILES: C[C@@H]1C[C@@H](O)c2ncnc(N3CCN(C(=O)[C@H](CNCCCCCCCCCCc4cccc5c4CN(C4CCC(=O)N(C)C4=O)C5=O)c4ccc(Cl)cc4)CC3)c21]

3-(4-(10-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)decyl)-1-oxoisoindolin-2-yl)-1-methylpiperidine-2,6-dione (10-Me)

Compound 10-Me was obtained in an analogous manner to compound 10 using 8-3-(4-(10-hydroxydecyl)-1-oxoisoindolin-2-yl)-1-methylpiperidine-2,6-dione as an off-white solid (9 mg, 16% yield).

$^1$H NMR (500 MHz, DMSO-$d_6$) 8.43 (s, 1H), 7.57 (dd, J=5.8, 2.8 Hz, 1H), 7.49-7.43 (m, 4H), 7.37-7.32 (m, 2H), 5.40 (d, J=5.5 Hz, 1H), 5.21 (dd, J=13.4, 5.1 Hz, 1H), 4.83 (q, J=6.3 Hz, 1H), 4.45 (d, J=17.1 Hz, 1H), 4.38 (dd, J=8.9, 5.1 Hz, 1H), 4.29 (d, J=17.1 Hz, 1H), 3.76-3.41 (m, 8H), 3.41-3.34 (m, 3H), 3.10 (t, J=10.0 Hz, 1H), 3.01 (s, 3H), 2.99-2.95 (m, 1H), 2.83-2.73 (m, 3H), 2.63 (t, J=7.7 Hz, 2H), 2.43 (qd, J=13.2, 4.5 Hz, 1H), 2.05-1.87 (m, 3H), 1.59 (t, J=7.5 Hz, 2H), 1.50 (s, 2H), 1.33-1.27 (m, 4H), 1.23 (s, 8H), 1.02 (d, J=6.9 Hz, 3H).

LC-MS: m/z 812.47 [M+1].

Example 11: Synthesis of N—((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)-11-(2-(2,6-dioxopiperidin-3-yl)-1-oxoisoindolin-4-yl)undecanamide (11)

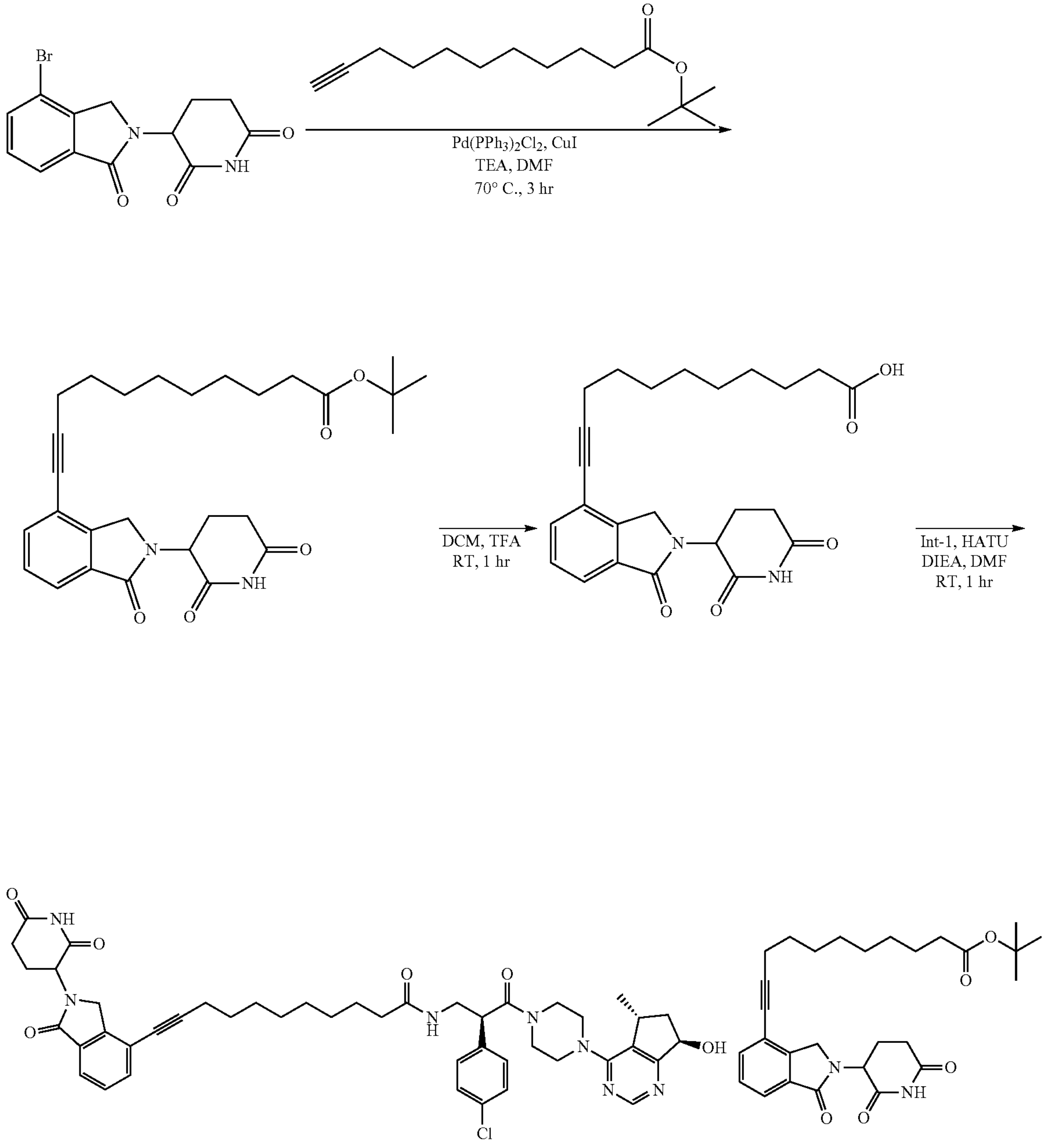

11 tert-Butyl 11-(2-(2,6-dioxopiperidin-3-yl)-1-oxoisoindolin-4-yl)undec-10-ynoate

To 3-(4-bromo-1-oxoisoindolin-2-yl)piperidine-2,6-dione (162 mg, 0.5 mmol), tert-butyl undec-10-ynoate (238 mg, 1.0 mmol), $Pd(PPh_3)_2Cl_2$ (35 mg, 0.05 mmol), and CuI (19 mg, 0.1 mmol) was added DMF (2.5 mL) and TEA (1.3 mL). The reaction was heated to 70° C. and heated for 3 hours. The reaction mixture was cooled to room temperature and diluted with ethyl acetate. The organic layer was washed with brine (5 mL×4). The pooled organic layers were dried over anhydrous sodium sulfate, and concentrated in vacuo. The crude was purified by column chromatography on silica gel (0-15% MeOH in DCM) to obtain tert-butyl 11-(2-(2,6-dioxopiperidin-3-yl)-1-oxoisoindolin-4-yl)undec-10-ynoate (120 mg, 50% yield) as a black solid.

MS m/z 481.31 $[M+H]^+$.

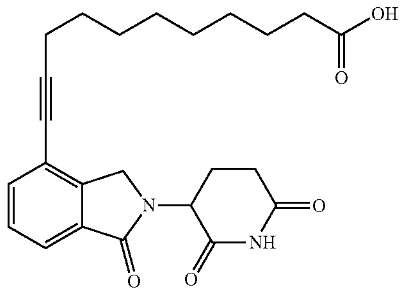 [SMILES: O=C(O)CCCCCCCCC#Cc1cccc2c1CN(C1CCC(=O)NC1=O)C2=O]

11-(2-(2,6-Dioxopiperidin-3-yl)-1-oxoisoindolin-4-yl)undec-10-ynoic Acid

To tert-butyl 11-(2-(2,6-dioxopiperidin-3-yl)-1-oxoisoindolin-4-yl)undec-10-ynoate was added DCM (1 mL) and TFA (0.3 mL). The reaction was stirred at room temperature for 1 hour. The reaction mixture was concentrated in vacuo and purified by reverse phase HPLC (15-90% MeOH in $H_2O$) to obtain 11-(2-(2,6-dioxopiperidin-3-yl)-1-oxoisoindolin-4-yl)undec-10-ynoic acid (6.5 mg, 20% yield) as a white solid.

MS m/z 425.28 $[M+H]^+$.

Compound 11

(11)

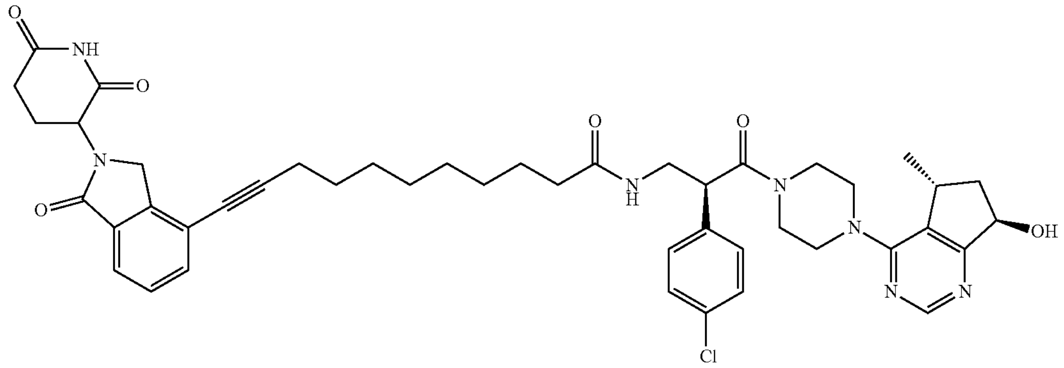

To Int-1 (6 mg, 0.015 mmol), 11-(2-(2,6-dioxopiperidin-3-yl)-1-oxoisoindolin-4-yl)undec-10-ynoic acid (7 mg, 0.015 mmol), and HATU (6 mg, 0.015 mmol) was added DMF (1 mL) and DIEA (11 μL, 0.06 mmol). The reaction was stirred for 1 hour and purified by reverse phase HPLC (15-90% MeOH in $H_2O$) to obtain compound 11 as a white solid (1 mg, 6% yield).

MS m/z 822.40 $[M+H]^+$.

Example 12: Degradation of AKT1, AKT2 and AKT3 in MDA-MB-468 and MCF10A Cell Lines with Inventive Bifunctional Compounds MDA-MB-468 (human breast cancer cell line) cells were maintained in RPMI 1640 (Wisent Bioproducts) supplemented with 10% FBS (Thermo Fisher Scientific) and MCF10A (human breast epithelial cell line) cells were maintained in Dulbecco's modified Eagle's medium (DMEM)/Ham's F12 (Wisent Bioproducts) supplemented with 5% equine serum (Fisher), insulin (10 μg/ml) (Life Technologies), hydrocortisone (500 ng/ml) (Sigma-Aldrich®), epidermal growth factor (20 ng/ml) (R&D Systems), and cholera toxin (100 ng/ml) (List Biological Lab). MDA-MB-468 and MCF10A cells were seeded at 250,000 cells/mL and 200,000 cells/mL, respectively. The following day cells were treated with inventive bifunctional compounds. After 24 hours, cells were washed with phosphate-buffered saline at 4° C. and lysed in radioimmunoprecipitation assay (RIPA) buffer (150 mM Tris-HCl, 150 mM NaCl, 0.5% (w/v) sodium deoxycholate, 1% (v/v) NP-40, pH 7.5) containing 0.1% (w/v) sodium dodecyl sulfate, 1 mM sodium pyrophosphate, 20 mM sodium fluoride, 50 nM calyculin, and 0.5% (v/v) protease inhibitor cocktail (Sigma-Aldrich®)). Cell extracts were precleared by centrifugation at 14,000 rpm for 10 minutes at 4° C. The Bio-Rad DC protein assay was used to assess protein concentration, and sample concentration was normalized using SDS sample buffer. Lysates were resolved on acrylamide gels by SDS-polyacrylamide gel electrophoresis and electrophoretically transferred to nitrocellulose membrane (BioRad) at 100 volts for 90 minutes. Membranes were blocked in 5% (w/v) nonfat dry milk or 5% (w/v) bovine serum albumin in tris-buffered saline (TBS) buffer for 1 hour then incubated with specific primary antibodies diluted in blocking buffer at 4° C. overnight, shaking. Anti-AKT1 (CST2938), anti-AKT2 (CST3063), anti-AKT3 (CST8018), anti-phospho-Thr246-PRAS40 (CST2997), anti-PRAS40 (CST2691), and anti-Vinculin (CST13901) antibodies were purchased from Cell Signaling Technology®. Membranes were washed three times in TBS-T and incubated with fluorophore-conjugated secondary antibodies (LI-COR®) for 1 hour at room temperature. Membranes were washed three times in TBS-T and imaged using an Odyssey® CLx (LI-COR®). Images were stored and analyzed using ImageStudio™ (LI-COR®) software.

AKT isoforms were degraded in MDA-MB-468 cells in a dose-dependent manner after 24-hour treatment with inventive bifunctional compounds 1 and 3 (FIG. 1). Treatment with DMSO control indicates baseline AKT isoform expression. GDC0068 treatment resulted in a reduction of phosphorylated proline-rich AKT substrate of 40 kDa (PRAS40) signal indicating AKT inhibition.

Example 13: Degradation of AKT1, AKT2 and AKT3 in MCF10A Cell Lines with Inventive Bifunctional Compounds The degradation of AKT1, AKT2 and AKT3 in MCF10A cell lines with inventive bifunctional compounds 1 and 3 was performed as described in Example 12.

Figure 2:
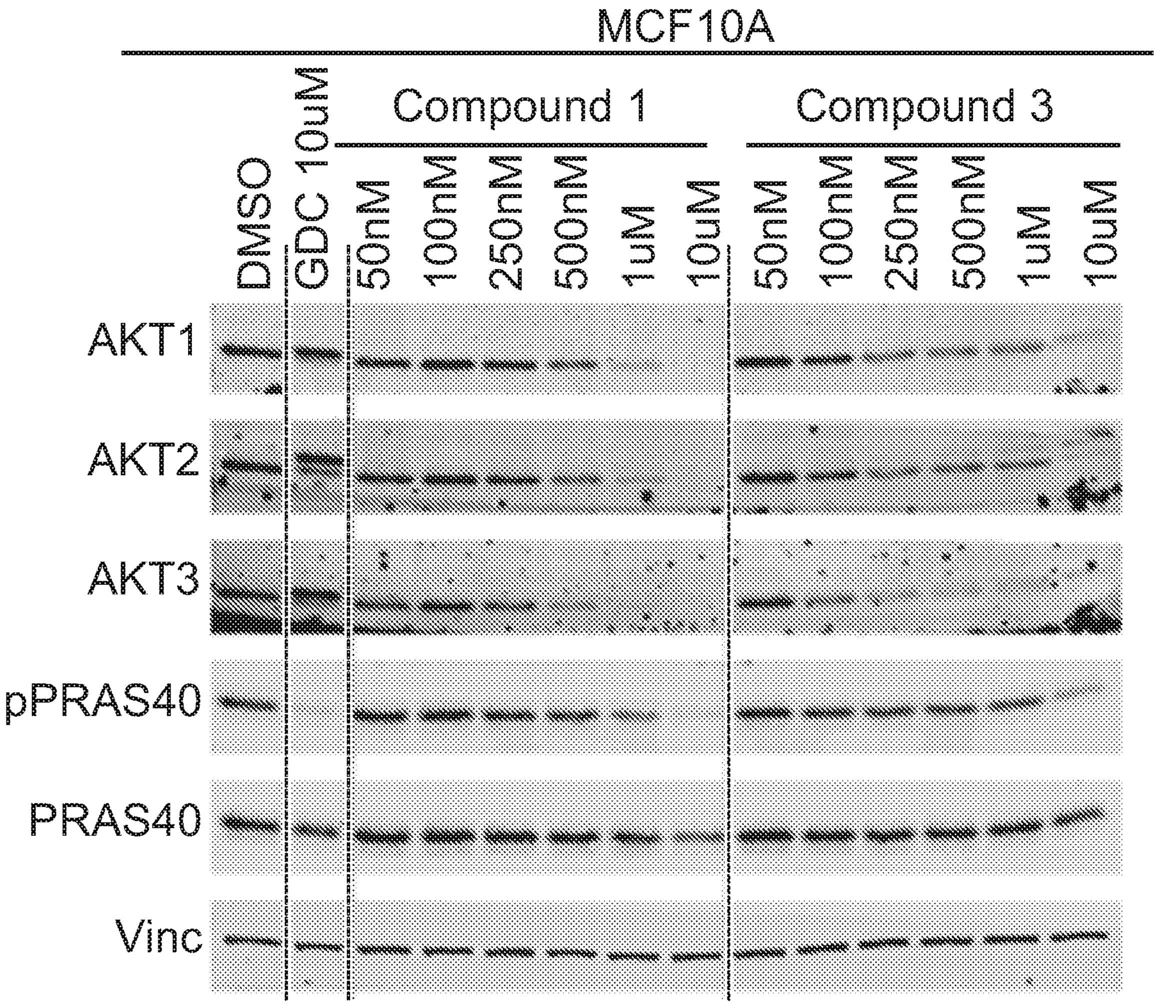
FIG. 2 is an immunoblot that shows the degradation of all three AKT isoforms in MCF10A cell lines with different concentrations of inventive bifunctional compounds 1 and 3. DMSO and AKT inhibitor GDC-0068 (GDC) were used as negative and positive controls, respectively.

AKT isoforms were degraded in MCF10A cells in a dose-dependent manner after 24-hour treatment with inventive bifunctional compounds 1 and 3 (FIG. 2). Treatment with DMSO control indicates baseline AKT isoform expression. GDC0068 treatment resulted in a reduction of phosphorylated PRAS40 signal indicating AKT inhibition.

Example 14: Degradation of AKT1, AKT2 and AKT3 in MDA-MB-468 and MCF10A Cell Lines with Inventive Bifunctional Compound 10

The degradation of AKT1, AKT2 and AKT3 in MDA-MB-468 and MCF10A cell lines with inventive bifunctional compound 10 was performed as described in Example 12.

Figure 3:
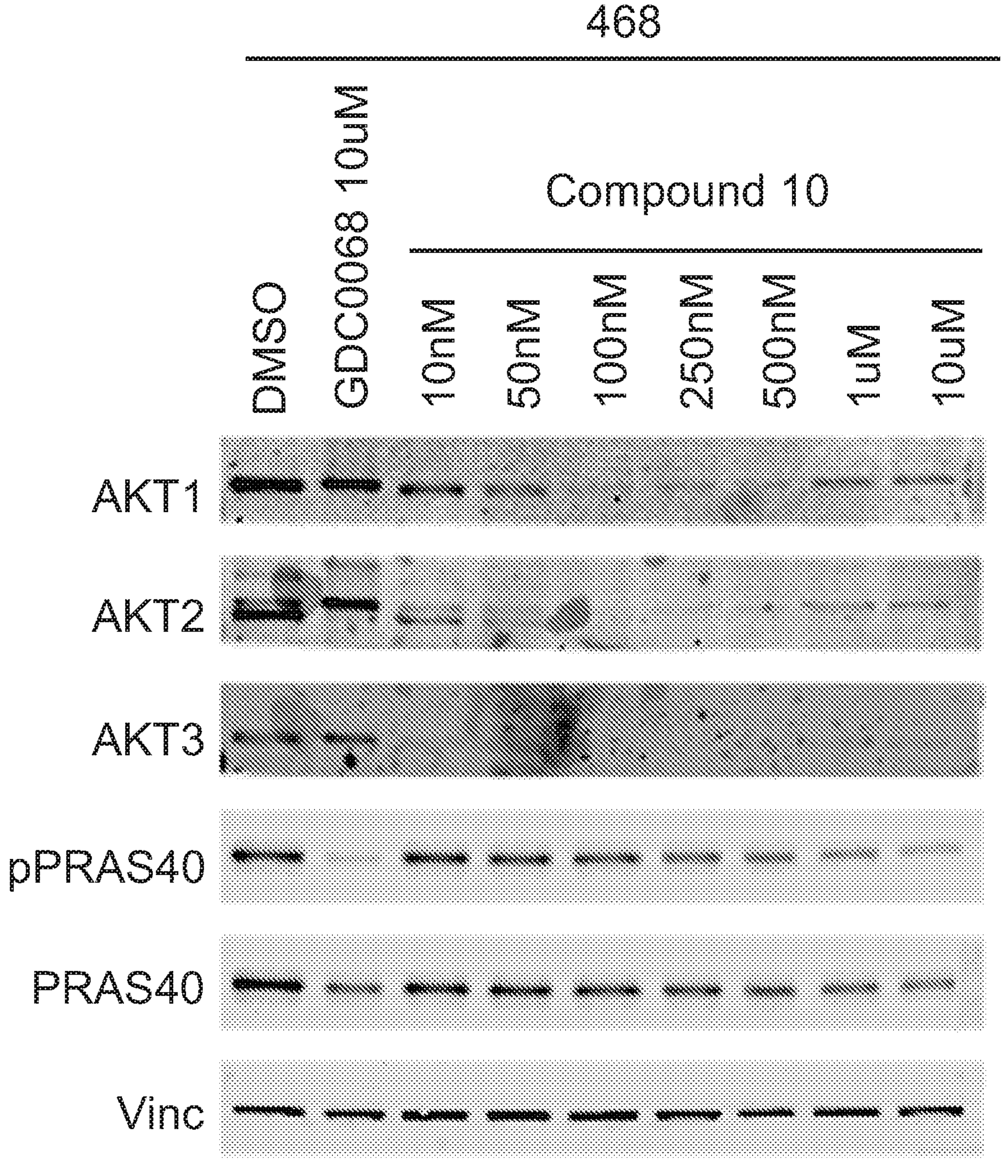
FIG. 3 is an immunoblot that shows the degradation of all three AKT isoforms in MDA-MB-468 cell lines with different concentrations of inventive bifunctional compound 10. DMSO and AKT inhibitor GDC-0068 were used as negative and positive controls, respectively.
Figure 4:
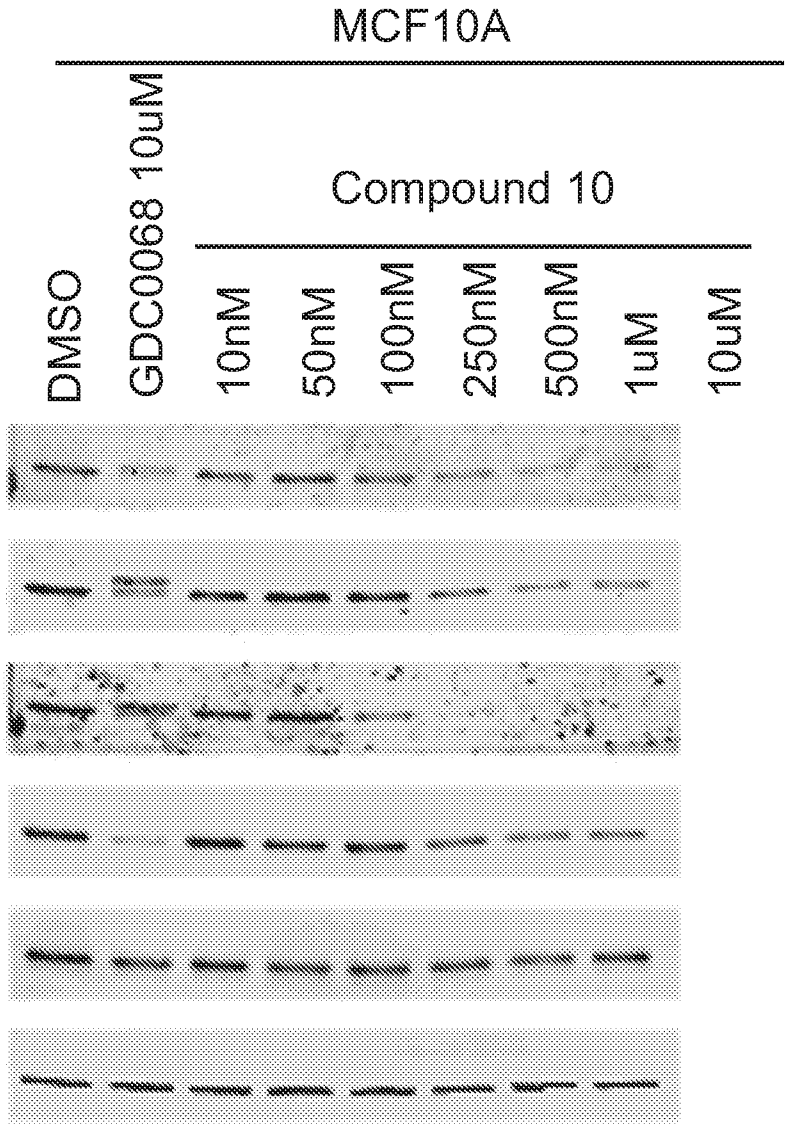
FIG. 4 is an immunoblot that shows the degradation of all three AKT isoforms in MCF10A cell lines with different concentrations of inventive bifunctional compound 10. DMSO and AKT inhibitor GDC-0068 were used as negative and positive controls, respectively.

AKT isoforms were degraded in MDA-MB-468 cells (FIG. 3) and MCF10A cells (FIG. 4) in a dose-dependent manner after 24-hour treatment with bifunctional compounds 1 and 3. Treatment with DMSO control indicates baseline AKT isoform expression. GDC0068 treatment resulted in a reduction of phosphorylated PRAS40 signal indicating AKT inhibition.

Example 15: AKT Binding Assay

Z'-LYTE assays (catalog number PV3193, Invitrogen™) were conducted for AKT1, AKT2, AKT3, PKG1, S6K1, PKN1, βMSK2, and Haspin at Life Technologies™ in a 10-point dose response using Km ATP concentrations. LanthaScreen™ assays were conducted for RET (V804M) in a 10-point dose response at Life Technologies™.

The results of the AKT binding assay are summarized in Table 1. The data in Table 1 show that the inventive compounds inhibited all AKT isoforms at low nanomolar concentrations.

TABLE 1

AKT binding assay with inventive bifunctional compounds.

| | Biochemical Binding (nM) | | |
|---|---|---|---|
| Inventive Compounds | AKT1 | AKT2 | AKT3 |
| Compound 1 | 1.58 | 15.1 | 4.94 |
| Compound 2 | 3.93 | 31.4 | 20.4 |
| Compound 3 | 1.03 | 4.04 | 1.23 |
| Compound 4 | 6.97 | N.T | N.T |
| Compound 5 | 3.4 | N.T | N.T |
| Compound 6 | 3.8 | N.T | N.T |
| Compound 7 | 2.46 | N.T | N.T |
| Compound 8 | N.T | N.T | N.T |
| Compound 9 | 1.8 | N.T | N.T |
| Compound 10 | N.T | N.T | N.T |
| Compound 11 | N.T | N.T | N.T |

N.T = Not tested

Example 16: Inventive Bifunctional Compound 10 Induced Potent Degradation of AKT Isoforms Dependent on CRBN, Neddylation, and the Proteasome Experimental and Model and Subject Details MOLT4 (male, CVCL_0013), Jurkat (male, CVCL_0065), ZR-75-1 (female, CVCL_0588), LNCaP (male, VCL_0395), T47D (female, CVCL_0553), MCF-7 (female, CVCL_0031), MDA-MB-468 (female, CVCL_0419), and HCC1937 (female, CVCL_0290) cells were cultured in RPMI media (Wisent Bioproducts) supplemented with 10% heat inactivated fetal bovine serum (ThermoFisher Scientific) and 100 U/mL Penicillin-Streptomycin (Gibco®) at 37° C. in the presence of 5% $CO_2$. IGROV1 (female, CVCL_1304) and PC3 (male, CVCL_0035) cells were cultured in DMEM media (Gibco®) supplemented with 10% heat inactivated fetal bovine serum (ThermoFisher Scientific) and 100 U/mL Penicillin-Streptomycin (Gibco®) at 37° C. in the presence of 5% $CO_2$.

Drug Treatment Experiments

Cells were plated at 250,000 cells per mL (MDA-MB-468, MOLT4, IGROV1, PC3, and Jurkat) or 200,000 cells per mL (T47D) in 2 mL per well of RPMI or DMEM media with 10% serum in 6-well treated tissue culture plates (Greiner, Cat #TCG-657160) or 60 mm treated tissue culture plates (Corning®, Cat #430166) and incubated overnight. The next day, cells were treated with the indicated compounds at the appropriate concentration and protein lysates were harvested at the times specified.

Immunoblotting

Cells were washed once in 1×PBS then lysed in RIPA buffer (150 mM Tris-HCl, 150 mM NaCl, 0.5% (w/v) sodium deoxycholate, 1% (v/v) NP-40, pH 7.5) containing 0.1% (w/v) sodium dodecyl sulfate, 1 mM sodium pyrophosphate, 20 mM sodium fluoride, 50 nM calyculin, and 0.5% (v/v) protease inhibitor cocktail (Sigma-Aldrich®) for 15 minutes. Cell extracts were precleared by centrifugation at 14,000 rpm for 10 minutes at 4° C. The Bio-Rad DC protein assay was used to assess protein concentration, and sample concentration was normalized using SDS sample buffer. Lysates were resolved on acrylamide gels by SDS-polyacrylamide gel electrophoresis and electrophoretically transferred to nitrocellulose membrane (BioRad) at 100 volts for 90 minutes. Membranes were blocked in 5% (w/v) nonfat dry milk in tris-buffered saline (TBS) buffer for 1 hour then incubated with specific primary antibodies diluted in 5% (w/v) nonfat dry milk in TBS-T (TBS with 0.05% Tween®-20) at 4° C. overnight, shaking. The next day, membranes were washed with TBS-T then incubated for 1 hour at room temperature with fluorophore-conjugated secondary antibodies (LI-COR® Biosciences). The membrane was washed again with TBS-T then imaged with a LI-COR® Odyssey® CLx Imaging System (LI-COR® Biosciences).

Tandem Mass Tag (TMT) LC-MS Sample Preparation

MOLT4 cells were treated with DMSO, 250 nM inventive bifunctional compound 10 for 4 hours in biological triplicates. Cells were harvested by centrifugation. Lysis buffer (8 M Urea, 50 mM NaCl, 50 mM 4-(2hydroxyethyl)-1-piperazineethanesulfonic acid (EPPS) pH 8.5, 1× Roche® protease inhibitor and 1× Roche® PhosStop™ was added to the cell pellets and cells were homogenized by 20 passes through a 21 gauge (1.25 in. long) needle to achieve a cell lysate with a protein concentration between 0.5-4 mg $mL^{-1}$. The homogenized sample was clarified by centrifugation at 20,000×g for 10 minutes at 4° C.

A Bradford assay was used to determine the final protein concentration in the cell lysate. 200 mg protein for each sample were reduced and alkylated as previously described (An et al., Nat. Comm. 8:15398 (2017)). Proteins were precipitated using methanol/chloroform. In brief, four volumes of methanol were added to the cell lysate, followed by one volume of chloroform, and finally three volumes of water. The mixture was vortexed and centrifuged at 14,000×g for 5 minutes to separate the chloroform phase from the aqueous phase. The precipitated protein was washed with three volumes of methanol, centrifuged at 14,000×g for 5 min, and the resulting washed precipitated protein was allowed to air dry. Precipitated protein was resuspended in 4 M Urea, 50 mM HEPES pH 7.4, followed by dilution to 1 M urea with the addition of 200 mM EPPS pH 8 for digestion with LysC (1:50; enzyme:protein) for 12 hours at rt. The LysC digestion was diluted to 0.5 M Urea, 200 mM EPPS pH 8 and then digested with trypsin (1:50; enzyme:protein) for 6 hours at 37° C.

Tandem mass tag (TMT) reagents (ThermoFisher Scientific) were dissolved in anhydrous acetonitrile (ACN) according to manufacturer's instructions. Anhydrous ACN was added to each peptide sample to a final concentration of 30% v/v, and labeling was induced with the addition of TMT reagent to each sample at a ratio of 1:4 peptide:TMT label. The 11-plex labeling reactions were performed for 1.5 hours at rt and the reaction quenched by the addition of 0.3% hydroxylamine for 15 minutes at rt. The sample channels were combined at a 1:1:1:1:1:1:1:1:1:1:1 ratio, desalted using C18 solid phase extraction cartridges (Waters) and analyzed by LC-MS for channel ratio comparison. Samples were then combined using the adjusted volumes determined in the channel ratio analysis and dried down in a speed vacuum. The combined sample was then resuspended in 1% formic acid and acidified (pH 2-3) before being subjected to desalting with C18 SPE (Sep-Pak®, Waters). Samples were then offline fractionated into 96 fractions by high pH reverse-phase HPLC (Agilent LC1260) through an aeris peptide xb-c18 column (Phenomenex®) with mobile phase A containing 5% acetonitrile and 10 mM $NH_4HCO_3$ in LC-MS grade $H_2O$, and mobile phase B containing 90% acetonitrile and 10 mM $NH_4HCO3$ in LC-MS grade $H_2O$ (both pH 8.0). The 96 resulting fractions were then pooled in a non-continuous manner into 24 fractions and every fraction was used for subsequent mass spectrometry analysis.

Data were collected using an Orbitrap Fusion™ Lumos™ mass spectrometer (ThermoFisher Scientific, San Jose, CA, USA) coupled with a Proxeon EASY-nLC™1200 LC pump (ThermoFisher Scientific). Peptides were separated on a 50 cm and 75 mm inner diameter EASY-Spray™ column (ES803a, ThermoFisher Scientific). Peptides were separated using a 190 minute gradient of 6-27% acetonitrile in 1.0% formic acid with a flow rate of 300 nL/min.

Each analysis used an MS3-based TMT method as described previously (McAlister et al., Anal. Chem. 86:7150-7158 (2014)). The data were acquired using a mass range of m/z 340-1350, resolution 120,000, AGC target 5×105, maximum injection time 100 ms, dynamic exclusion of 120 seconds for the peptide measurements in the Orbitrap. Data dependent MS2 spectra were acquired in the ion trap with a normalized collision energy (NCE) set at 35%, AGC target set to 1.8×104 and a maximum injection time of 120 ms. MS3 scans were acquired in the Orbitrap with a HCD collision energy set to 55%, AGC target set to 2×105, maximum injection time of 150 ms, resolution at 50,000 and with a maximum synchronous precursor selection (SPS) precursors set to 10.

LC-MS Data Analysis

Proteome Discoverer 2.2 (ThermoFisher Scientific) was used for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 10 ppm, fragment ion mass tolerance of 0.6 Da, static alkylation of cysteine (57.02146 Da), static TMT labeling of lysine residues and N-termini of peptides (229.16293 Da), variable phosphorylation of serine, threonine and tyrosine (79.966 Da), and variable oxidation of methionine (15.99491 Da). TMT reporter ion intensities were measured using a 0.003 Da window around the theoretical m/z for each reporter ion in the MS3 scan. Peptide spectral matches with poor quality MS3 spectra were excluded from quantitation (summed signal-to-noise across 10 channels <200 and precursor isolation specificity <0.5). Only proteins containing at least two unique peptides identified in the experiment were included in final quantitation.

Figure 5A:
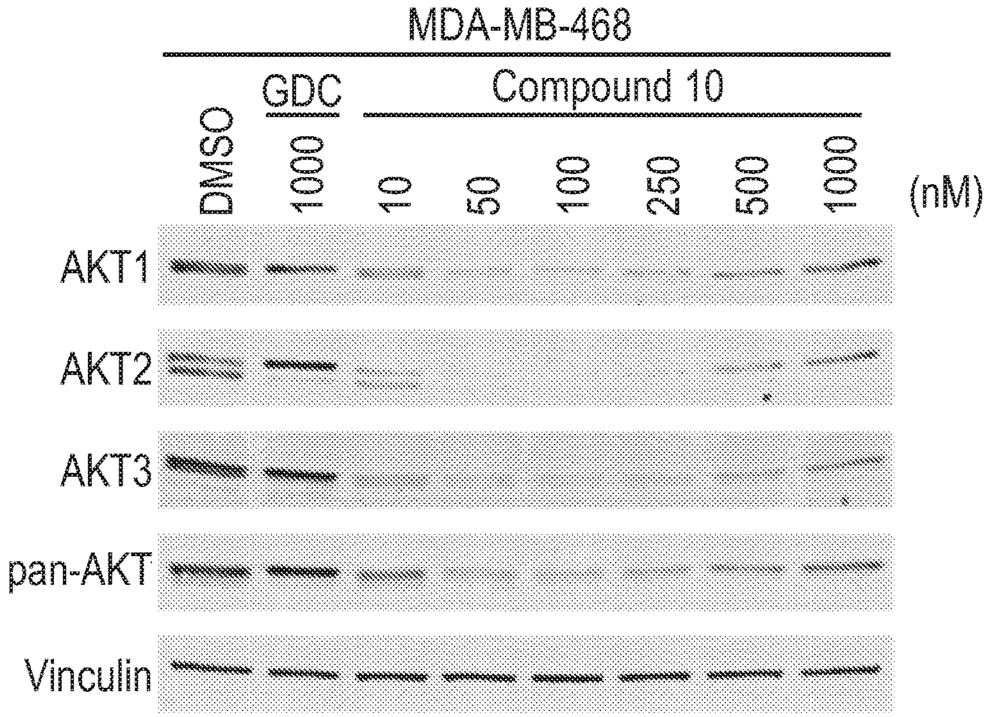
FIG. 5A is an immunoblot that shows the degradation of AKT1, AKT2, AKT3, pan-AKT, and Vinculin in MDA-MB-468 cells after 12-hour treatment with DMSO, GDC-0068 (GDC), or inventive bifunctional compound 10 at the concentrations indicated (n=4).
Figure 5B:
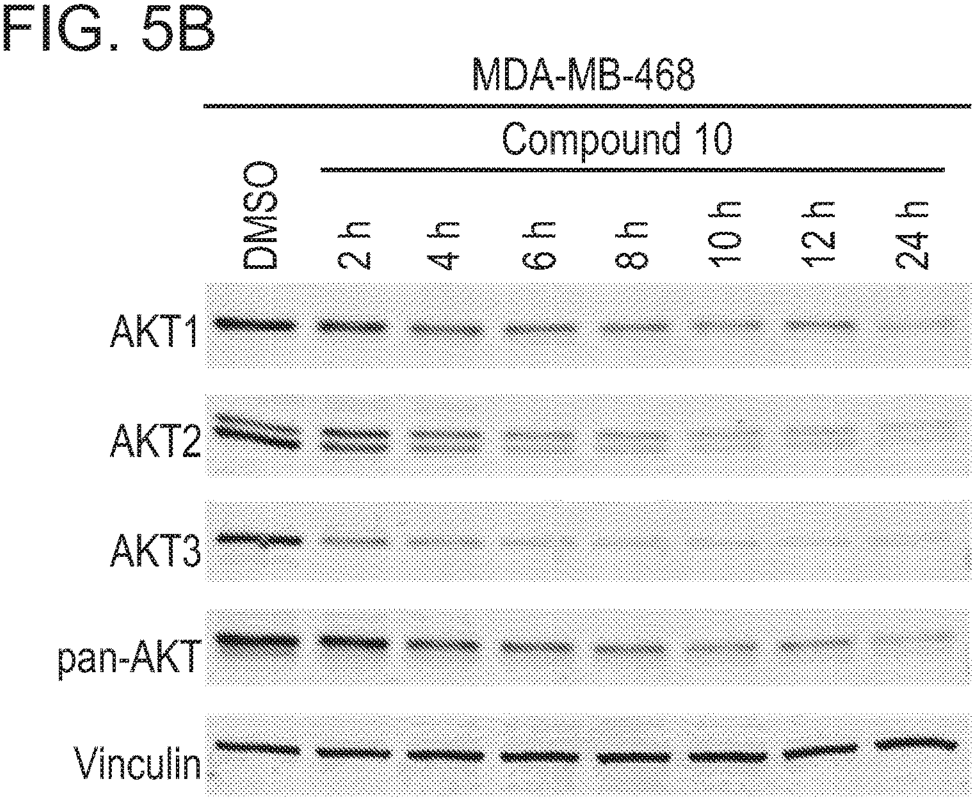
FIG. 5B is an immunoblot that shows the degradation of AKT1, AKT2, AKT3, pan-AKT, and Vinculin in MDA-MB-468 cells after treatment with inventive bifunctional compound 10 (250 nM) at indicated times or DMSO (24 hours) (n=4).

The data illustrated in FIG. 5A show that inventive bifunctional compound 10 induced potent degradation of all three AKT isoforms in a dose-dependent manner after a 12-hour treatment, with maximal degradation observed between 100 and 250 nM. Treatment of MDA-MB-468 cells with 250 nM of inventive bifunctional compound 10 over time revealed partial degradation of all AKT isoforms within 4 h and progressive loss of AKT abundance out to 24 h (FIG. 5B).

Figure 5C:
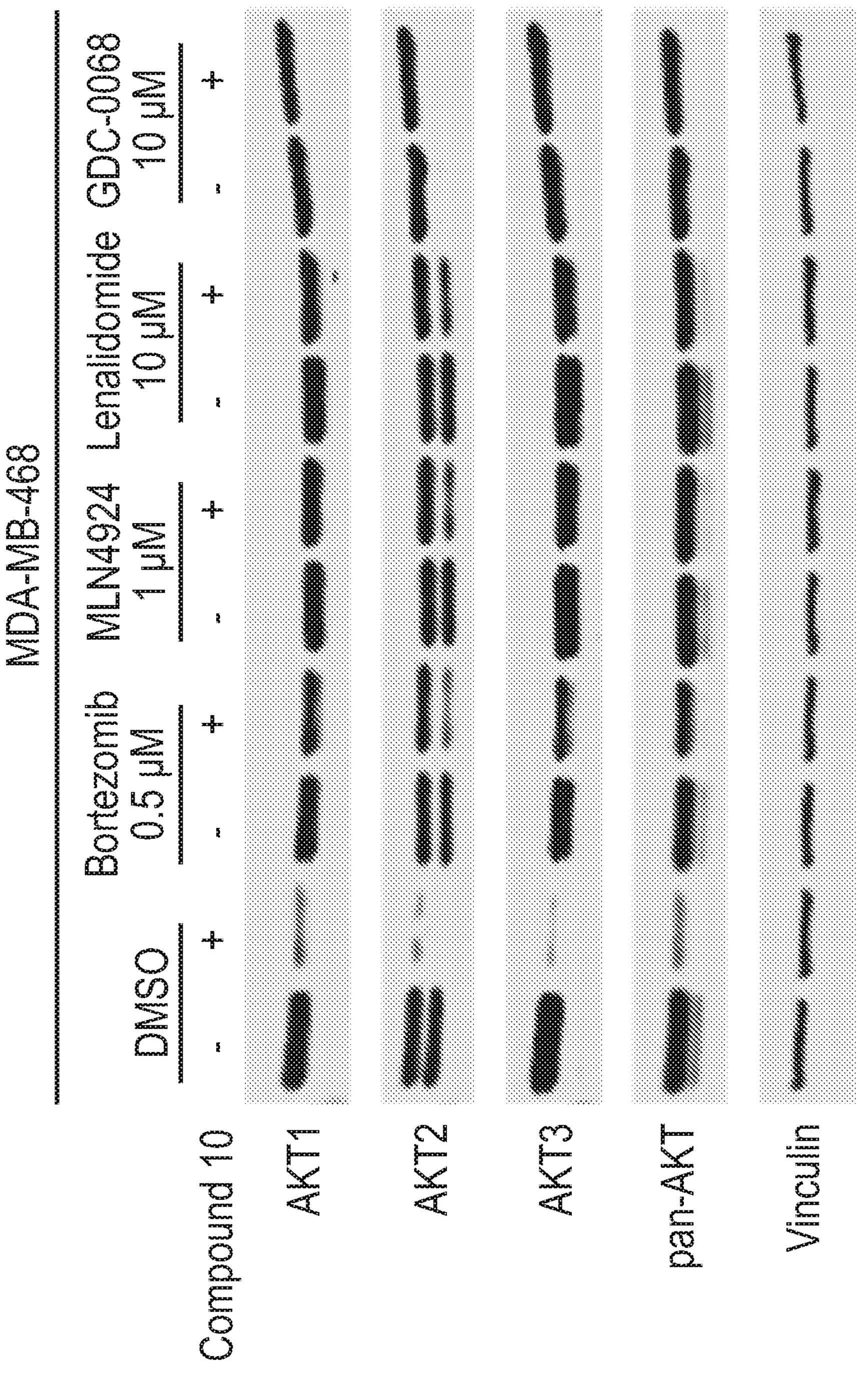
FIG. 5C is an immunoblot that shows the degradation of AKT1, AKT2, AKT3, pan-AKT, and Vinculin after 12-hour co-treatment of MDA-MB-468 cells with DMSO, bortezomib (0.5 mM), MLN-4924 (1 mM), lenalidomide (10 mM), or GDC-0068 (10 mM) and either inventive bifunctional compound 10 (250 nM) or DMSO (n=4).

Co-treatment of inventive bifunctional compound 10 with bortezomib, a proteasome inhibitor, or MLN-4924, an NEDD8-activating enzyme inhibitor that prevents neddylation required for the function of cullin RING ligases, such as CRL4CRBN (Soucy et al., Clin. Cancer Res. 15:3912-3916 (2009)), prevented AKT destabilization, indicating that degradation was dependent on the ubiquitin-proteasome system (FIG. 5C). Co-treated inventive bifunctional compound 10 with excess quantities of either GDC-0068 or lenalidomide to compete for binding to AKT or CRBN, respectively, both of which prevented AKT degradation, demonstrating that engagement to both AKT and CRBN is required for inventive bifunctional compound 10 induced AKT degradation (FIG. 5C).

Figure 5D:
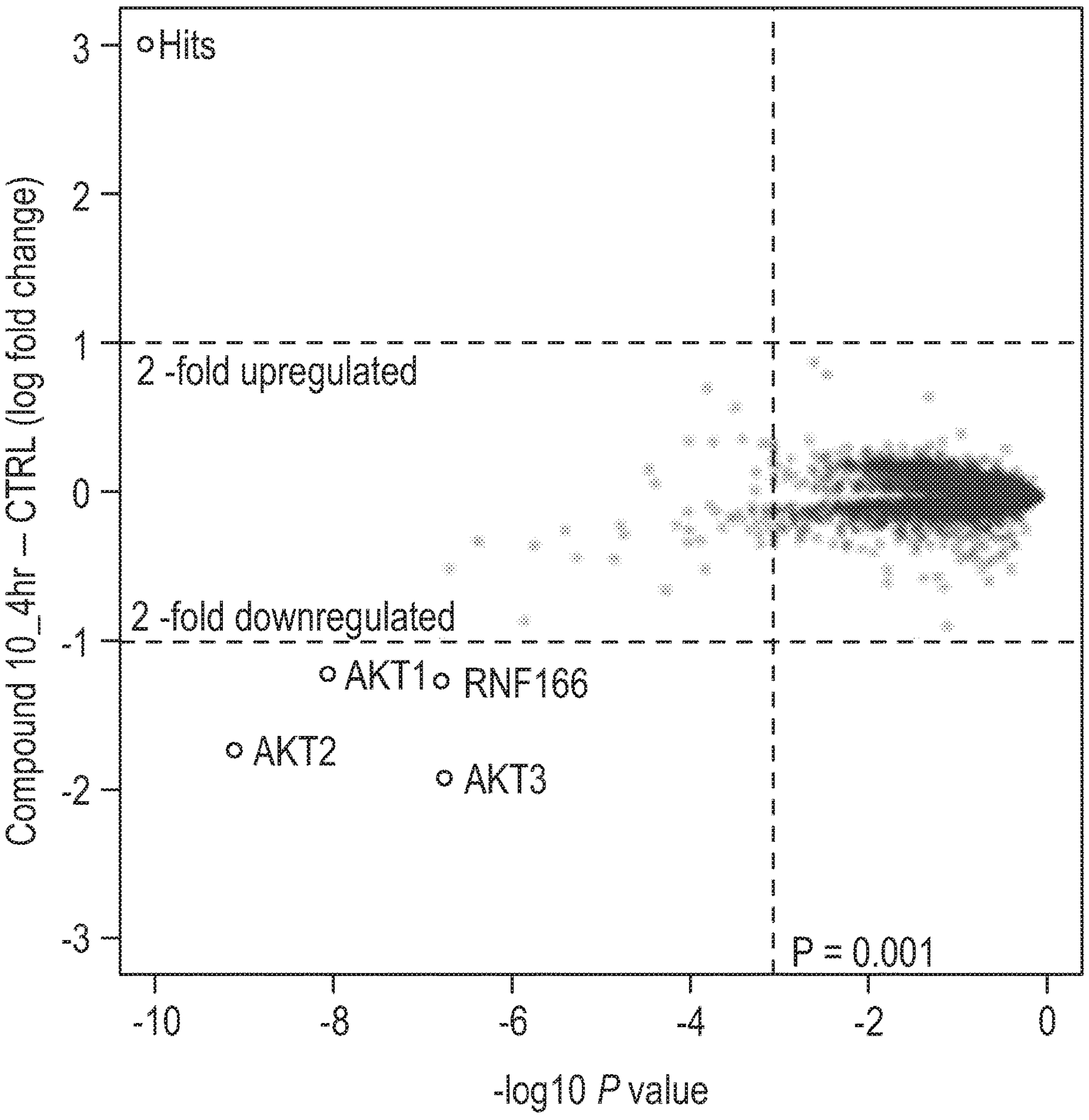
FIG. 5D is scatterplot depicting the change in relative protein abundance of inventive bifunctional compound 10 (250 nM, 4 h)-treated MOLT4 cells compared with DMSO vehicle control-treated cells. The log 2 fold change (log 2 FC) is shown on the y-axis and negative log 10 p value (−log 10 p value) on the x-axis for three independent biological replicates of each treatment.

To broadly assess degrader selectivity, MOLT4 cells, a cell line that is amenable to proteomics and expresses all three AKT isoforms, were treated with 250 nM of inventive bifunctional compound 10 for 4 hours and an unbiased, multiplexed mass spectrometry-based proteomic analysis was performed as described above. This analysis identified significant downregulation of all three AKT isoforms, as well as RNF166, a ring-finger protein known to be downregulated by lenalidomide treatment (FIG. 5D) (Kronke et al., Nature 523:183-188 (2015)).

Figure 6A:
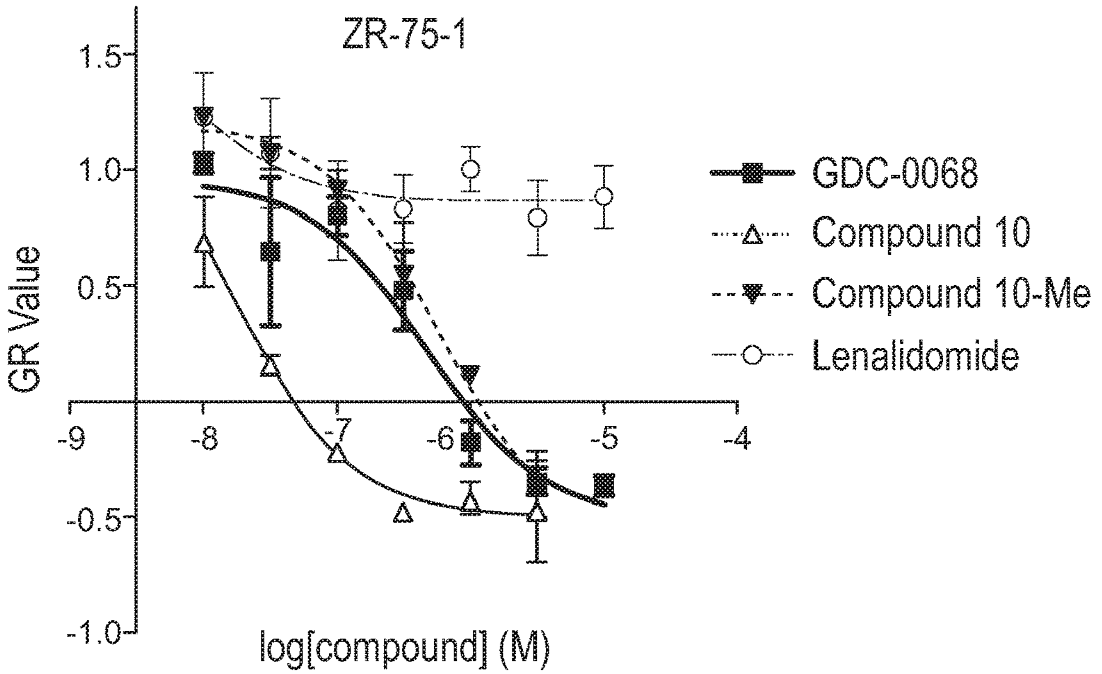
FIG. 6A-FIG. 6F are a set of graphs that show growth inhibition rate (GR) values across concentrations in ZR-75-1 (FIG. 6A), T47D (FIG. 6B), LNCaP (FIG. 6C), MCF-7 (FIG. 6D), MDA-MB-468 (FIG. 6E), and HCC1937 (FIG. 6F) cells after 72-hour treatment with GDC-0068 (blue), inventive bifunctional compound 10 (red), bifunctional compound 10-Me (negative control) (green), and lenalidomide (orange). Error bars represent the standard deviation of three technical replicates.
Figure 6B:
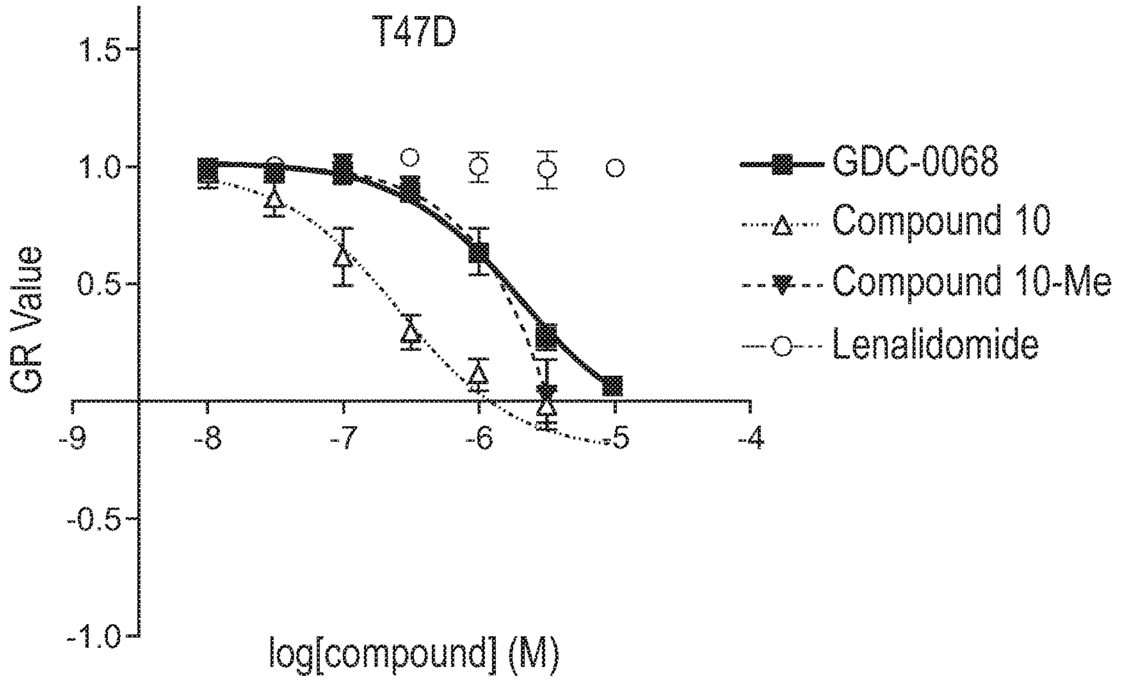
Figure 6C:
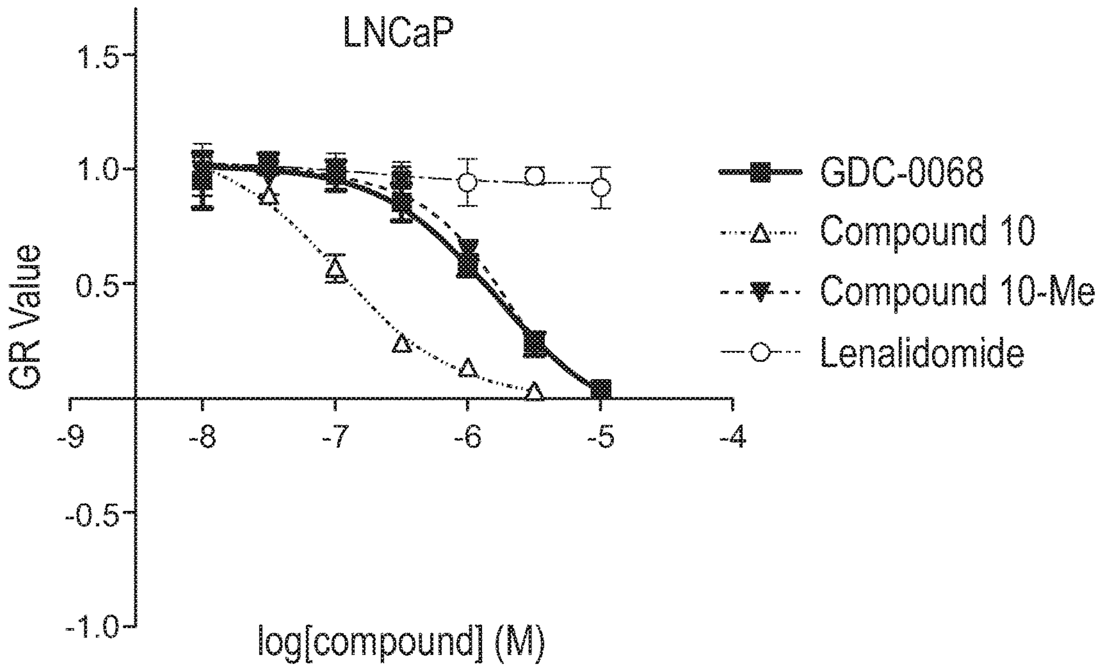
Figure 6D:
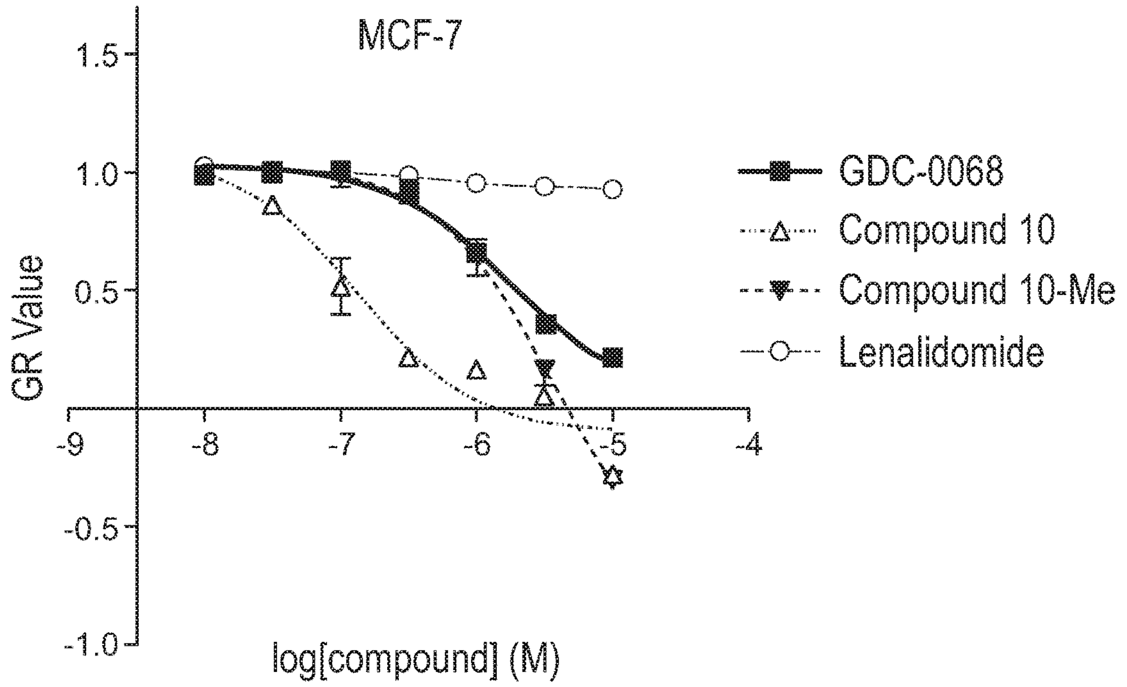

The data illustrated in FIG. 6A show that the anti-proliferative effect of inventive bifunctional compound 10 was degradation dependent, as bifunctional compound 10-Me, which is incapable of binding CRBN, was significantly less potent (GR50=413 nM) than inventive bifunctional compound 10 and had a comparable GR50 value with GDC-0068. Similar trends were seen in the other cell lines sensitive to AKT inhibition, with 8- to 14-fold lower GR50 values for inventive bifunctional compound 10 in comparison with GDC-0068 (FIG. 6A-FIG. 6D). In addition, lenalidomide, used as a control for RNF166, IKZF1, and IKZF3 degradation, did not have strong anti-proliferative effects, suggesting that the enhanced anti-proliferative effects were due to AKT degradation (FIG. 6A-FIG. 6D).

Figure 6E:
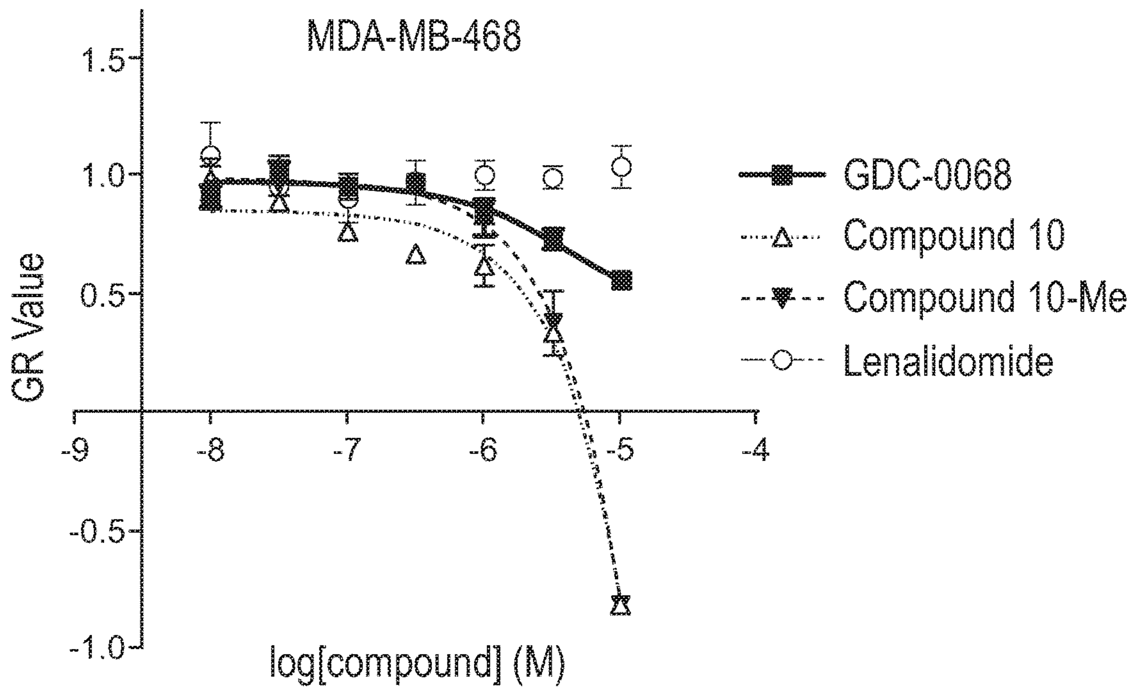
Figure 6F:
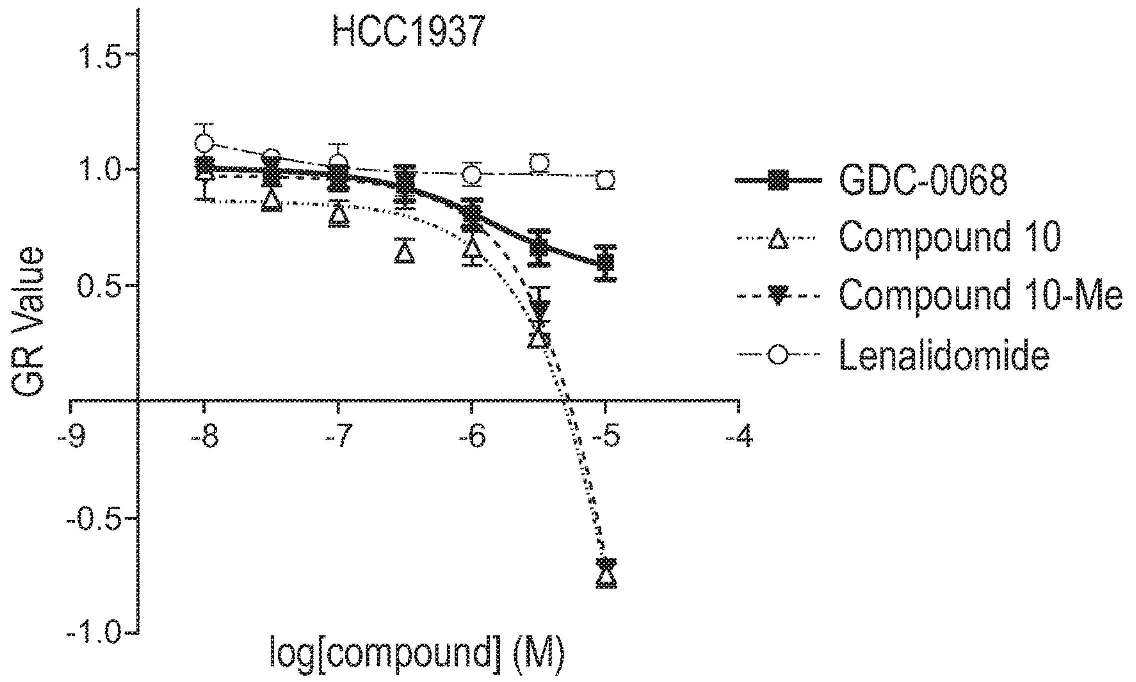

Although inventive bifunctional compound 10 displayed enhanced anti-proliferative effects compared with GDC-0068 in MDA-MB-468 and HCC1937 cells, there were no apparent differences in GR50 values between inventive bifunctional compound 10 and bifunctional compound 10-Me (FIG. 6E-FIG. 6F). Thus, the anti-proliferative effects of inventive bifunctional compound 10 in these cell lines were likely due to off-target effects unrelated to AKT degradation that manifest at elevated concentrations of inventive bifunctional compound 10 and bifunctional compound 10-Me. This is consistent with previous studies reporting resistance of MDA-MB-468 and HCC1937 to AKT inhibition (Lin et al., Clin. Cancer Res. 19:1760-1772 (2013)), and indicates that AKT degradation has similar phenotypic effects as AKT inhibition in these cell lines. Overall, the data show that inventive bifunctional compound 10 suppressed proliferation more potently than GDC-0068, and highlighted the potential therapeutic value of targeted AKT degradation.

Figure 7A:
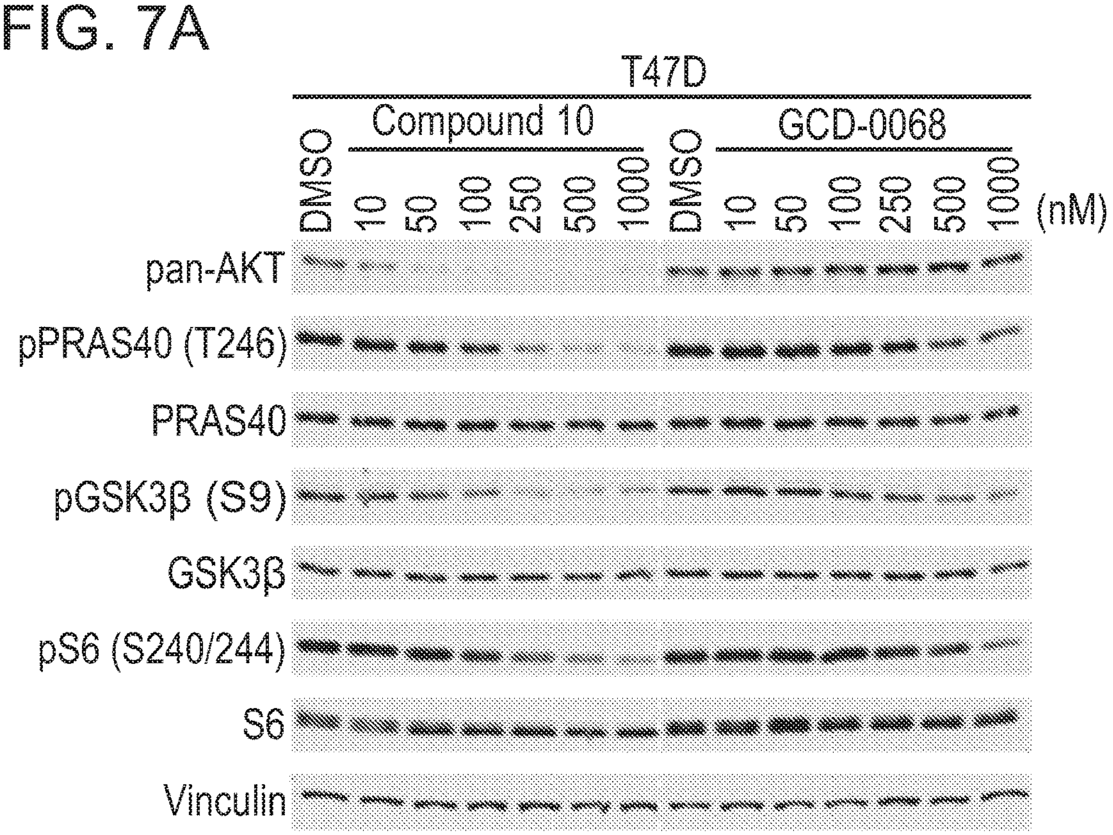
FIG. 7A is an immunoblot that shows the degradation of pan-AKT, phospho-PRAS40 (T246), total PRAS40, phospho-GSK3I3 (S9), total GSK3I3, phospho-S6 (S240/244), total S6, and Vinculin after treating T47D cells for 24 hours with DMSO, inventive bifunctional compound 10, or GDC-0068 at the concentrations indicated (n=3).
Figure 7B:
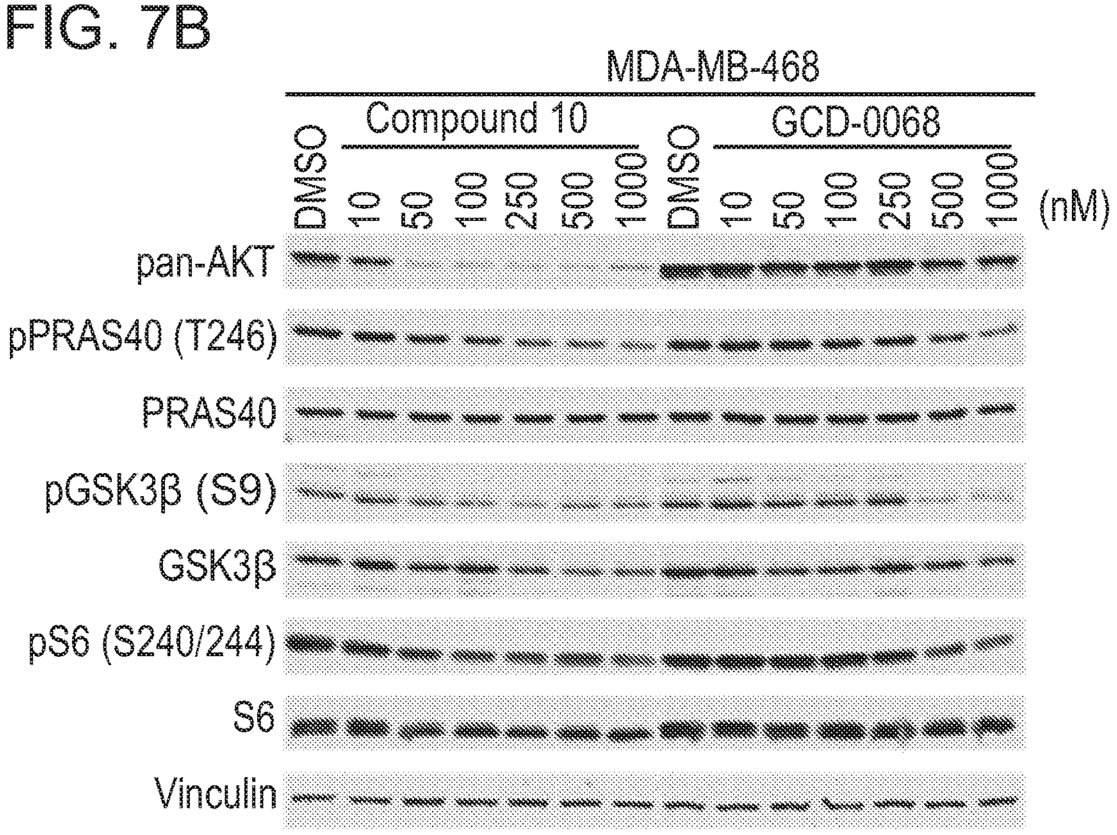
FIG. 7B is an immunoblot that shows the degradation of pan-AKT, phospho-PRAS40 (T246), total PRAS40, phospho-GSK3I3 (S9), total GSK3I3, phospho-S6 (S240/244), total S6, and Vinculin after treating MDA-MB-468 cells for 24 hours with DMSO, inventive bifunctional compound 10, or GDC-0068 at the concentrations indicated (n=3).

To test whether these effects were generalizable across distinct cell lines, we also compared the effects of inventive bifunctional compound 10 and GDC-0068 in MDA-MB-468 and T47D cells were compared (FIG. 7A-FIG. 7B). Inventive bifunctional compound 10 significantly reduced phosphorylation of PRAS40, GSK3I3, and S6 at 250 nM (FIG. 7A), while weaker responses were seen with equivalent doses of GDC-0068 (FIG. 7B).

Figure 7C:
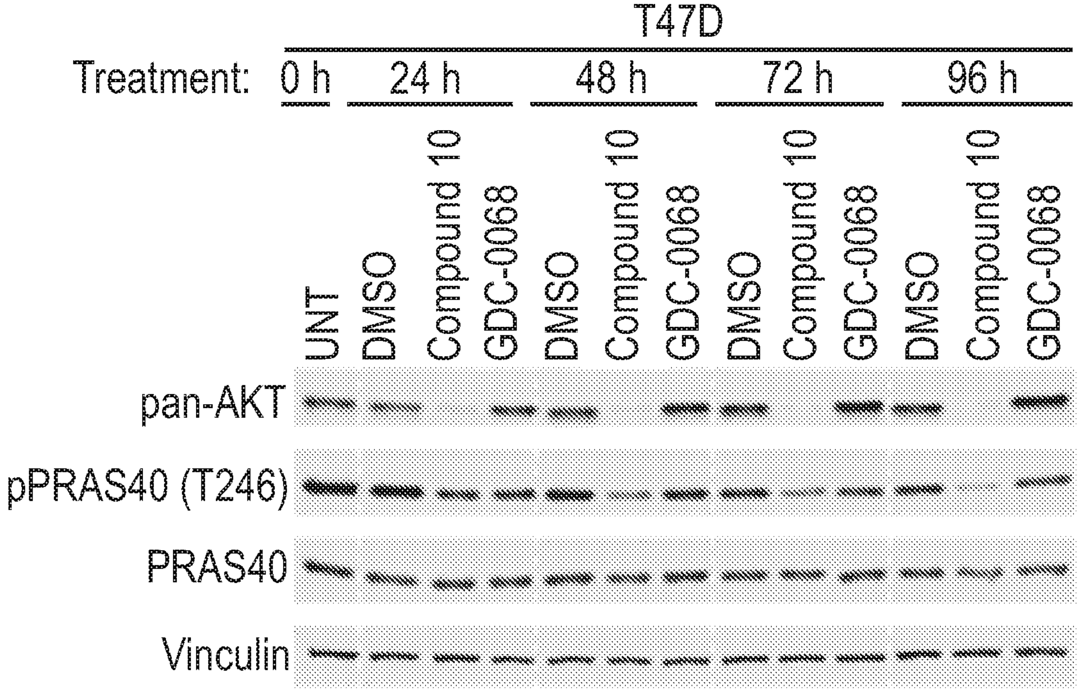
FIG. 7C is an immunoblot that shows the degradation of pan-AKT, phospho-PRAS40 (T246), total PRAS40, and Vinculin after treatment of T47D cells with 250 nM of inventive bifunctional compound 10 or GDC-0068 at the time points indicated (n=3).
Figure 7D:
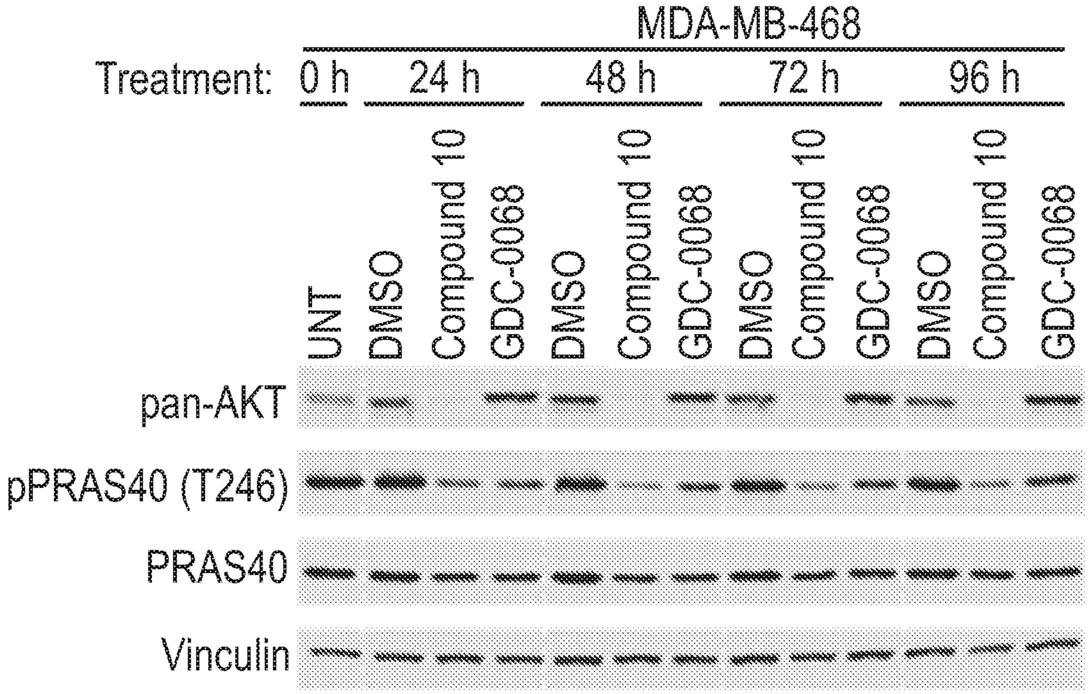
FIG. 7D is an immunoblot that shows the degradation of pan-AKT, phospho-PRAS40 (T246), total PRAS40, and Vinculin after treatment of MDA-MB-468 cells with 250 nM of inventive bifunctional compound 10 or GDC-0068 at the time points indicated (n=3).

Notably, the data illustrated in FIG. 7C-FIG. 7D show that inventive bifunctional compound 10 promoted sustained destabilization of all three AKT isoforms for at least 96 hours after treatment with 250 nM of inventive bifunctional compound 10 in both T47D and MDA-MB-468 cells. This durable AKT degradation resulted in sustained inhibition of downstream signaling, as pPRAS40 levels were also significantly reduced for up to 96 hours (FIG. 7C). By contrast, treatment with an equivalent dose of GDC-0068 not only resulted in less-pronounced inhibition of pPRAS40, but the duration of this effect was also shorter FIG. 7D).

Figure 7E:
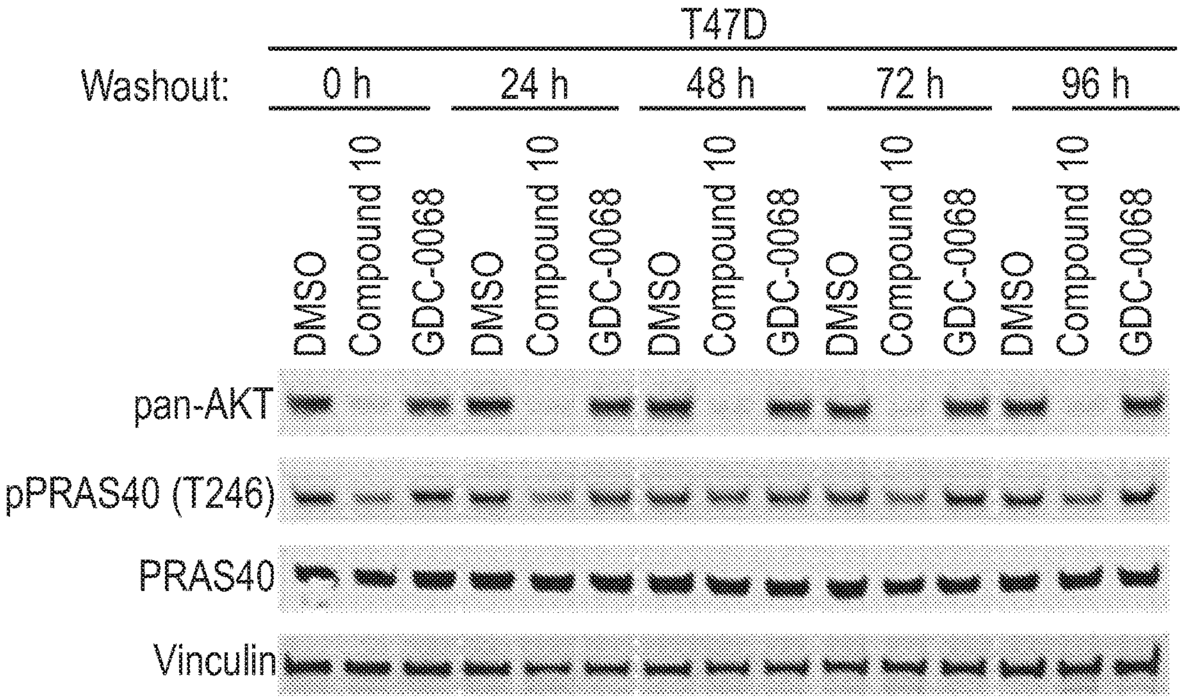
FIG. 7E is an immunoblot that shows the degradation of pan-AKT, phospho-PRAS40 (T246), total PRAS40, and Vinculin in T47D or MDA-MB-468 cells treated for 12 hours with inventive bifunctional compound 10 or GDC-0068 (250 nM), followed by washout for indicated times (n=4). Solid vertical white line indicates samples run on separate gels.
Figure 7F:
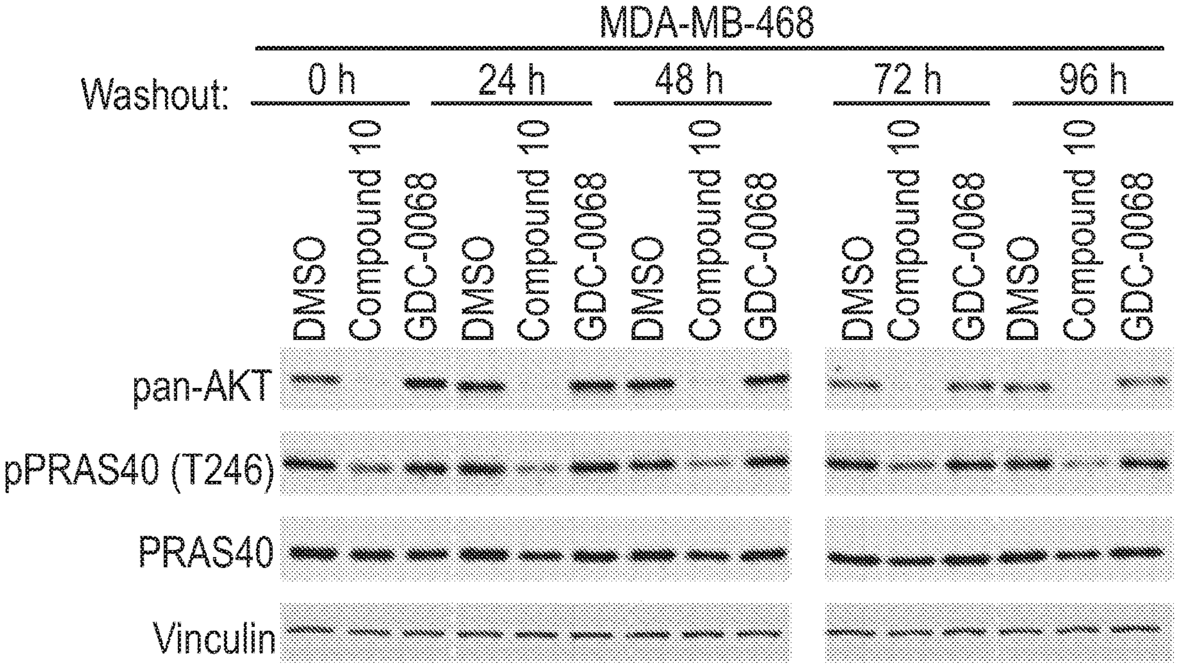
FIG. 7F is an immunoblot that shows the degradation of pan-AKT, phospho-PRAS40 (T246), total PRAS40, and Vinculin in T47D or MDA-MB-468 cells treated for 12 hours with inventive bifunctional compound 10 or GDC-0068 (250 nM), followed by washout for indicated times (n=4). Solid vertical white line indicates samples run on separate gels.

To further characterize the mechanism underlying the extended duration of AKT degradation induced by inventive bifunctional compound 10, compound washout experiments after 12 h of treatment with either 250 nM of inventive bifunctional compound 10 or GDC-0068 were performed. The data illustrated in FIG. 7E-FIG. 7F show no detectable rebound of AKT levels for up to 96 h after washout in inventive bifunctional compound 10-treated cells, suggesting that the re-synthesis rate of AKT is slow. Consistently, inventive bifunctional compound 10 potently suppressed levels of pPRAS40 for up to 96 hours after washout (FIG. 7E), while washout in GDC-0068-treated cells resulted in rebound of pPRAS40, as would be expected of a reversible inhibitor (FIG. 7F). Taken together, the data suggest that inventive bifunctional compound 10-mediated AKT degradation resulted in more potent and durable pharmacological effects than AKT inhibition.

All publications cited in the specification, including patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention described herein has been described with reference to particular embodiments, it is to be understood that these embodiments are merely illustrative of the principle and applications described herein. It is therefore to be understood that numerous modifications may be made to the illustrative embodiments and that other arrangements may be devised without departing from the spirit and scope of the various embodiments described herein as defined by the appended claims.

What is claimed is:

1. A bifunctional compound, having a structure represented by formula I:

(I)

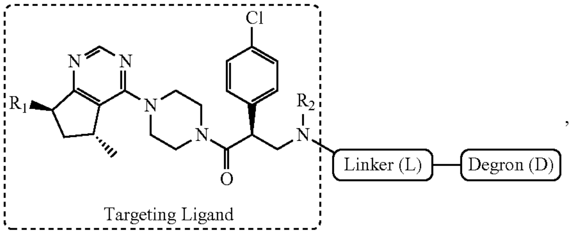

, wherein the targeting ligand binds AKT1, 2 and 3, and $R_1$ is H or OH;

$R_2$ is H, methyl, ethyl, or isopropyl;

the linker is represented by formula L10:

(L10)

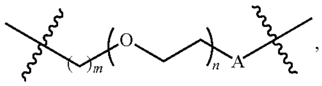

, wherein

A is absent, CO, or $NR_3COCH_2$, wherein $R_3$ is H or methyl;

m is independently 1 to 10;

and n independently is 0, 1, 2, or 3; and the degron is represented by any of structures D1a-D1h and D2a-D2e:

(D1a)

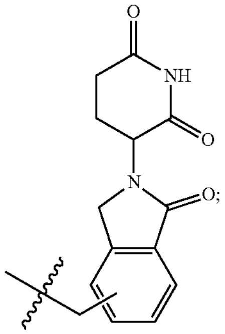

(D1b)

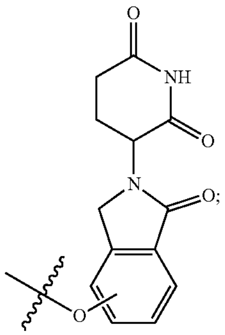

-continued (D1c)

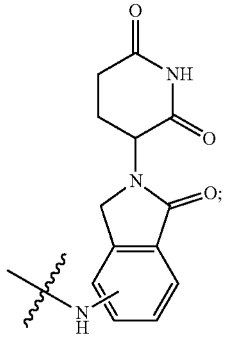

(D1d)

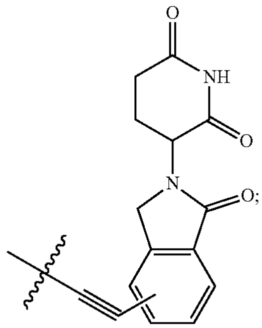

(D1e)

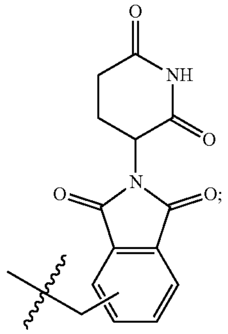

(D1f)

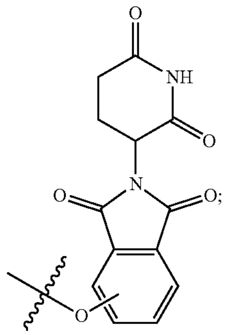

-continued
(D1g)
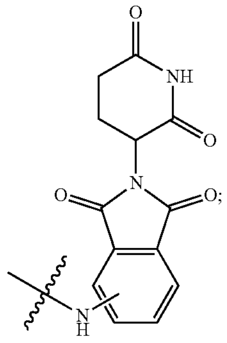
and
(D1h)
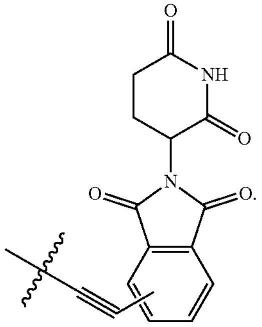
(D2a)
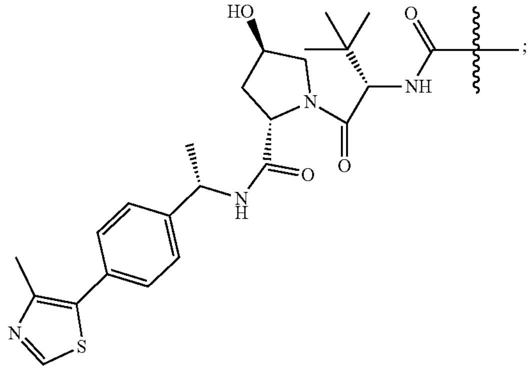
(D2b)
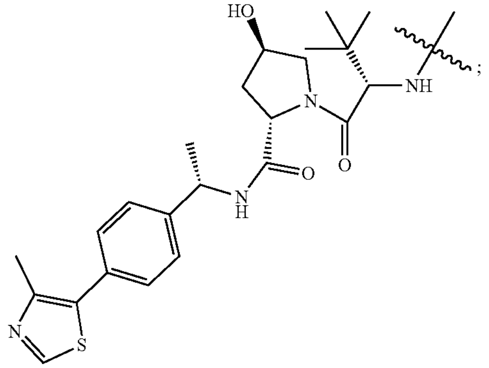
-continued
(D2c)
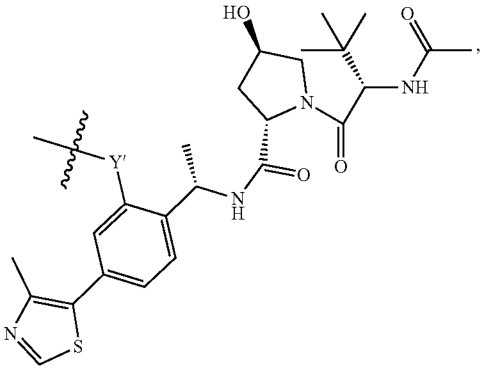
wherein Y' is a bond, NH, O or $CH_2$;
(D2d)
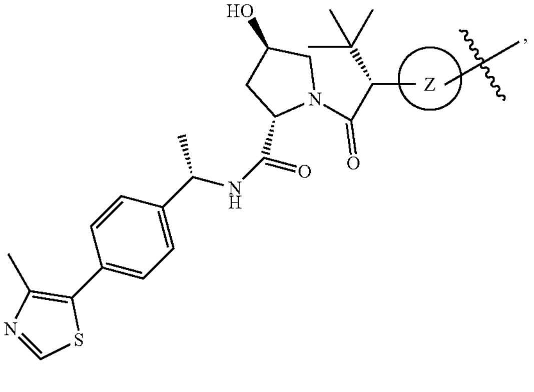
wherein Z is a cyclic group;
and
(D2e)
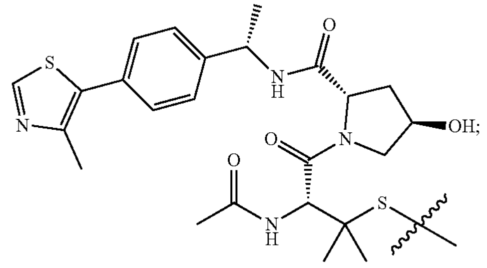
or a pharmaceutically acceptable salt or stereoisomer thereof.
2. The bifunctional compound of claim 1, wherein $R_1$ and $R_2$ are H, and the targeting ligand is represented by structure (TL-1):

(TL-1)

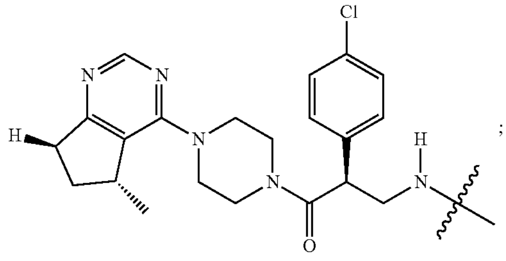

;

or wherein $R_1$ is H and $R_2$ is methyl, and the targeting ligand is represented by structure (TL-2):

(TL-2)

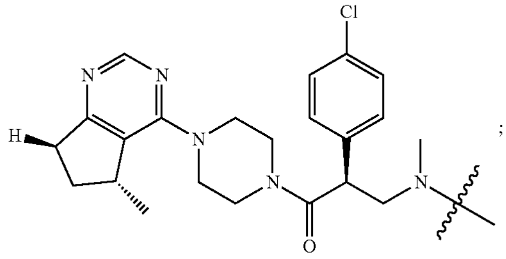

;

or wherein $R_1$ is OH and $R_2$ is H, and the targeting ligand is represented by structure (TL-3):

(TL-3)

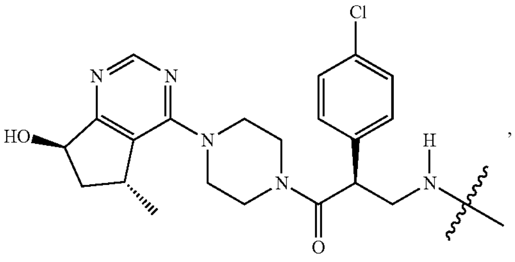

, or wherein $R_1$ is OH and $R_2$ is methyl, and the targeting ligand is represented by structure (TL-4):

(TL-4)

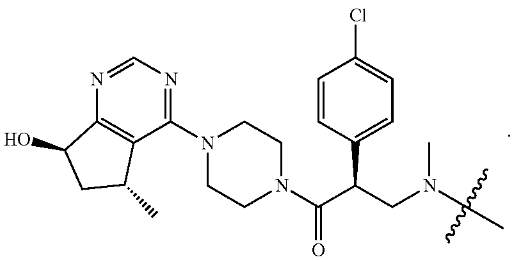

.

3. The bifunctional compound of claim 2, wherein the targeting ligand is represented by structure (TL-1) or (TL-2):

(TL-1)

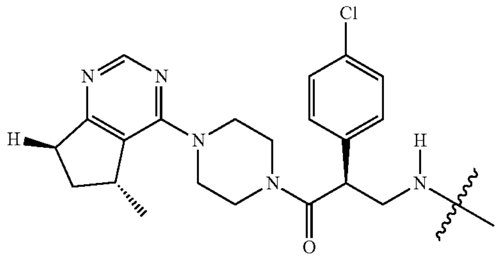

or (TL-2)

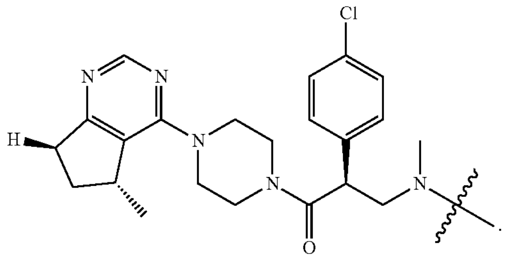

4. The bifunctional compound of claim 2, wherein the targeting ligand is represented by structure (TL-3):

(TL-3)

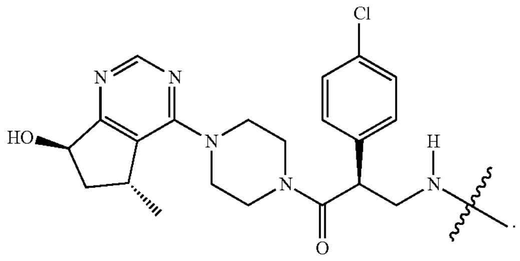

5. The bifunctional compound of claim 2, wherein the targeting ligand is represented by structure (TL-4):

(TL-4)

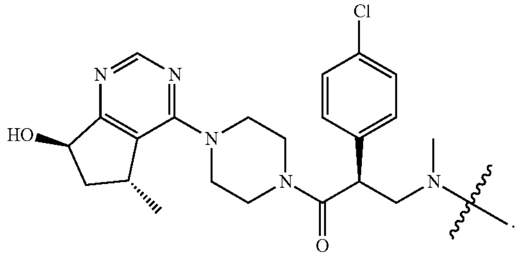

6. The bifunctional compound of claim 1, wherein the linker is represented by any one of structures:

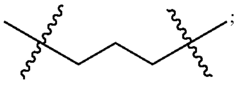

;

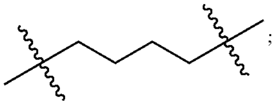

;

-continued
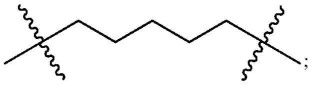
;
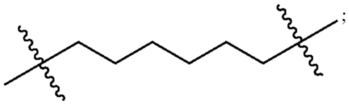
;
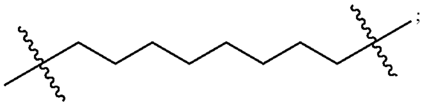
;
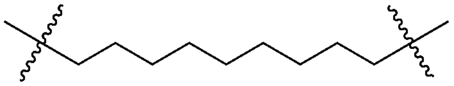
;
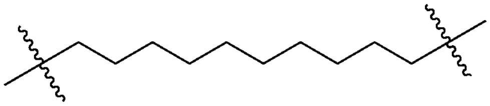
;
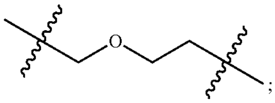
;
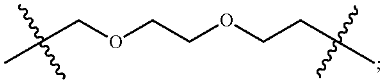
;
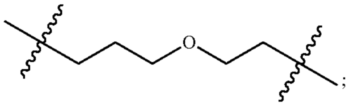
;
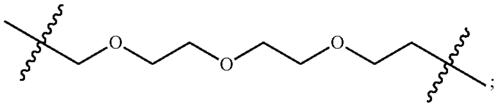
;
-continued
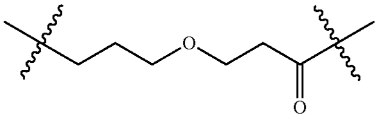
;
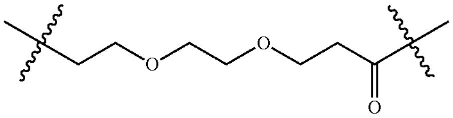
;
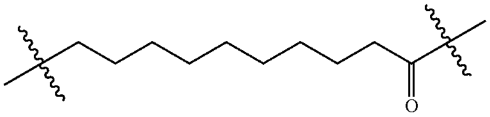
;
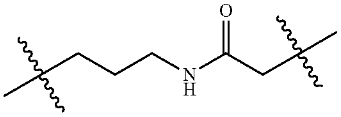
;
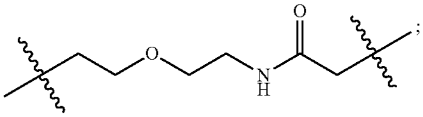
;
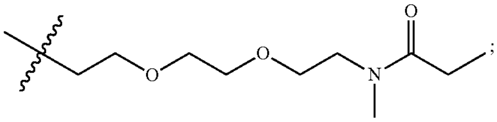
; and
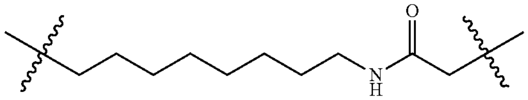
.
7. The bifunctional compound of claim 1, which is represented by any one of structures I-6 to I-21:
(I-6)
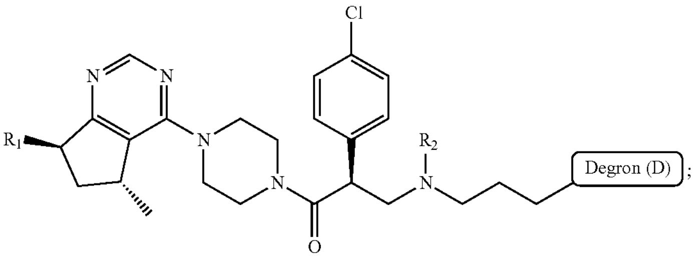
;
(I-7)
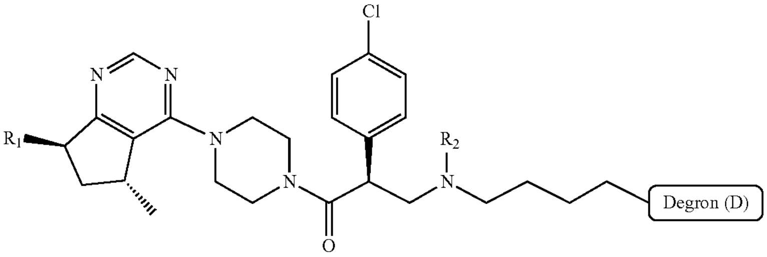
;

-continued
(I-8)
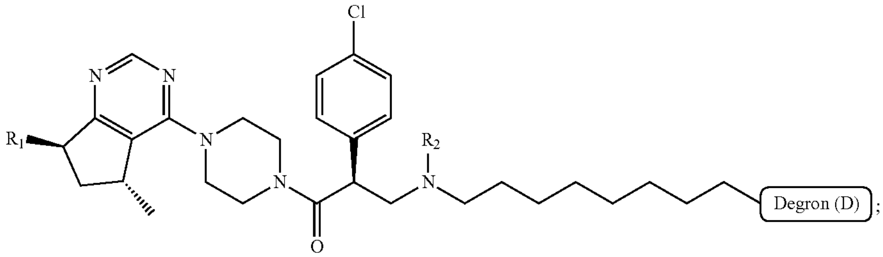
;
(I-9)
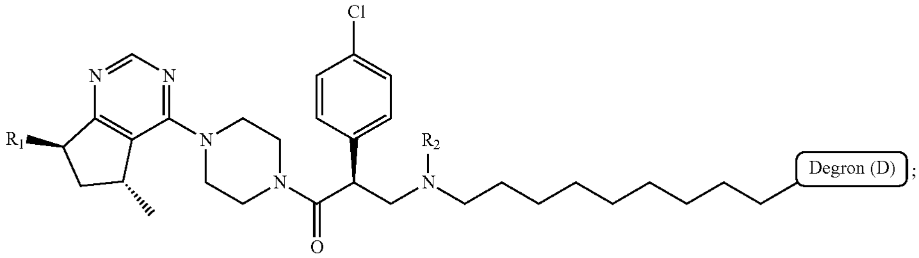
;
(I-10)
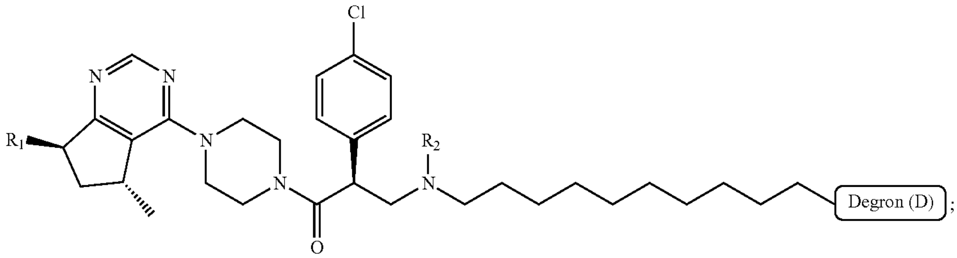
;
(I-11)
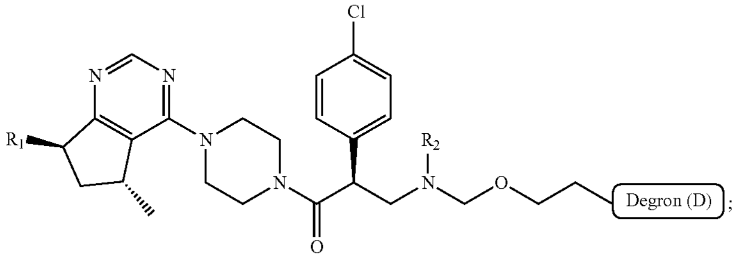
;
(I-12)
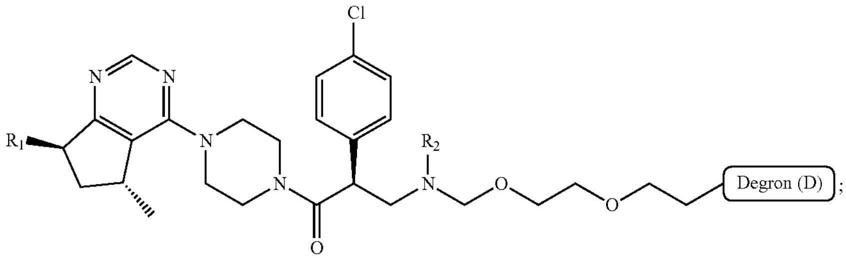
;
(I-13)
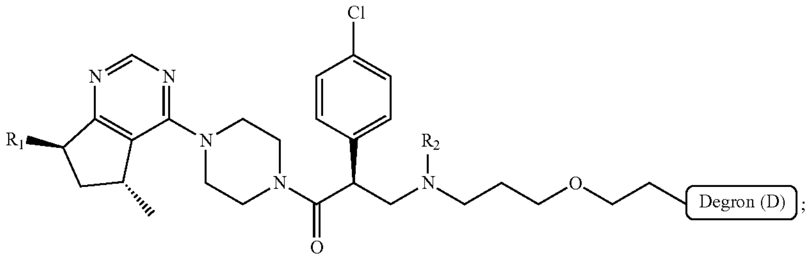
;

-continued
(I-14)
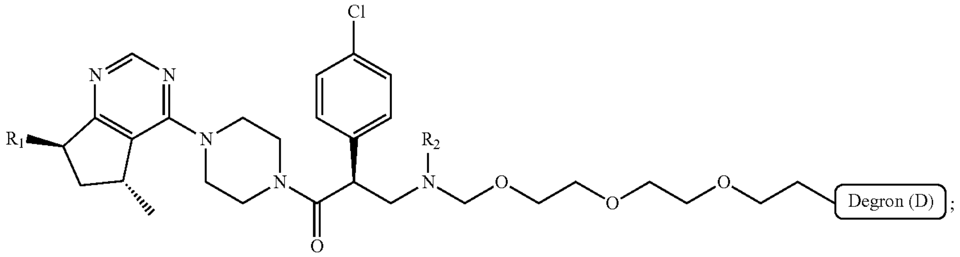
(I-15)
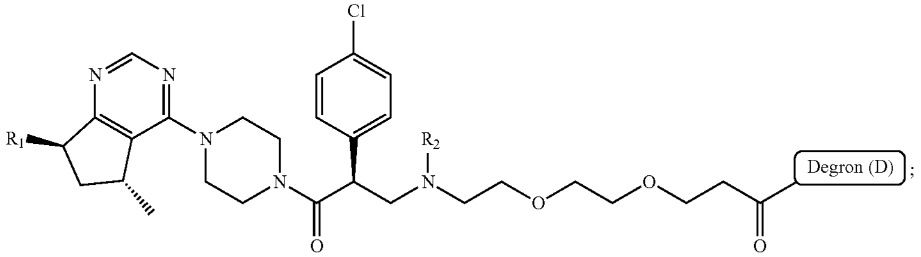
(I-16)
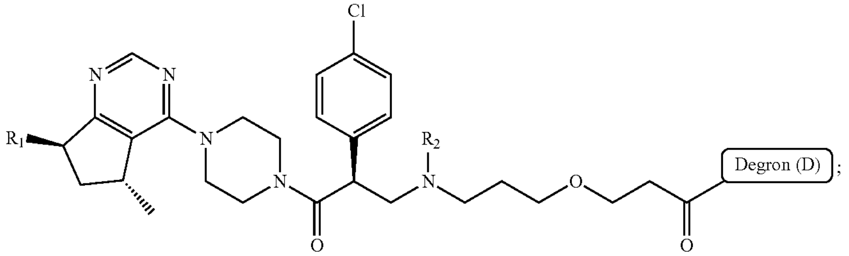
(I-17)
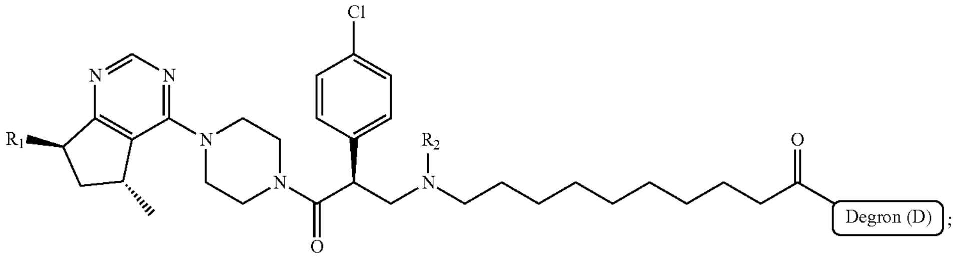
(I-18)
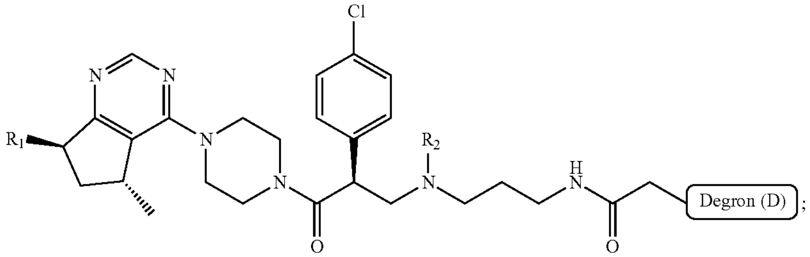
(I-19)
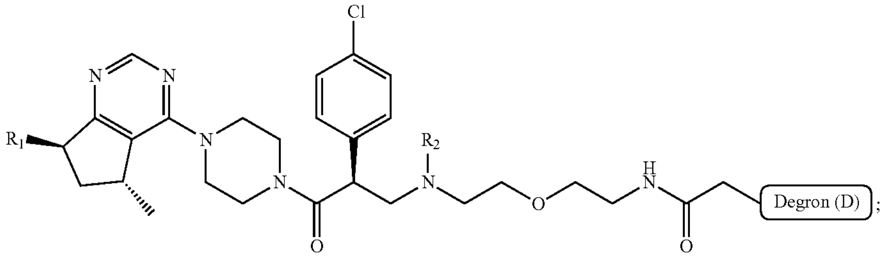

-continued
(I-20)
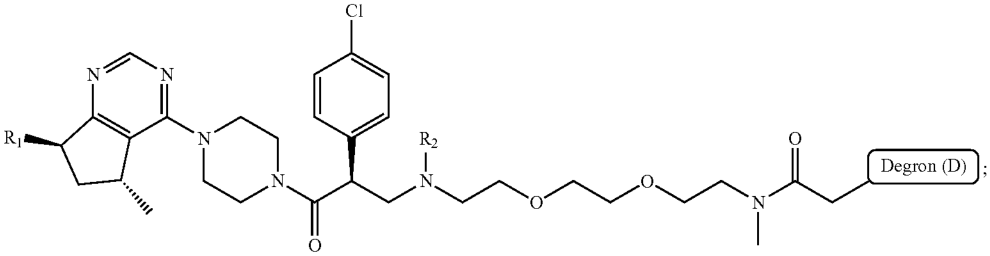
; and
(I-21)
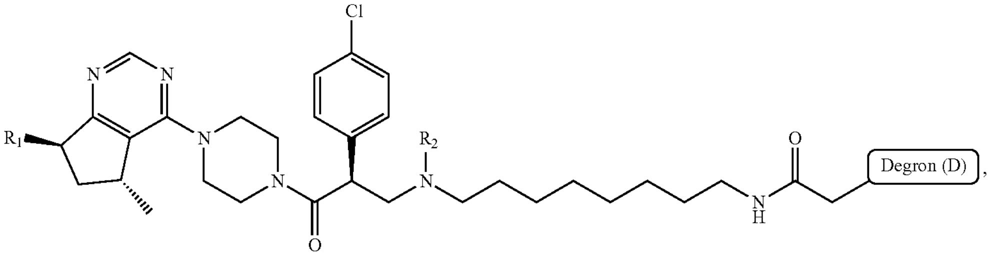
,
or a pharmaceutically acceptable salt or stereoisomer thereof, wherein
$R_1$ is H or OH; and
$R_2$ is H, methyl, ethyl, or isopropyl.
8. The bifunctional compound of claim 1, wherein the degron is represented by any of structures D1a-D1h:
(D1a)
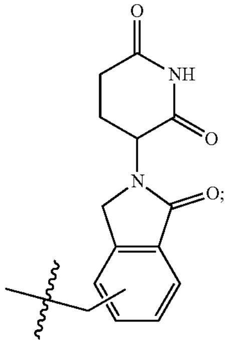
;
(D1b)
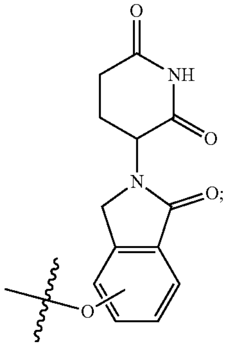
;
-continued
(D1c)
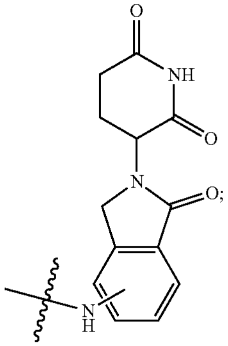
;
(D1d)
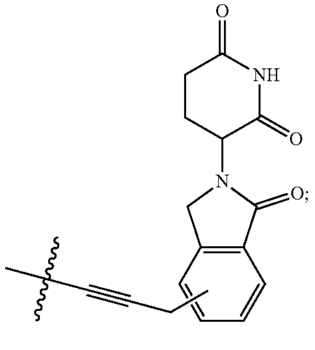
;
(D1e)
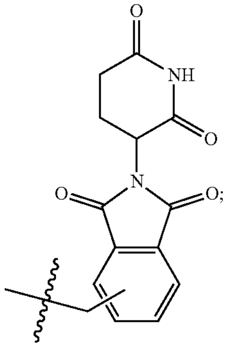
;

(D1f)
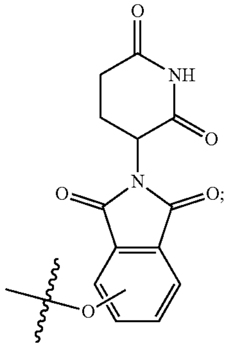
(D1g)
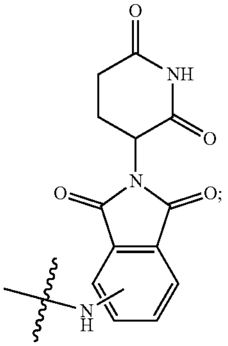
and
(D1h)
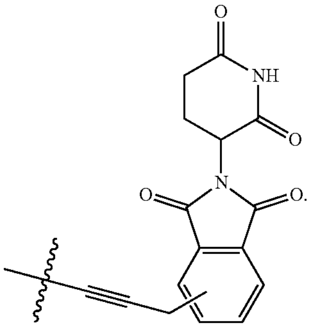
9. The bifunctional compound of claim 1, wherein the degron is represented by any one of structures D2a to D2e:
(D2a)
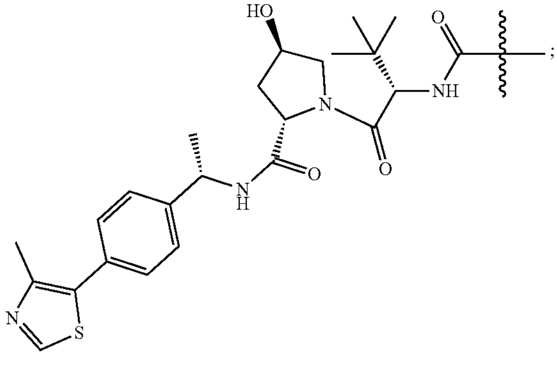
(D2b)
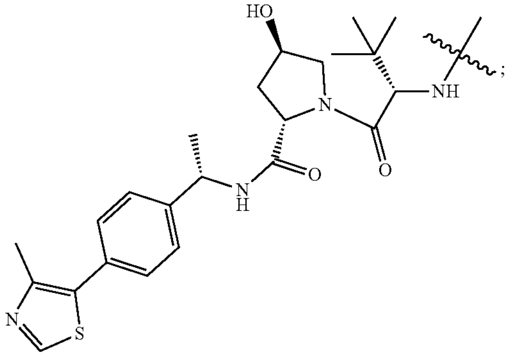
(D2c)
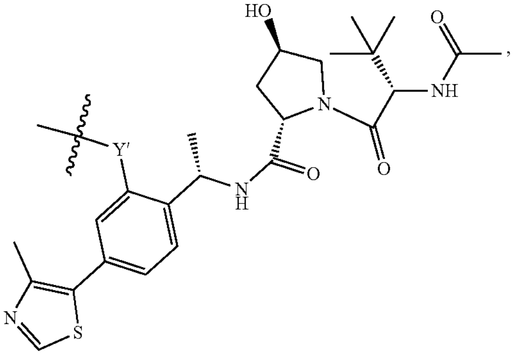
wherein Y' is a bond, NH, O or $CH_2$;
(D2d)
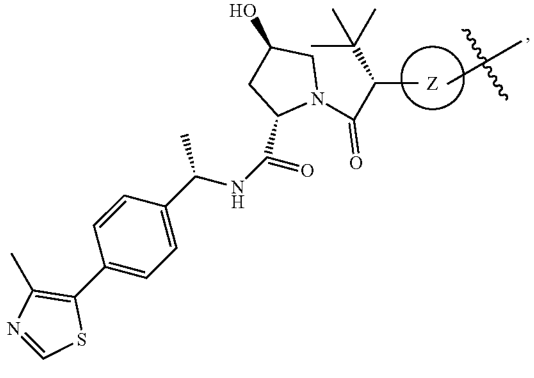

wherein Z is a cyclic group; and
(D2e)
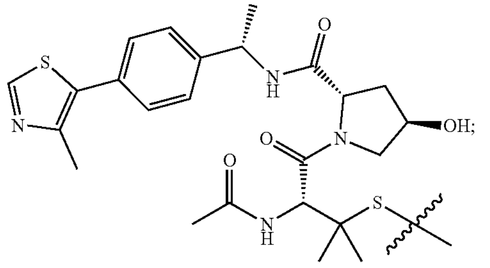
10. The bifunctional compound of claim 1, which is represented by any one of formulae I-22 to I-34:
(I-22)
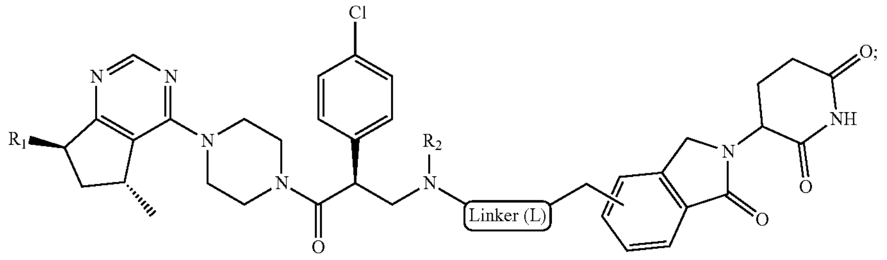
(I-23)
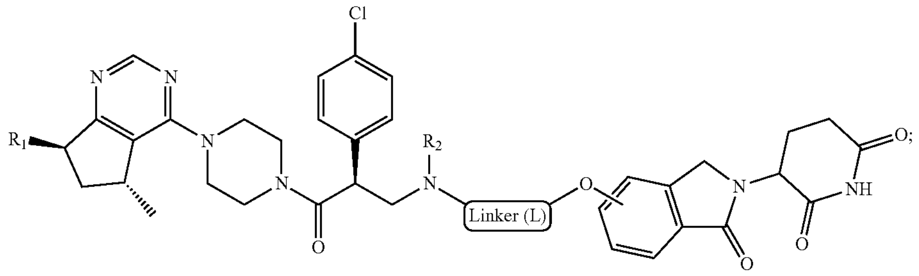
(I-24)
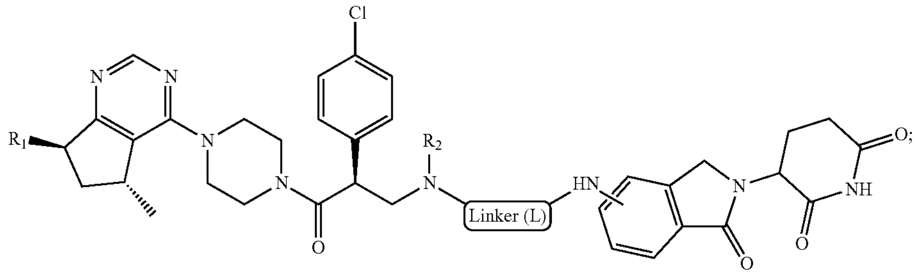
(I-25)
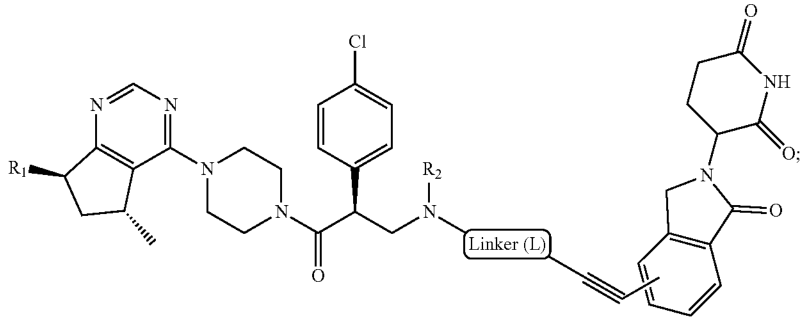

-continued
(I-26)
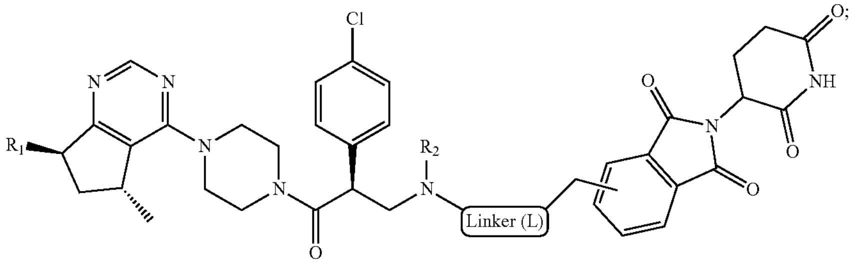
(I-27)
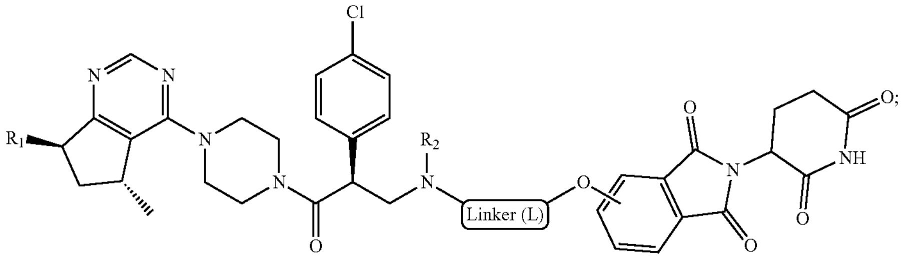
(I-28)
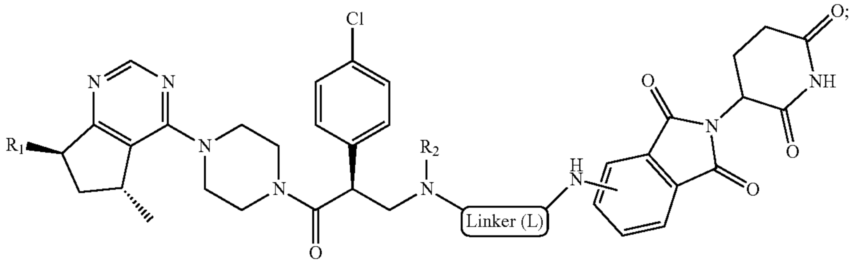
(I-29)
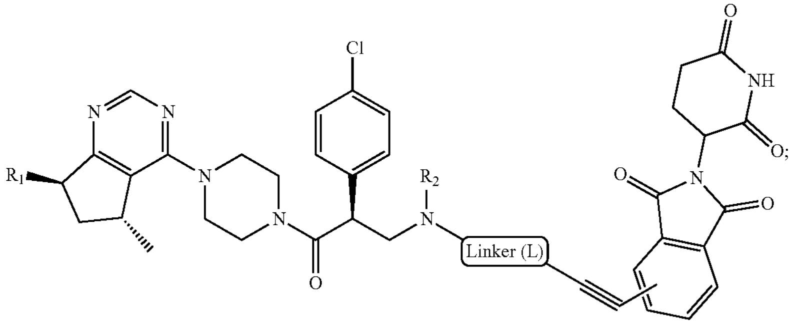
(I-30)
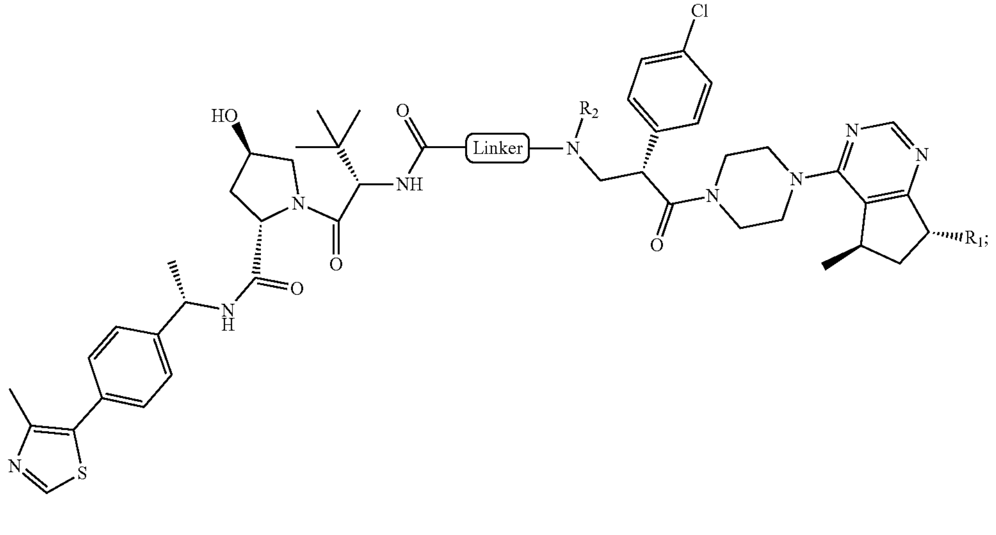

-continued
(I-31)
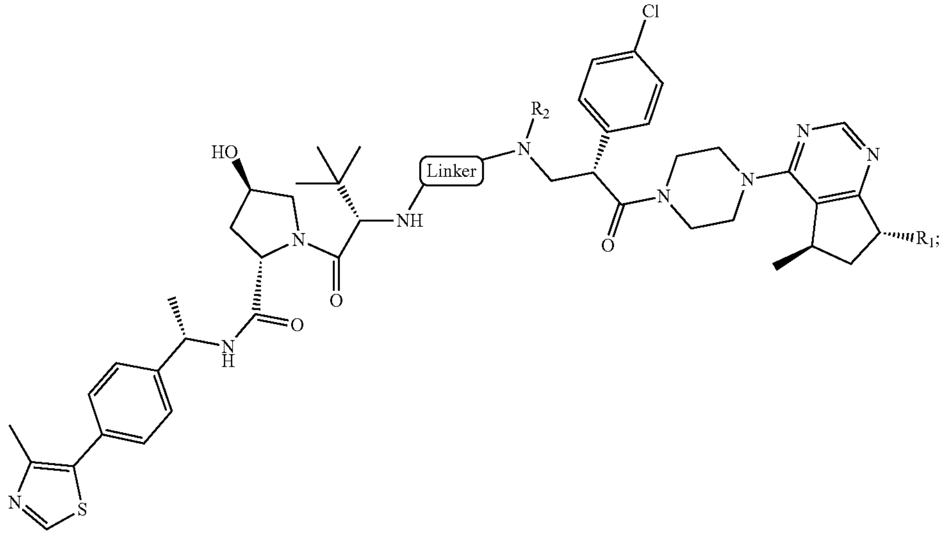
(I-32)
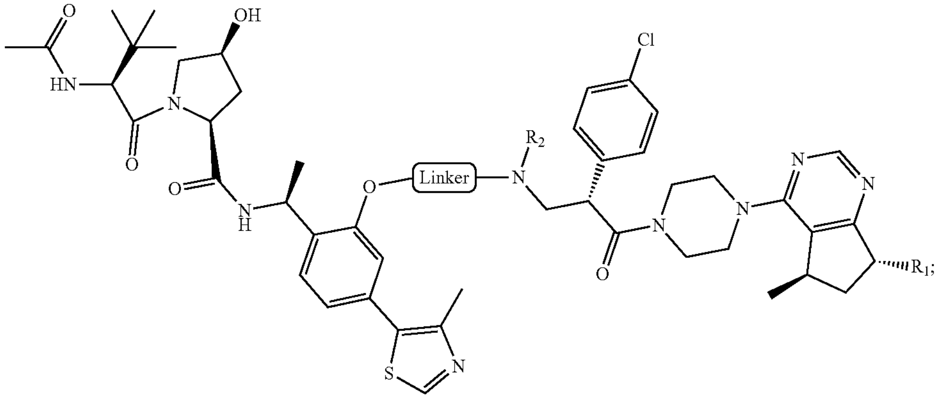
(I-33)
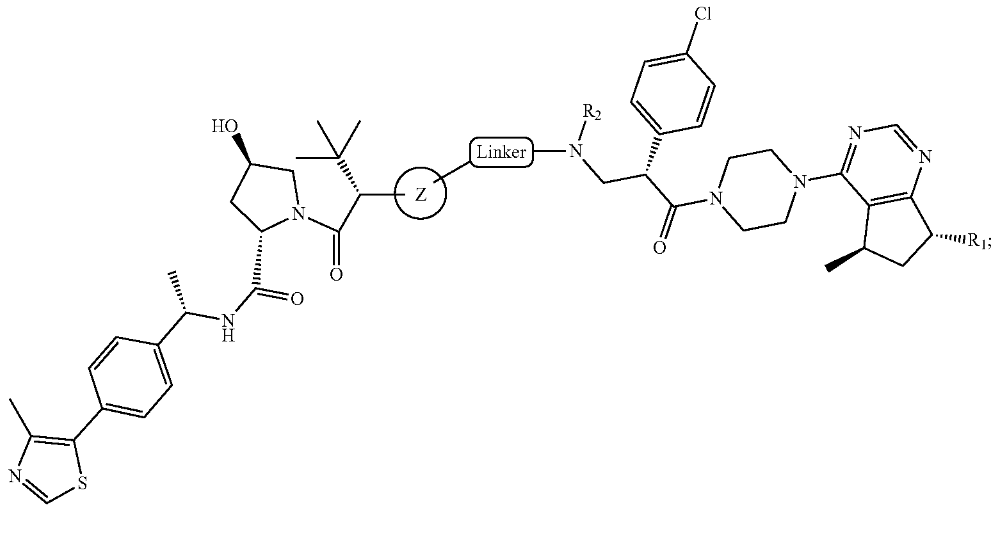
and

-continued (I-34)

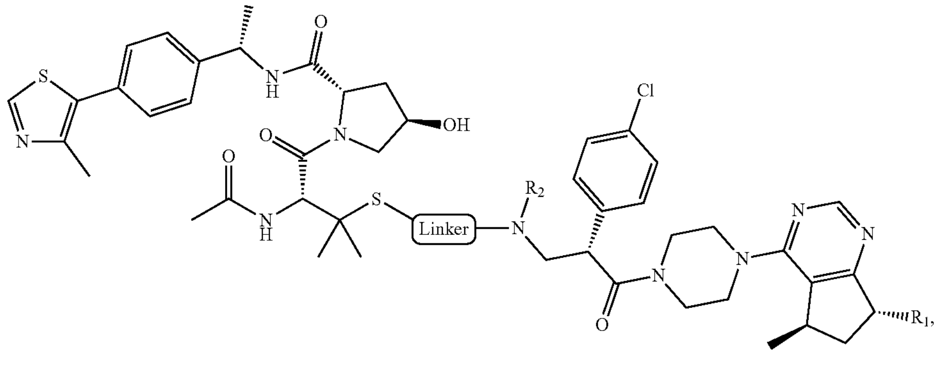

or a pharmaceutically acceptable salt, or stereoisomer thereof, wherein Z is a $C_5$-$C_6$ carbocyclic or heterocyclic group;

$R_1$ is H or OH; and $R_2$ is H, methyl, ethyl, or isopropyl.

11. A pharmaceutical composition, comprising a therapeutically effective amount of the bifunctional compound of claim 1, or a pharmaceutically acceptable salt or stereoisomer thereof, and a pharmaceutically acceptable carrier.

12. A method of treating a cancer mediated by dysfunctional AKT, comprising administering to a patient in need thereof a therapeutically effective amount of the bifunctional compound of claim 1 or pharmaceutically acceptable salt or stereoisomer thereof, wherein the cancer is breast cancer, endometrial cancer, cervical cancer, lung cancer, lymphoma, melanoma, or prostate cancer.

13. The method of claim 12, wherein the cancer is breast cancer.

14. The method of claim 13, wherein the breast cancer is early stage triple-negative breast cancer or metastatic triple-negative breast cancer.

15. The method of claim 14, further comprising co-administering to the patient a chemotherapeutic agent, wherein the chemotherapeutic agent is Trametinib, Dabrafenib, Lapatinib Ditosylate, Selumetinib, Bendamustine Hydrochloride, Rituximab, Dinaciclib, Hydroxychloroquine, Olaparib, Erlotinib Hydrochloride, Trastuzumab, Everolimus, Bicalutamide, Anastrozole, Goserelin Acetate, Fulvestrant, Paclitaxel, Bortezomib, Dexamethasone, Exemestane, Goserelin, Gemcitabine, Docetaxel, Prednisolone, Carboplatin, Uprosertib, Gefitinib, Cobimetinib, Oxaliplatin, 5-Fluorouracil, or Leucovorin.

16. The method of claim 15, wherein the chemotherapeutic agent is paclitaxel.

17. A bifunctional compound which is:

(1)

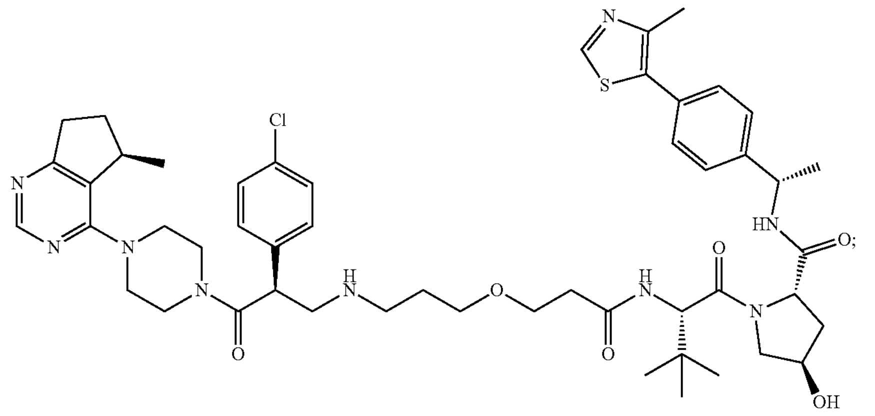

-continued
(2)
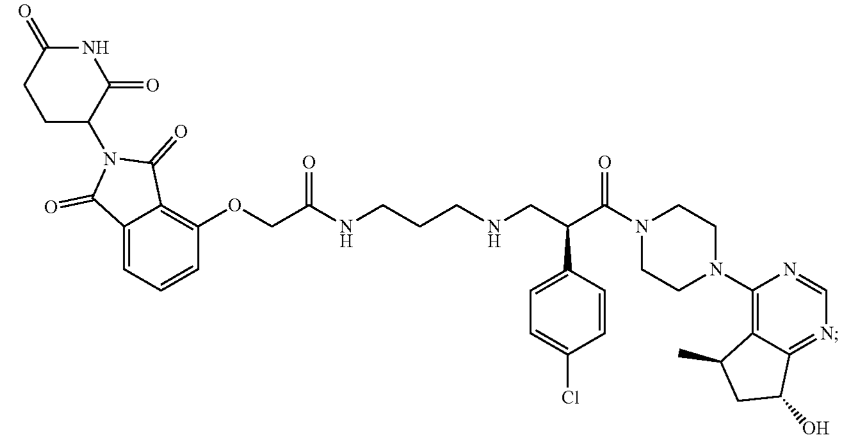
(3)
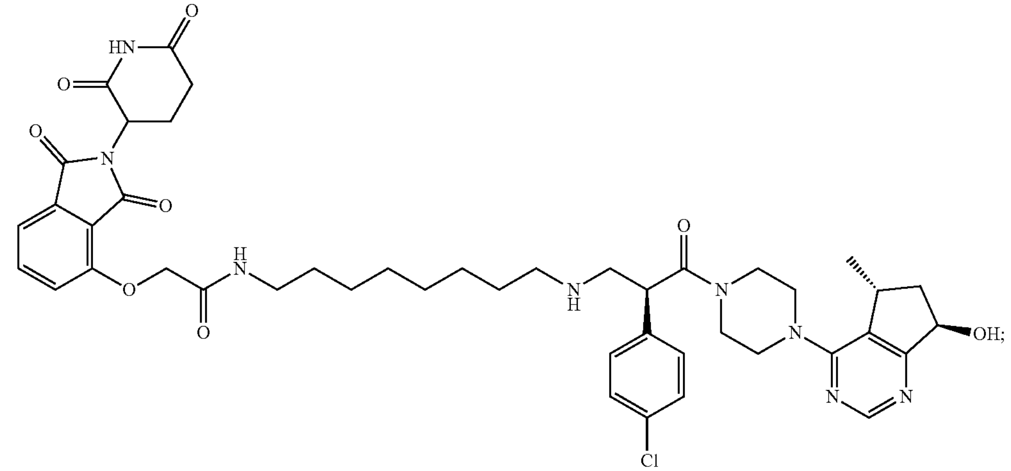
(4)
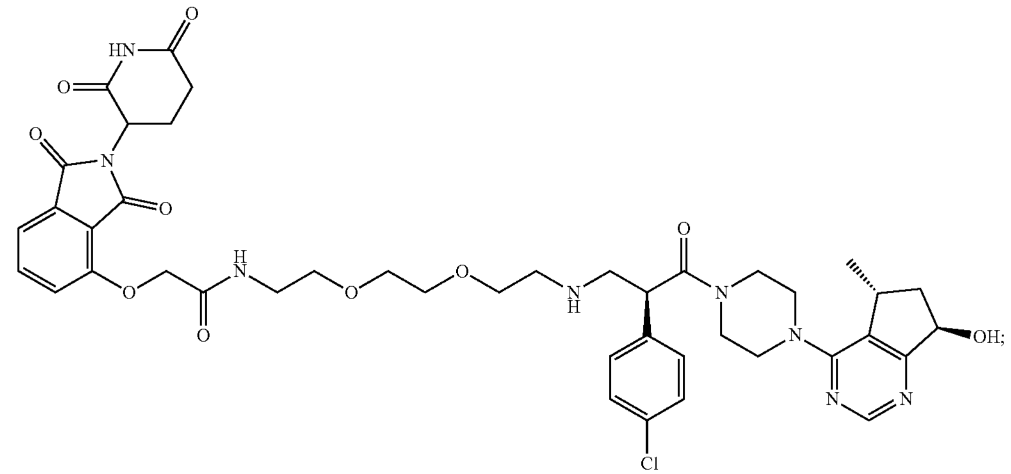

-continued
(5)
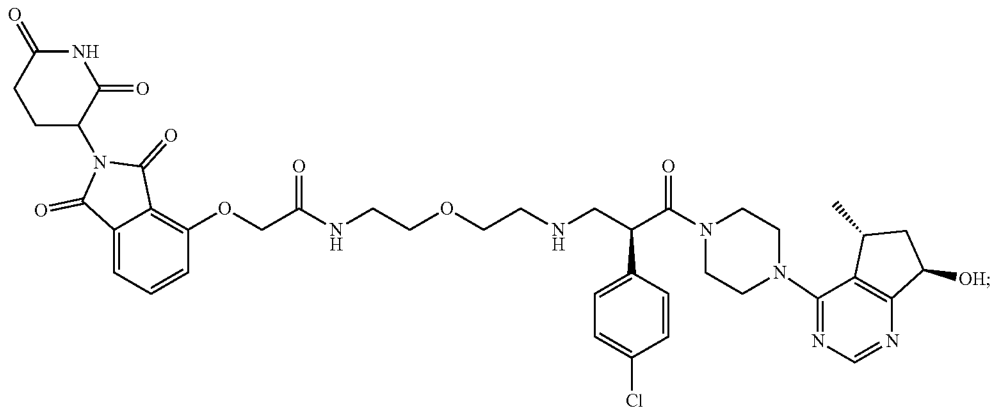
(6)
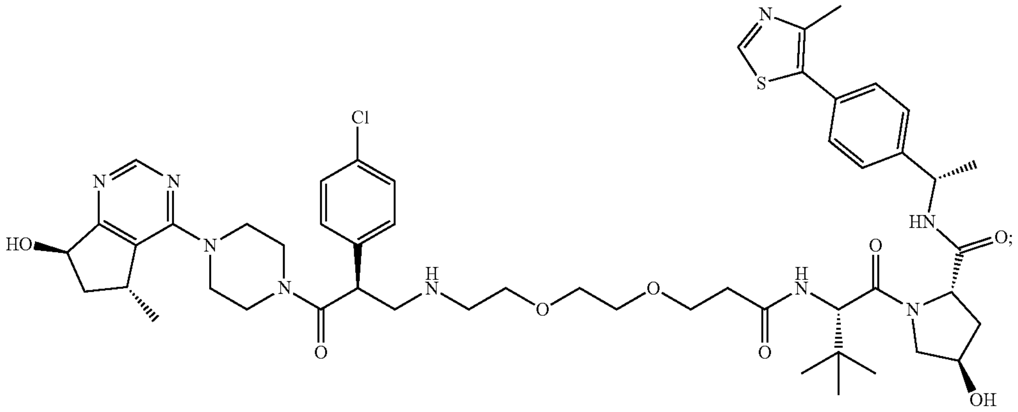
(7)
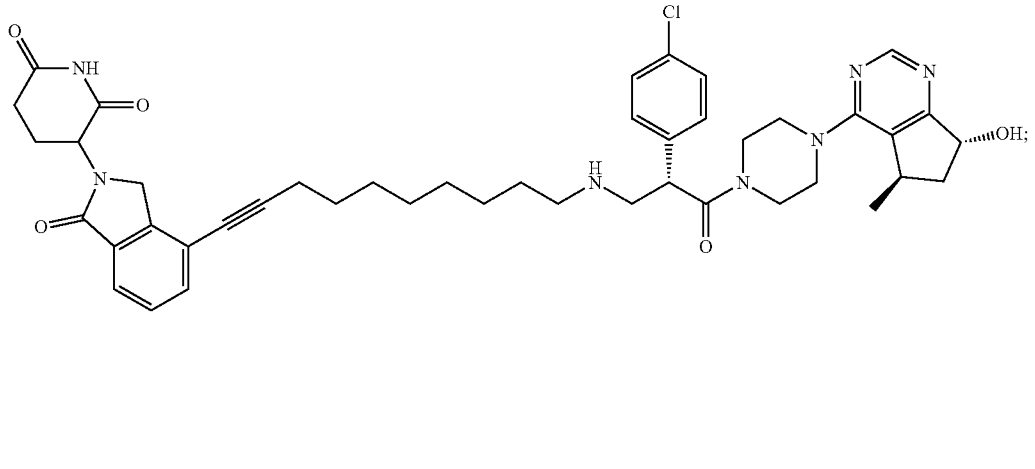
(8)
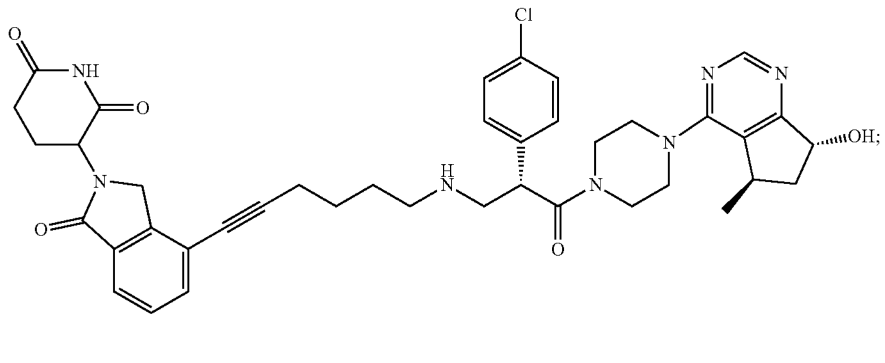

-continued
(9)
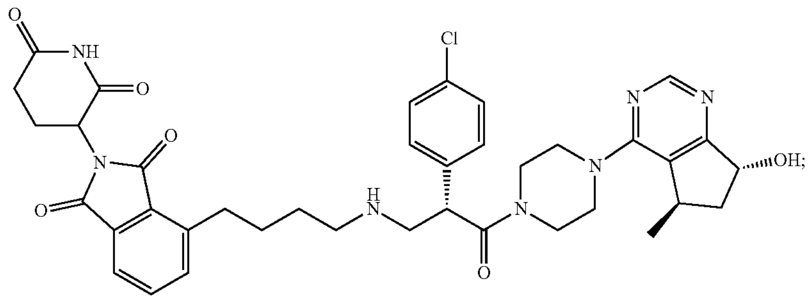
(10)
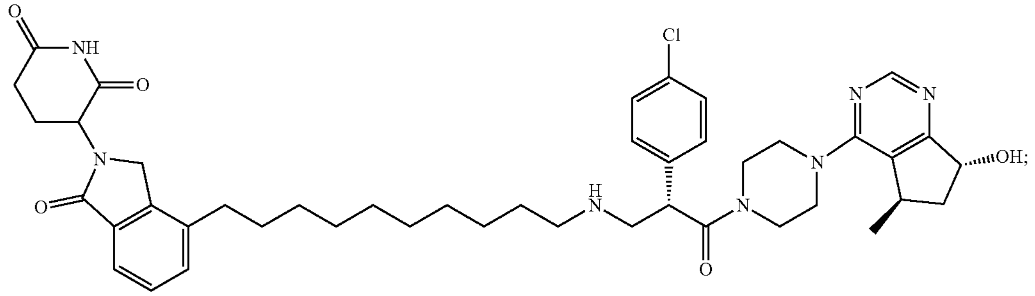
(11)
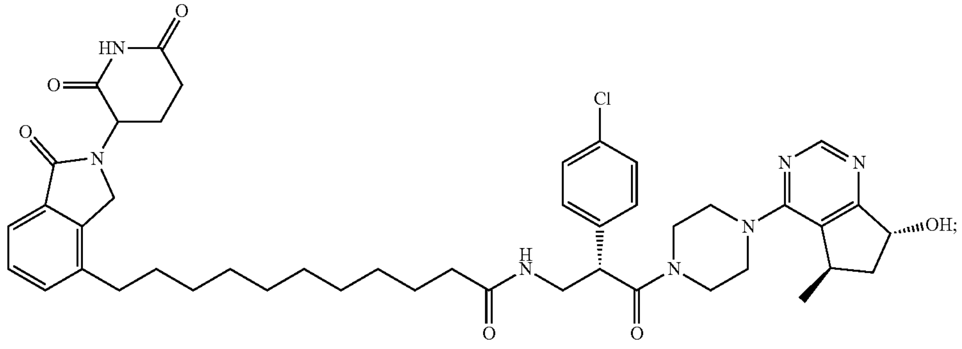
(12)
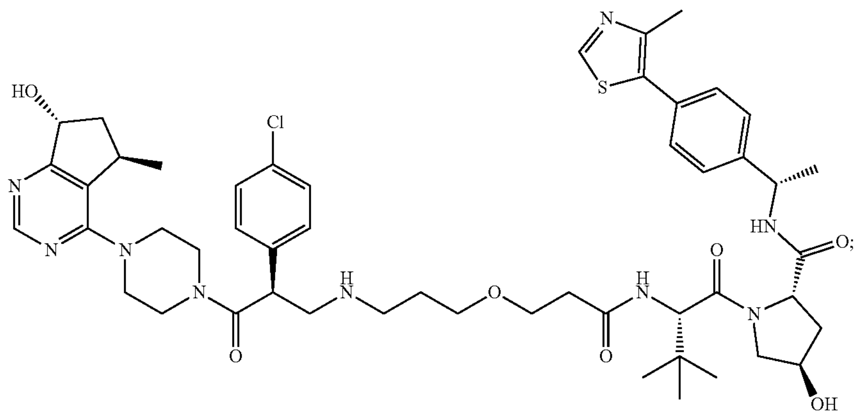

-continued
(13)
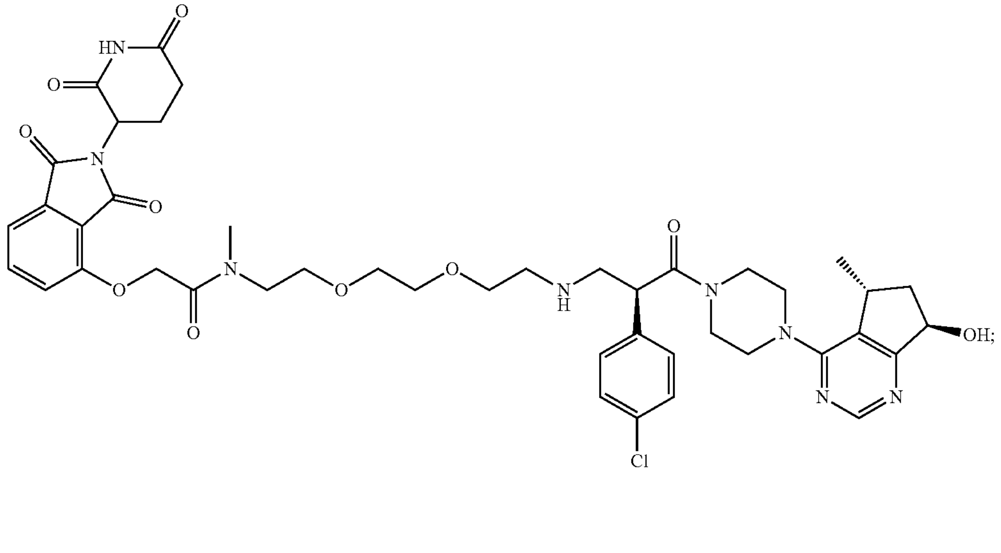
(14)
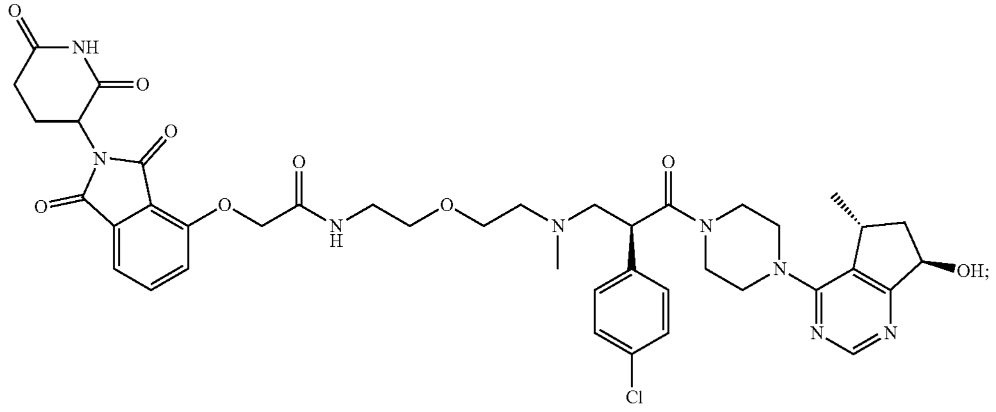
(15)
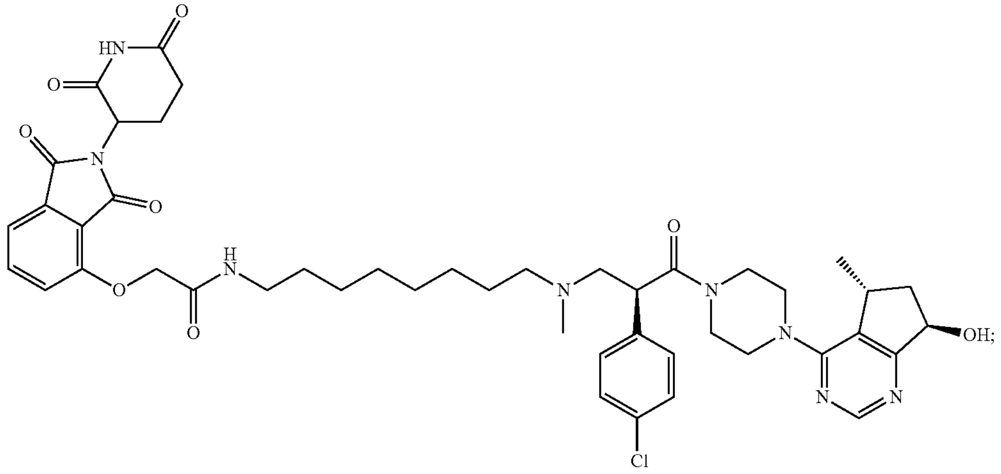

-continued
(16)
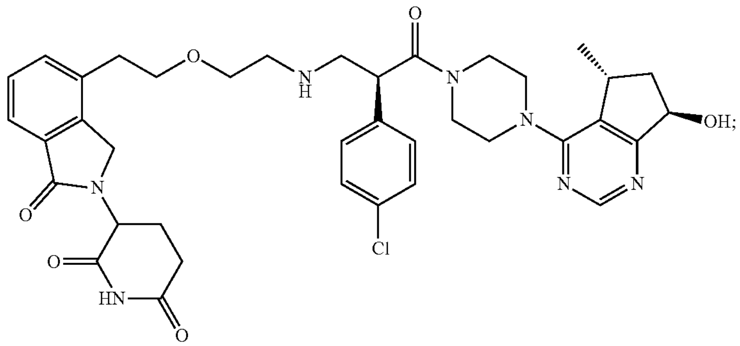
(17)
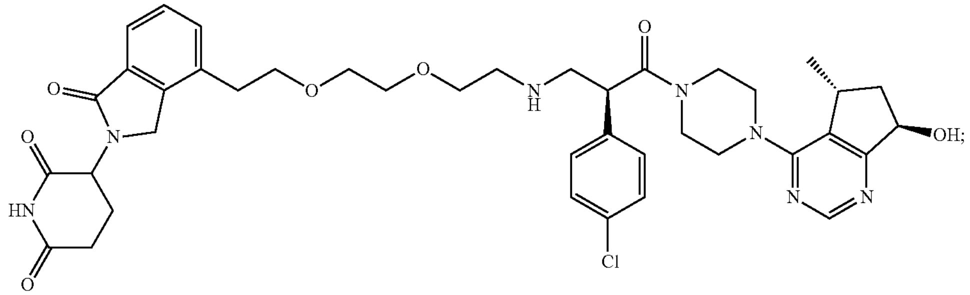
(18)
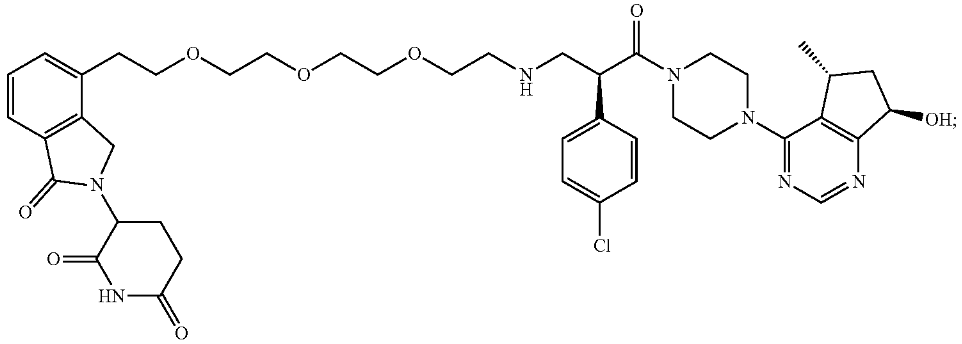
(19)
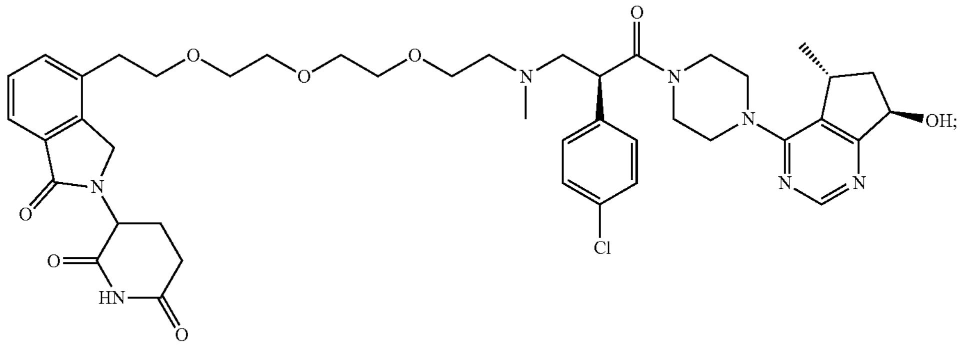

-continued (20)

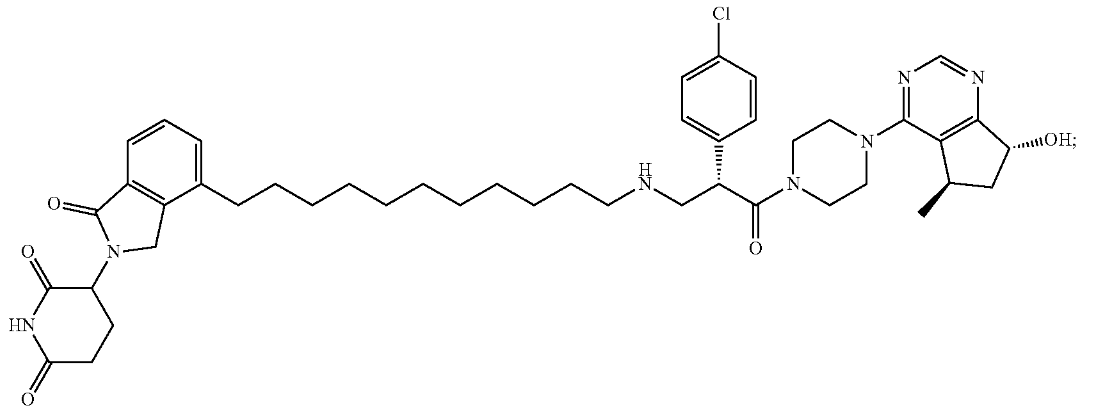

(21)

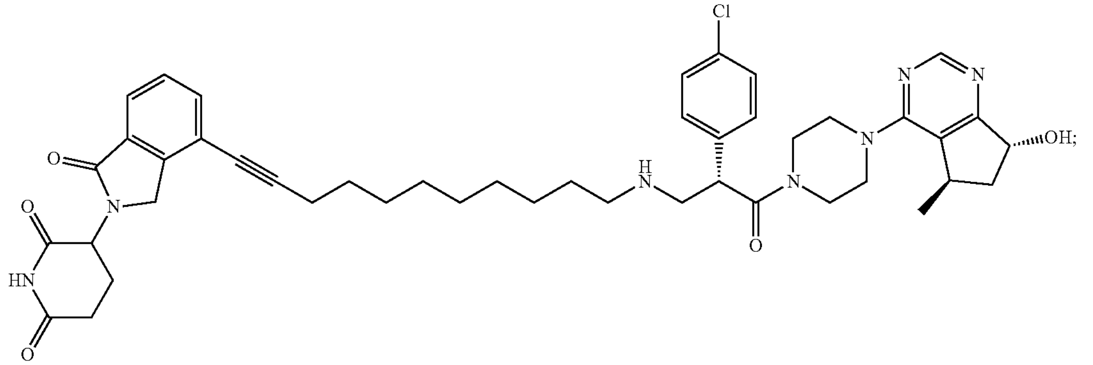

or (22)

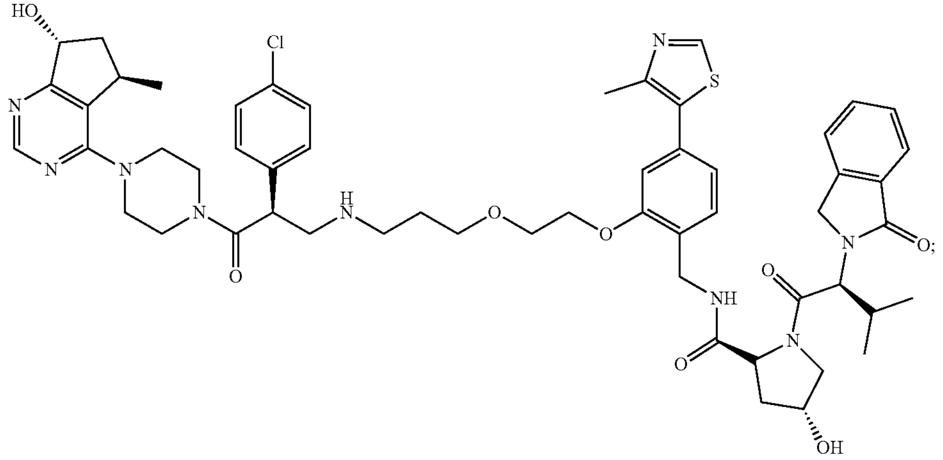

or a pharmaceutically acceptable salt or stereoisomer thereof.

18. A pharmaceutical composition, comprising a therapeutically effective amount of the bifunctional compound of claim 17, or a pharmaceutically acceptable salt or stereoisomer thereof, and a pharmaceutically acceptable carrier.

19. A method of treating a cancer mediated by dysfunctional AKT, comprising administering to a patient in need thereof a therapeutically effective amount of the bifunctional compound of claim 17 or pharmaceutically acceptable salt or stereoisomer thereof, wherein the cancer is breast cancer, endometrial cancer, cervical cancer, lung cancer, lymphoma, melanoma, or prostate cancer.

20. The method of claim 19, wherein the cancer is breast cancer.

21. The method of claim 20, wherein the breast cancer is early stage triple-negative breast cancer or metastatic triple-negative breast cancer.

22. The method of claim 21, further comprising co-administering to the patient a chemotherapeutic agent, wherein the chemotherapeutic agent is Trametinib, Dabrafenib, Lapatinib Ditosylate, Selumetinib, Bendamustine Hydrochloride, Rituximab, Dinaciclib, Hydroxychloroquine, Olaparib, Erlotinib Hydrochloride, Trastuzumab, Everolimus, Bicalutamide, Anastrozole, Goserelin Acetate, Fulvestrant, Paclitaxel, Bortezomib, Dexamethasone, Exemestane, Goserelin, Gemcitabine, Docetaxel, Prednisolone, Carboplatin, Uprosertib, Gefitinib, Cobimetinib, Oxaliplatin, 5-Fluorouracil, or Leucovorin.

23. The method of claim 22, wherein the chemotherapeutic agent is paclitaxel.
24. A bifunctional compound which is:
(23)
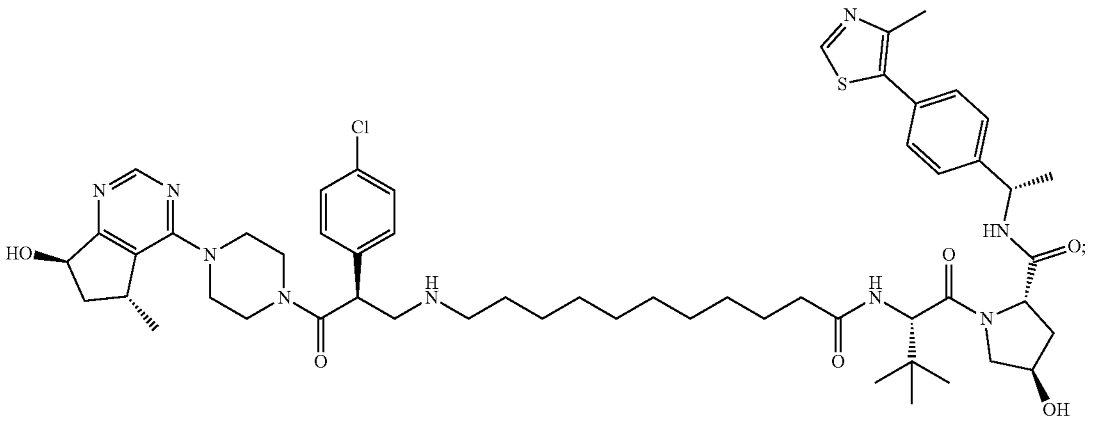
(24)
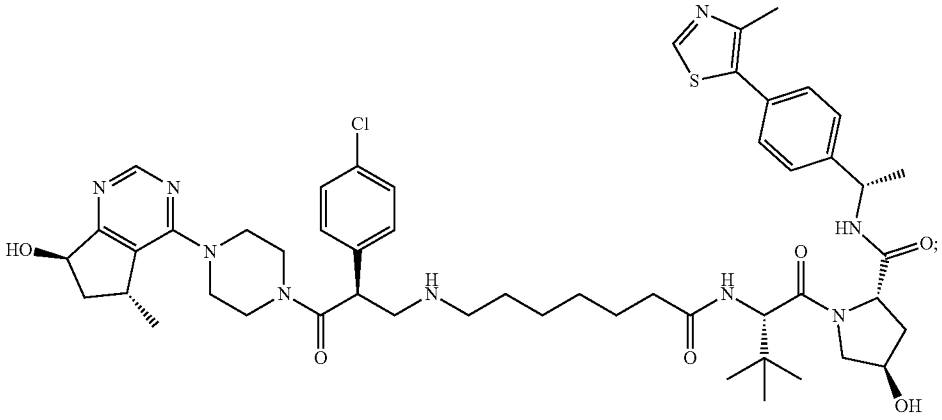
(25)
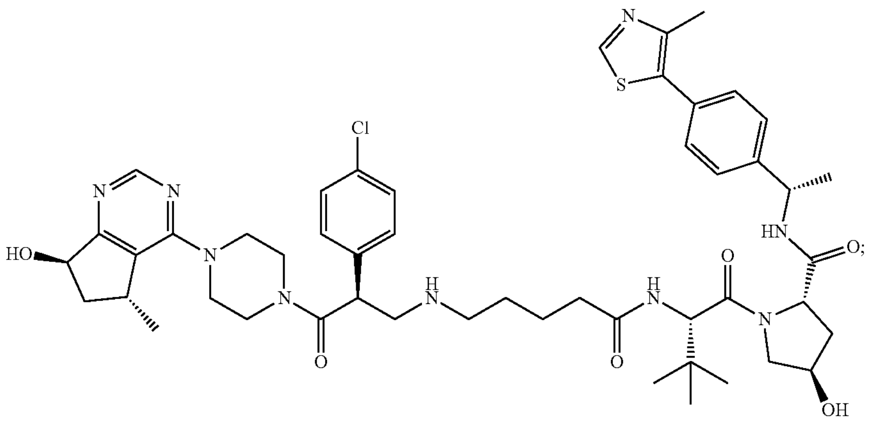

-continued
(26)
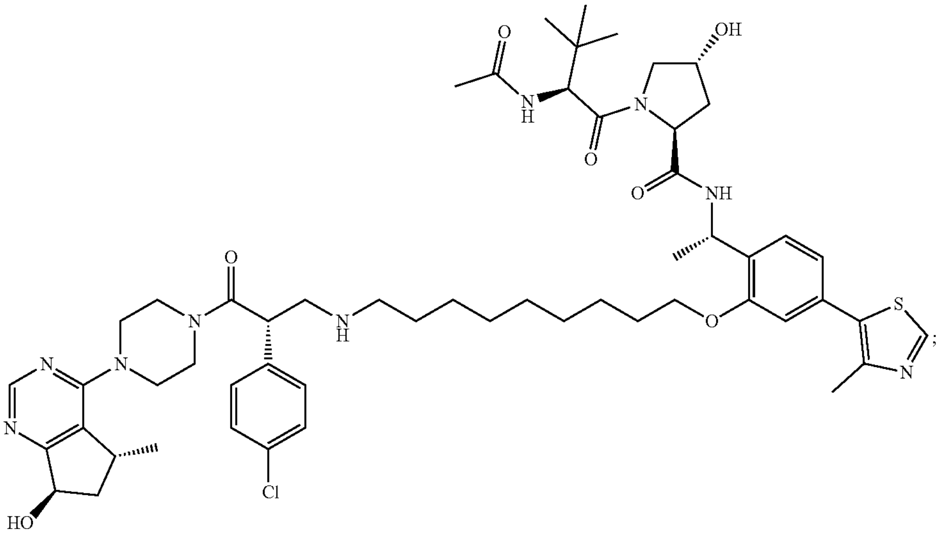
(27)
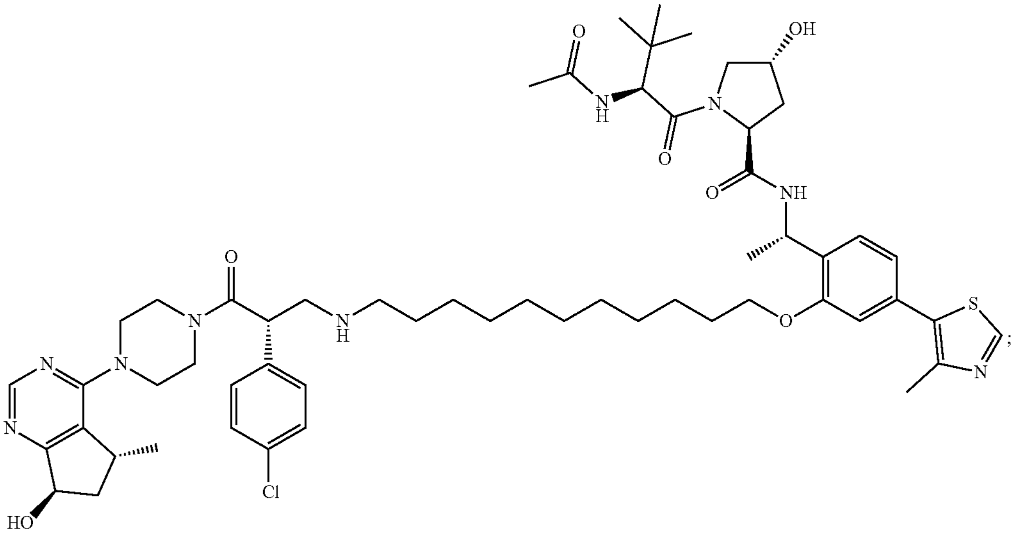
(28)
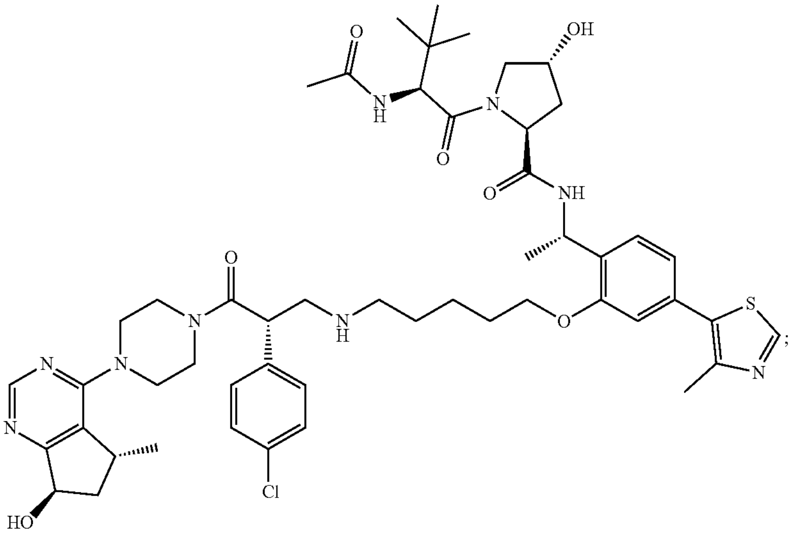
or

-continued (29)

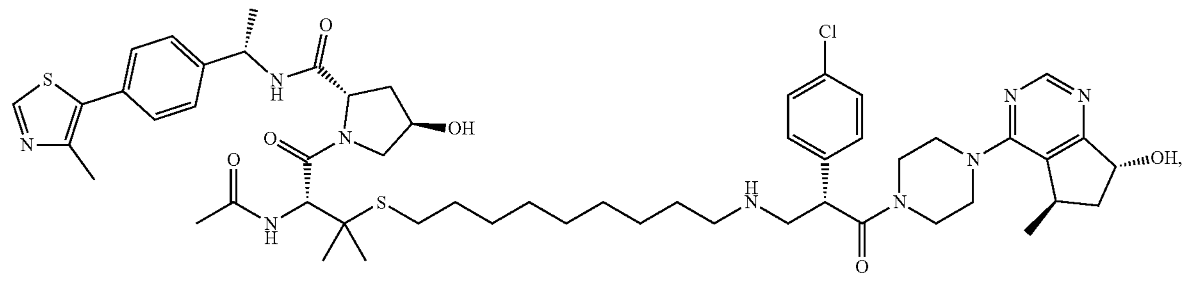

or a pharmaceutically acceptable salt or stereoisomer thereof.

25. A pharmaceutical composition, comprising a therapeutically effective amount of the bifunctional compound of claim 24, or a pharmaceutically acceptable salt or stereoisomer thereof, and a pharmaceutically acceptable carrier.

26. A method of treating a cancer mediated by dysfunctional AKT, comprising administering to a patient in need thereof a therapeutically effective amount of the bifunctional compound of claim 24 or pharmaceutically acceptable salt or stereoisomer thereof, wherein the cancer is breast cancer, endometrial cancer, cervical cancer, lung cancer, lymphoma, melanoma, or prostate cancer.

27. The method of claim 26, wherein the cancer is breast cancer.

28. The method of claim 27, wherein the breast cancer is early stage triple-negative breast cancer or metastatic triple-negative breast cancer.

29. The method of claim 28, further comprising co-administering to the patient a chemotherapeutic agent, wherein the chemotherapeutic agent is Trametinib, Dabrafenib, Lapatinib Ditosylate, Selumetinib, Bendamustine Hydrochloride, Rituximab, Dinaciclib, Hydroxychloroquine, Olaparib, Erlotinib Hydrochloride, Trastuzumab, Everolimus, Bicalutamide, Anastrozole, Goserelin Acetate, Fulvestrant, Paclitaxel, Bortezomib, Dexamethasone, Exemestane, Goserelin, Gemcitabine, Docetaxel, Prednisolone, Carboplatin, Uprosertib, Gefitinib, Cobimetinib, Oxaliplatin, 5-Fluorouracil, or Leucovorin.

30. The method of claim 29, wherein the chemotherapeutic agent is paclitaxel.

* * * * *